(12) United States Patent
Doyle et al.

(10) Patent No.: US 10,984,903 B2
(45) Date of Patent: Apr. 20, 2021

(54) MODULAR BLOOD TREATMENT SYSTEMS, UNITS, AND METHODS

(71) Applicant: Fresenius Medical Care Holdings, Inc., Waltham, MA (US)

(72) Inventors: Matthew Doyle, Concord, CA (US); Lee Tanenbaum, Walnut Creek, CA (US); Donovan Halliburton, Martinez, CA (US); Eric Hoffstetter, Pleasanton, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 16/568,528

(22) Filed: Sep. 12, 2019

(65) Prior Publication Data
US 2020/0000995 A1 Jan. 2, 2020

Related U.S. Application Data

(63) Continuation of application No. 15/387,053, filed on Dec. 21, 2016, now Pat. No. 10,532,145.
(Continued)

(51) Int. Cl.
*A61B 50/13* (2016.01)
*A61M 1/16* (2006.01)
(Continued)

(52) U.S. Cl.
CPC .......... *G16H 20/40* (2018.01); *A61M 1/1629* (2014.02); *A61M 1/1696* (2013.01);
(Continued)

(58) Field of Classification Search
CPC ...... A61M 1/34; A61M 1/3653; A61M 39/10; A61M 2205/12; A61B 50/13
See application file for complete search history.

(56) References Cited

U.S. PATENT DOCUMENTS

| 8,562,834 B2 | 10/2013 | Kamen et al. |
| 2007/0169825 A1 | 7/2007 | Packham et al. |

(Continued)

FOREIGN PATENT DOCUMENTS

| JP | 2007-215557 A | 8/2007 |
| WO | 2010121819 A1 | 10/2010 |

(Continued)

OTHER PUBLICATIONS

International Search Report for Application No. PCT/US2016/068031, published by the EPO, dated Apr. 5, 2017 (Form PCT/ISA/210), including corresponding Written Opinion of the International Searching Authority (Form PCT/ISA/237), (16 pages in total).

(Continued)

*Primary Examiner* — Bradley R Spies
(74) *Attorney, Agent, or Firm* — Kilyk & Bowersox, P.L.L.C.

(57) ABSTRACT

A portable adapter is provided that can include a closure system configured to control the flow of blood and/or dialysate between the adapter and a blood treatment apparatus. Modular systems are also provided that include the portable adapter engaged with various units such as a portable blood processing module, a non-portable base module, and/or a remote module. Methods of conducting blood treatments such as blood circulation, hemodialysis, and hemofiltration, hemodiafiltration, using the modular systems are also provided. The systems, units, and methods enable the engagement and disengagement of the adapter from the various units to conduct, interrupt, and resume blood treatments without disconnecting the adapter from the vasculature of a patient. Modular systems including interchangeable portable and base modules configured for various blood treatments are also provided that can be engaged (Continued)

and disengaged with each other without disconnecting the portable module from the vasculature of a patient.

25 Claims, 32 Drawing Sheets

Related U.S. Application Data

(60) Provisional application No. 62/270,136, filed on Dec. 21, 2015.

(51) Int. Cl.
*A61M 1/26* (2006.01)
*A61M 1/34* (2006.01)
*A61M 1/36* (2006.01)
*A61M 39/10* (2006.01)
*A61M 1/30* (2006.01)
*G16H 20/40* (2018.01)
*G16H 40/63* (2018.01)

(52) U.S. Cl.
CPC ............ *A61M 1/267* (2014.02); *A61M 1/301* (2014.02); *A61M 1/34* (2013.01); *A61M 1/3413* (2013.01); *A61M 1/3621* (2013.01); *A61M 1/3644* (2014.02); *A61M 1/3653* (2013.01); *A61M 1/3655* (2013.01); *A61M 1/3659* (2014.02); *A61M 1/3672* (2013.01); *A61M 39/10* (2013.01); *G16H 40/63* (2018.01); *A61B 50/13* (2016.02); *A61M 39/1011* (2013.01); *A61M 2039/1077* (2013.01); *A61M 2205/12* (2013.01); *A61M 2205/128* (2013.01); *A61M 2205/18* (2013.01); *A61M 2205/3337* (2013.01); *A61M 2205/3368* (2013.01); *A61M 2205/3393* (2013.01); *A61M 2205/3561* (2013.01); *A61M 2205/505* (2013.01); *A61M 2205/581* (2013.01); *A61M 2205/582* (2013.01); *A61M 2205/583* (2013.01); *A61M 2205/587* (2013.01); *A61M 2205/6054* (2013.01); *A61M 2205/6063* (2013.01); *A61M 2205/6072* (2013.01); *A61M 2205/6081* (2013.01); *A61M 2205/8206* (2013.01); *A61M 2205/8293* (2013.01); *A61M 2209/086* (2013.01); *A61M 2209/088* (2013.01)

(56) References Cited

U.S. PATENT DOCUMENTS

| | | | |
|---|---|---|---|
| 2009/0120864 A1* | 5/2009 | Fulkerson | A61M 1/1601 210/198.1 |
| 2009/0173682 A1 | 7/2009 | Robinson et al. | |
| 2010/0252490 A1 | 10/2010 | Fulkerson et al. | |
| 2010/0274168 A1 | 10/2010 | Gronau et al. | |
| 2011/0189048 A1 | 8/2011 | Curtis et al. | |
| 2011/0315611 A1 | 12/2011 | Fulkerson et al. | |
| 2012/0175296 A1 | 7/2012 | Wehmeyer et al. | |
| 2012/0247567 A1 | 10/2012 | Herrmann et al. | |
| 2013/0018355 A1 | 1/2013 | Brand et al. | |
| 2013/0213890 A1 | 8/2013 | Kelly et al. | |
| 2013/0261529 A1 | 10/2013 | O'Mahony | |
| 2013/0310726 A1 | 11/2013 | Miller et al. | |
| 2017/0173251 A1 | 6/2017 | Doyle et al. | |

FOREIGN PATENT DOCUMENTS

| | | |
|---|---|---|
| WO | 2011017215 A1 | 2/2011 |
| WO | 2011063923 A1 | 6/2011 |
| WO | 2014151322 A1 | 9/2014 |
| WO | 2014/161008 A1 | 10/2014 |

OTHER PUBLICATIONS

International Preliminary Report on Patentability (Form PCT/IB/373) for International Patent Application No. PCT/US2016/068031, bearing a date of issuance of Jun. 26, 2018, including the Written Opinion of the International Searching Authority (Form PCT/ISA/237) and separate sheets (9 pages total).

Extended European Search Report for European Application No. EP 20175560.0, published by the European Patent Office (EPO), dated Oct. 22, 2020, including corresponding Communication, Information on Search Strategy, 1-page Annex, and 6-page EPO Form 1703, 10 pages total.

* cited by examiner

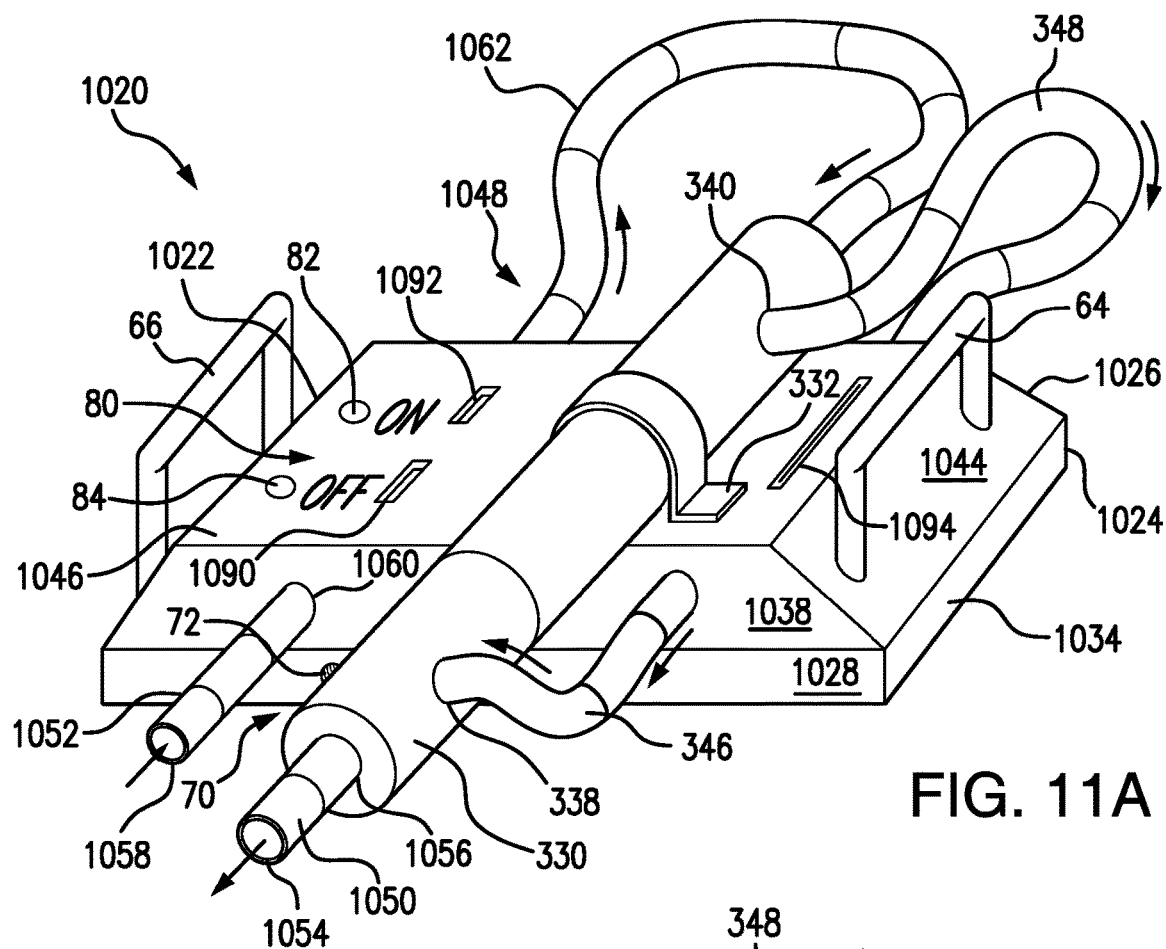
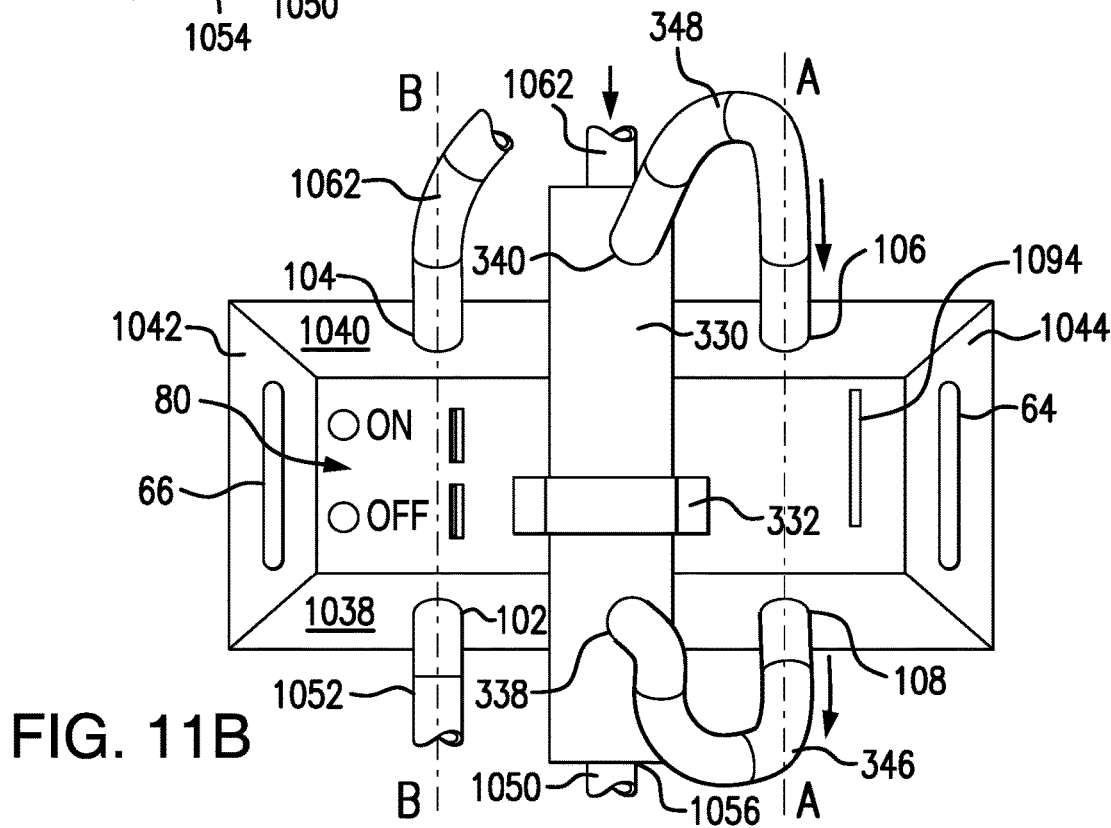

MODULAR BLOOD TREATMENT SYSTEMS, UNITS, AND METHODS

CROSS-REFERENCE TO RELATED APPLICATIONS

This application is a continuation of U.S. patent application Ser. No. 15/387,053, filed Dec. 21, 2016, now allowed, which claims priority under 35 USC § 119 to U.S. Patent Application No. 62/270,136, filed Dec. 21, 2015, the entire contents of both of which are incorporated herein by reference in their entireties.

FIELD OF THE INVENTION

The present disclosure relates to blood treatment systems, units, modules, apparatuses, and methods useful for blood circulation, hemodialysis, hemofiltration, hemodiafiltration, apheresis, and the like.

BACKGROUND OF THE INVENTION

Extracorporeal blood treatments such as hemodialysis and hemofiltration can be lengthy procedures leading to considerable disruption of a patient's daily schedule. The size and limited portability of most dialysis systems can significantly reduce the mobility of patients and their ability to engage in routine activities or easily interrupt a treatment session in the event of an emergency or non-emergency event. If a treatment session is interrupted, the patient often has to undergo the cumbersome process of disconnecting from extracorporeal blood tubing. When resuming a treatment session, a new set of extracorporeal blood tubing is often required leading to waste, increased cost, stress on the patient's skin and vasculature, and greater opportunity for infection and contamination. Existing blood processing machines often limit use at home to a single station, room, or floor, which can also disrupt a patient's daily schedule and potentially lead to a lack of compliance with a prescribed regimen. Existing machines and systems are also limited in their capacity to handle high and/or unexpected patient numbers at treatment centers, potentially leading to life-threatening delays. For a given period of time, a treatment center may have to dedicate the use of a particular blood processing machine to a single patient while others are forced to wait or seek treatment elsewhere. At other times, a treatment center may have excess capacity that translates to higher overhead and increased healthcare costs.

Accordingly, there is a need for blood processing clinics, systems, machines, and methods that provide greater flexibility, convenience, and functionality to both patients and caregivers.

SUMMARY OF THE PRESENT INVENTION

A feature of the present invention is to provide greater flexibility and convenience to dialysis patients and caregivers alike.

Another feature of the present invention is to provide machines and methods for reducing the use of disposables and reducing negative impact on a patient's skin and vasculature.

A further feature of the present invention is to provide greater mobility to patients, and to enable a blood processing procedure that can begin in one location and be completed in another location, whether in a different room, on a different floor, or in a different building.

An additional feature of the present invention is to increase the efficiency of dialysis treatment centers to serve more patients without the need for increasing the total number of blood processing apparatuses at a given site.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a portable blood circuit adapter. The adapter can include an extracorporeal blood circuit tubing set including a venous line and a, arterial line, each of the venous line and the arterial line having an adapter end and a patient end, the patient end being configured to connect with a vascular access or vascular access implant. The adapter can also include an adapter housing comprising a module connector configured to engage a complementary inter-module connector of a blood treatment apparatus that comprises a blood pump configured to pump blood extracorporeally through the extracorporeal blood circuit tubing set. The adapter housing can comprise tube connectors for fixing the adapter ends of the venous line and the arterial line to the adapter housing. The tube connectors are in fluid communication with the module connector and provide interruptible fluid flow paths between the venous line and the module connector and between the arterial line and the module connector. The adapter can further include a closure system mounted in or on the adapter housing and configured to (1) interrupt fluid communication between the venous line and the module connector and between the arterial line and the module connector, when the portable blood circuit adapter is disconnected from a blood treatment apparatus, and (2) provide fluid communication between the venous line and the module connector and between the arterial line and the module connector when the portable blood circuit adapter is connected to a complementary inter-module connector of a blood treatment apparatus.

The present invention also relates to a modular system comprising the portable blood circuit adapter and a portable blood processing module, the module comprising an inter-module connector that is complementary to the module connector of the adapter housing. The module can also comprise a module blood circuit including a to-patient line and a from-patient line, and a first blood pump. Each of the to-patient line and the from-patient line of the module blood circuit can have a connector end in fluid communication with the inter-module connector. The first blood pump can be configured to circulate blood between the patient and the module blood circuit through the blood line set.

The present invention further relates to a modular system comprising the portable blood circuit adapter and a non-portable, first base module comprising an inter-module connector that is complementary to the module connector of the adapter housing. Herein, by base module, what is meant is a non-portable installation that is not intended to be picked up and moved. The base modules described herein can be hard-wired, plumbed, and the like, so as to be permanently installed at a base location. Portable modules of the present invention can be brought to and connected with the base modules. Base modules as described herein can include wiring to plug into a 110 Volt or 220 Volt wall outlet as opposed to being run by batteries. The first base module can also comprise a first base module blood circuit including a to-patient line and a from-patient line, a second blood pump, a dialysate pump, and a dialysate circuit. The second blood pump can be configured to circulate blood through the first base module blood circuit, through the extracorporeal blood circuit tubing set, and to and from a patient. The dialysate circuit can comprise a blood filter, for example, a dialyzer, and the blood filter can be in fluid communication with the first base module blood circuit and the dialysate circuit.

The present invention also relates to a method that comprises providing a modular system including a first base module of the invention, connecting each of the patient ends of the venous line and the arterial line to vascular access points of a patient, engaging the portable blood circuit adapter with the first base module, and performing at least one blood treatment on the patient. The at least one blood treatment can comprise blood circulation, hemodialysis, hemofiltration, hemodiafiltration, or any combination thereof.

The present invention further relates to a method that comprises providing a modular system including a portable blood processing module of the invention, connecting each of the patient ends of the venous line and the arterial line to vascular access points of a patient, engaging the portable blood circuit adapter with the portable blood processing module, and performing at least one blood treatment on the patient. The at least one blood treatment can comprise blood circulation, hemodialysis, hemofiltration, hemodiafiltration, or any combination thereof.

The present invention also relates to a modular system comprising the portable blood circuit adapter, a base module comprising a dialysate circuit and a first dialysate pump in operative communication with the dialysate circuit, and a first remote module located away from and not adjacent the base module and comprising a first blood pump. Herein, by remote, what is meant is a modular component that is spaced away from, for example, at least one foot away, at least five feet away, at least ten feet away, at least twenty feet away, at least fifty feet away, at least 100 feet away, or some other distance away from a base module, portable module, or other remote module with which the remote module interacts. A remote module can be, for example, located in a different room of a clinic, hospital, or home with respect to a base module with which the remote module interacts, such as to form a blood circuit or dialysate circuit through interconnected tubing. The first remote module can comprise an inter-module connector that is complementary to the module connector of the adapter housing, and a local blood circuit in fluid communication with the inter-module connector. The first blood pump can be in operative communication with the local blood circuit. The dialysate circuit can extend from the base module to the first remote module. A first blood filter can be in fluid communication with both the local blood circuit and the dialysate circuit. The modular system can further comprise a second remote module located away from the base module and comprising a second blood pump, a second inter-module connector that is complementary to the module connector of the adapter housing, and a second local blood circuit in fluid communication with the second inter-module connector. The second blood pump can be in operative communication with the second local blood circuit. The dialysate circuit can extend from the base module to the second remote module.

The present invention further relates to a method that comprises providing the modular system with at least a first remote module, connecting each of the patient ends of the venous line and the arterial line to vascular points of a patient, engaging the portable blood circuit adapter with the first remote module; and performing at least one blood treatment on the patient.

The present invention also relates to a method that comprises providing the modular system including at least the first and second remote modules, connecting each of the patient ends of the venous line and the arterial line to vascular points of a patient, engaging the portable blood circuit adapter with the first remote module, performing at least one blood treatment on the patient, disengaging the portable blood circuit adapter from the first remote module, and without disconnecting the extracorporeal blood circuit tubing set from the patient, engaging the portable blood circuit adapter with the second remote module.

The present invention further relates to a modular system comprising a first base module and a first portable module. The first base module can comprise a dock and be configured to dock a portable extracorporeal blood circuit module. The first base module can comprise a base module housing, a primary dialysate circuit comprising a primary dialysate pump, a primary dialysate line, and a first inter-module connector. The first portable module can be configured to dock the first base module in a docked configuration and be configured to operate independently of the first base module in an undocked configuration. The first portable module can comprise a first portable module housing, a blood pump mounted in or on the first portable module housing, a first extracorporeal blood circuit tubing set, and a second inter-module connector complementary to the first inter-module connector and configured to connect to the first inter-module connector in the docked configuration. The blood pump can be configured to releasably engage the extracorporeal blood circuit tubing set.

The present invention also relates to a method that comprises providing the base module and portable module modular system, connecting a patient to the first extracorporeal blood circuit tubing set, engaging the first portable module with the first base module, and performing at least one blood treatment on the patient, for example, hemodialysis, hemofiltration, hemodiafiltration, or any combination thereof.

The present invention further relates to a method that comprises providing the base module and portable module modular system, connecting a patient to the first extracorporeal blood circuit tubing set, performing at least one blood treatment on the patient, using the first portable module independent of the first base module, then, without disconnecting the patient from the first extracorporeal blood circuit tubing set, engaging the first portable module with the first base module, and performing at least one blood treatment on the patient while the first portable module is engaged with the first base module.

The present invention also relates to a portable blood circulation unit for an extracorporeal blood circuit. The portable blood circulation unit can comprise a housing configured to engage a blood treatment apparatus comprising a blood pump configured to pump blood from and to a patient extracorporeally through an extracorporeal blood circuit. The portable blood circulation unit can also comprise a unit blood pump mounted in or on the housing and configured to releasably engage and circulate blood through an extracorporeal short circuit blood circuit. The portable blood circulation unit can further comprise a battery-powered power source configured to power the unit blood pump. An extracorporeal short circuit blood circuit can be releasably engaged with the unit blood pump. The extracorporeal short circuit blood circuit and the housing can be together configured to provide a bypass mode of operation wherein the portable blood circulation unit is not engaged with a blood treatment apparatus and blood is circulated to and from the patient, through the extracorporeal short circuit blood circuit. The bypass mode can operate independent of the blood treatment apparatus. A first inter-module connector can be configured to connect the portable blood circulation unit to a blood treatment apparatus and form a fluid communication between the extracorporeal short circuit blood circuit and a base module blood circuit of the blood treatment apparatus. The portable blood circulation unit can be provided in combination with a blood treatment apparatus. The blood treatment apparatus can comprise a base module blood circuit and a second inter-module connector configured to connect the blood treatment apparatus to the portable blood circulation unit and to form a fluid communication between the extracorporeal short circuit blood circuit and the base module blood circuit.

The present invention further relates to a method that comprises providing the portable blood circulation unit, connecting the extracorporeal short circuit blood circuit to a patient, engaging the first inter-module connector to a blood treatment apparatus having a complementary second inter-module connector, disengaging the portable blood circulation unit from the blood treatment apparatus, and engaging the first inter-module connector with a second blood treatment apparatus or reengaging the first inter-module connector with the blood treatment apparatus.

The present invention also relates to a portable blood circuit adapter comprising an adapter housing configured to alternatively engage respective apparatus housings of at least two different blood treatment apparatuses that comprise respective blood pumps configured to pump blood extracorporeally. An extracorporeal blood circuit is attached to the adapter housing and is configured to alternatively engage the respective blood pumps. The extracorporeal blood circuit can comprise an arterial blood line, a venous blood line, and a blood filter. The blood filter can be configured for fluid communication with different respective dialysate circuits in the at least two different blood treatment apparatuses.

The present invention further relates to a modular system that comprises a blood circulation adapter having an adapter dialysate circuit. A blood filter is in fluid communication with the extracorporeal blood circuit and the adapter dialysate circuit. The modular system can also comprise a blood treatment apparatus comprising a blood pump and an apparatus dialysate circuit. The blood treatment apparatus is configured to engage the blood circulation adapter and to perform at least one blood treatment on a patient. The modular system can further include a closure system configured to provide fluid communication between the adapter dialysate circuit and the apparatus dialysate circuit.

The present invention further relates to a method that comprises providing the modular system, connecting the extracorporeal blood circuit to the patient, engaging the portable blood circuit adapter with the blood treatment apparatus, opening the closure system to provide fluid communication of dialysate between the blood circulation adapter and the apparatus, and performing at least one blood treatment on the patient.

It is to be understood that both the foregoing general description and the following detailed description are exemplary and explanatory only and intended to provide a further explanation of the present invention, as claimed.

BRIEF DESCRIPTION OF THE DRAWINGS

FIG. 11A is a perspective view of a portable dialysate circuit adapter configured to engage with a BM or a portable module.

FIG. 11B is a top (plan) view of the adapter shown in FIG. 11A.

DETAILED DESCRIPTION OF THE PRESENT INVENTION

Figure 1A:
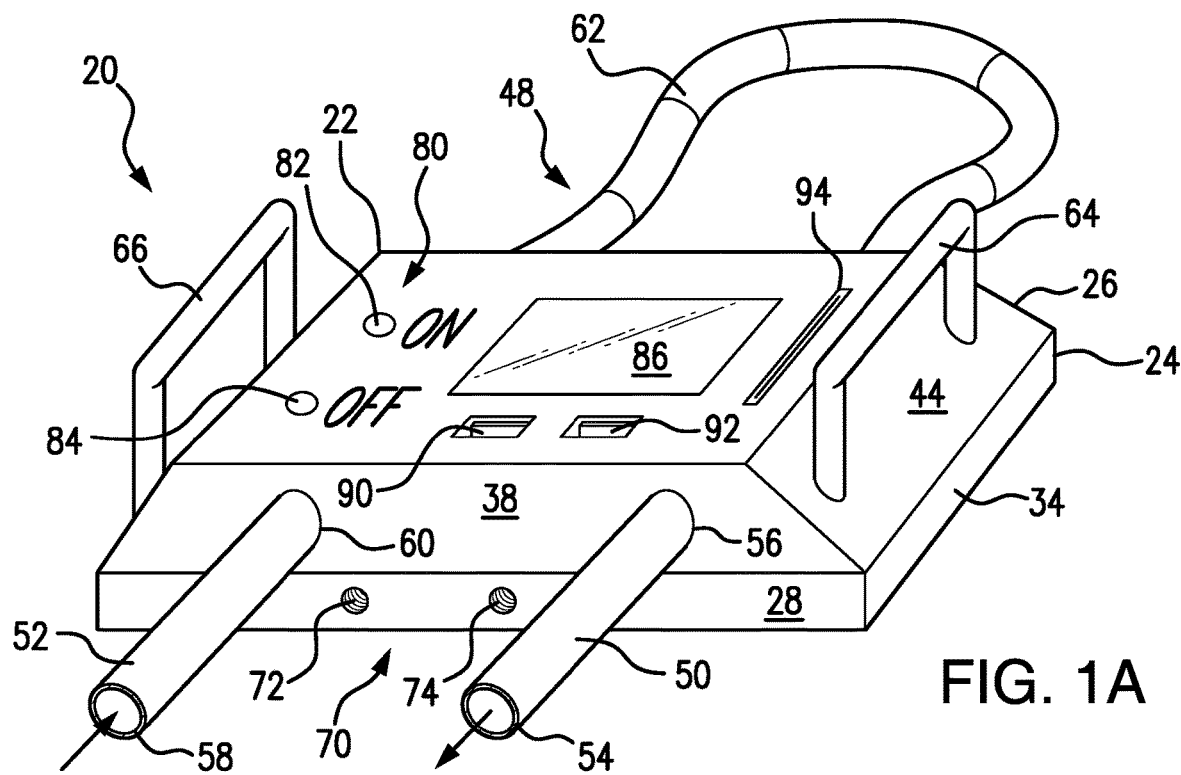
FIG. 1A is a perspective view of a portable blood circuit adapter configured to engage with a base module or a portable module.

The portable blood circuit adapter can comprise an extracorporeal blood circuit tubing set, an adapter housing, and a closure system. The extracorporeal blood circuit tubing set can comprise a to-patient venous line and a from-patient arterial line. Each of the venous line and arterial line can include an adapter end and a patient end and each patient end can include a needle for insertion into a patient's vascular access. A single needle or double needle system can be used. See, for example, U.S. Pat. Nos. 4,514,295; 4,702,829; 6,738,052; and 8,500,671, which are incorporated by reference herein in their entireties. The adapter housing can comprise a module connector configured to engage a complementary inter-module connector of a blood treatment apparatus, for example, a blood treatment apparatus that comprises a blood pump configured to pump blood extracorporeally through the extracorporeal blood circuit tubing set. The adapter housing can comprise tube connectors for fixing the adapter ends of the venous line and the arterial line to the adapter housing. The tube connectors can be in fluid communication with the module connector and can provide interruptible fluid flow paths between the venous line and the module connector and between the arterial line and the module connector. The closure system can be mounted in or on the adapter housing and can be configured to interrupt fluid communication between the venous line and the module connector and between the arterial line and the module connector, when the portable blood circuit adapter is disconnected from a blood treatment apparatus. The closure system can also be configured to provide fluid communication between the venous line and the module connector and between the arterial line and the module connector, when the portable blood circuit adapter is connected to a complementary inter-module connector of a blood treatment apparatus. The portable blood circuit adapter can also comprise an anticoagulant dispenser mounted in or on the adapter housing, for example, in fluid communication with the extracorporeal blood circuit tubing set. The portable blood circuit adapter can also comprise a user interface, for example, on, or connected to, the adapter housing.

The module connector can be configured to engage a complementary inter-module connector of a blood treatment (processing) apparatus or to engage many different blood treatment apparatuses. The engagement can comprise a snap-fit connection, a hook and loop combination connection, a latch, a lock, a press-fit connection, a friction-fit connection, a magnetic coupling connection, any combination thereof, or the like. For example, a snap-fit connection can be used as described in Bonenberger, "The First Snap-Fit Handbook," 2nd. ed., Hanser Publications, Inc., Cincinnati, Ohio, 2005, which is incorporated by reference herein in its entirety. A key and/or actuator-based mechanism can be used. A modular system is also provided comprising the portable blood circuit adapter and a portable blood processing module having an inter-module connector that is complementary to the module connector of the adapter housing. In an exemplary embodiment, the portable blood circuit adapter can be provided with a latch and the portable blood processing module can be provided with a catch designed to catch the latch. One of the two components can have a magnet and the other component can have a metal plate to which the magnet is attracted. Other complementary connections can instead, or also, be used.

The blood processing module can also comprise a module blood circuit including a to-patient line and a from-patient line. The to-patient line does not necessarily extend all the way to a patient, but can instead fluidly connect to a to-patient line of another extracorporeal blood circuit tubing set, for example, that is part of the portable blood circuit adapter. The blood processing module can also comprise a blood pump, wherein each of the to-patient line and the from-patient line of the module blood circuit has a connector end in fluid communication with the inter-module connector. The blood pump can be configured to circulate blood through the module blood circuit, through the extracorporeal blood circuit tubing set, and to and from a patient. The portable blood processing module can further comprise a dialysate circuit and a blood filter, and the blood filter can be in fluid communication with the module blood circuit and the dialysate circuit. The blood filter can comprise, for example, a dialyzer. The portable blood processing module can comprise a dialysate pump in operable communication with the dialysate circuit, a sorbent cartridge in fluid communication with the dialysate circuit, a heater in operable communication with the dialysate circuit, any combination thereof, or the like. The portable blood processing module can comprise a battery-powered power source.

A method is provided that uses a modular system comprising a portable blood circuit adapter as described herein and a portable blood processing module as described herein. The method can comprise connecting each of the needles of the patient ends of the venous line and the arterial line to vascular access points of a patient, engaging the portable blood circuit adapter with the portable blood processing module, and performing at least one blood treatment on the patient. The at least one blood treatment can comprise blood circulation, hemodialysis, hemofiltration, hemodiafiltration, apheresis, any combination thereof, or the like. The method can also comprise disengaging the portable blood circuit adapter from the portable blood processing module and then withdrawing the needles from the vascular access points.

An engagement verification subsystem can be provided that is configured to indicate that the portable blood circuit adapter is securely engaged with the portable blood processing module. The engagement verification subsystem can be configured to generate a first detectable signal when the portable blood circuit adapter is securely engaged with the portable blood processing module. A second detectable signal can be generated when the portable blood circuit adapter is disengaged from the portable blood processing module. Each of the first detectable signal and the second detectable signal can independently comprise a visual signal, an audible signal, a haptic signal, any combination thereof, or the like.

A modular system is also provided that comprises a portable blood circuit adapter as described herein, and a non-portable, first base module comprising an inter-module connector that is complementary to the module connector of the adapter housing. The first base module can comprise a base module blood circuit including a to-patient line and a from-patient line, a second blood pump, a dialysate pump, and a dialysate circuit. The second blood pump can be configured to circulate blood through the base module blood circuit, through the extracorporeal blood circuit tubing set, and to and from a patient. The dialysate circuit can comprise a blood filter in fluid communication with the base module blood circuit and the dialysate circuit. The blood filter can comprise, for example, a dialyzer. The dialysate circuit can further comprise a sorbent cartridge, a heater in operable communication with the dialysate circuit, a temperature sensor configured to sense the temperature of dialysate in the dialysate circuit, a conductivity sensor configured to sense the conductivity of dialysate in the dialysate circuit, a weighing subsystem configured to weigh dialysate in the dialysate circuit or to weigh dialysate in a reservoir that can be part of the dialysate circuit, or any combination thereof. An engagement verification subsystem can be provided and configured to indicate that the portable blood circuit adapter is securely engaged with the first base module. The engagement verification subsystem can be configured to generate a first detectable signal when the portable blood circuit adapter is securely engaged with the first base module, and a second detectable signal when the portable blood circuit adapter is disengaged from the first base module. Each of the first detectable signal and the second detectable signal can independently comprise a visual signal, an audible signal, a haptic signal, any combination thereof, or the like.

A method is also provided that uses a modular system as described herein. The method can comprise connecting each of the needles of the patient ends of the venous line and the arterial line to vascular access points of a patient, engaging the portable blood circuit adapter with the first base module, and performing at least one blood treatment on the patient. The at least one blood treatment can comprise blood circulation, hemodialysis, hemofiltration, hemodiafiltration, apheresis, any combination thereof, or the like. The method can further comprise disengaging the portable blood circuit adapter from the first base module and, without disconnecting the extracorporeal blood circuit tubing set from the patient, engaging the portable blood circuit adapter with a portable blood processing module. The portable blood processing module can be as described herein, and, for example, can comprise an inter-module connector that is complementary to the module connector of the adapter housing. The portable blood processing module can comprise a module blood circuit including a to-patient line and a from-patient line, and a first blood pump. Each of the to-patient line and the from-patient line of the module blood circuit can have a connector end in fluid communication with the inter-module connector. The blood pump can be configured to circulate blood through the module blood circuit, through the extracorporeal blood circuit tubing set, and to and from the patient. The method can also comprise disengaging the portable blood circuit adapter from the portable blood processing module, and reengaging the portable blood circuit adapter with the first base module, for example, without disconnecting the extracorporeal blood circuit tubing set from the patient. The at least one blood treatment can then be resumed. In some cases, the method can involve reengaging and then performing a different blood treatment on the patient compared to an original treatment that had been interrupted or stopped. The portable blood circuit adapter can be disengaged from a first base module, and then engaged with a second base module with which at least one blood treatment is performed on the patient, without ever disconnecting the patient from the extracorporeal blood tubing set of the adapter.

A modular system is also provided that comprises a portable blood circuit adapter as described herein, a base module comprising a dialysate circuit and a first dialysate pump in operative communication with the dialysate circuit, and a first remote module located remotely, for example, at least one foot away, at least five feet away, at least ten feet away, at least twenty feet away, at least fifty feet away, at least 100 feet away, or some other distance away from the base module. The first remote module can comprise a first blood pump, an inter-module connector that is complementary to the module connector of the adapter housing, and a local blood circuit in fluid communication with the inter-module connector. The first blood pump can be in operative communication with the local blood circuit. The dialysate circuit can extend from the base module to the first remote module. A first blood filter can also be provided, for example, in fluid communication with both the local blood circuit and the dialysate circuit. The first remote module can comprise a remote user interface and the base module can comprise a base module user interface. The first blood filter can comprise, for example, a dialyzer. The first remote module can comprise a fitting and the first blood filter can be mounted or otherwise secured in the fitting. The base module can comprise a sorbent cartridge fitting, a heater in operative thermal communication with the dialysate circuit, a reservoir, any combination thereof, or the like. The dialysate circuit can comprise a sorbent cartridge and the sorbent cartridge can be configured to be secured by the sorbent cartridge fitting, or vice versa. A second dialysate pump can be provided in operative communication with the dialysate circuit. The base module can further comprise a temperature sensor configured for sensing the temperature of dialysate in the dialysate circuit, a conductivity sensor configured for sensing the conductivity of dialysate in the dialysate circuit, a weighing subsystem configured for weighing dialysate, any combination thereof, or the like. The base module and the first remote module can be located in different rooms of a building, on different levels of a building, or in different buildings. A second remote module can also be included in the system and can be located remotely from the base module. The second remote module can comprise a second blood pump, a second inter-module connector that is complementary to the module connector of the adapter housing, and a second local blood circuit in fluid communication with the second inter-module connector. The second blood pump can be in operative communication with the second local blood circuit. The dialysate circuit can extend from the base module to the second remote module, for example, in parallel or in series with plumbing extending to the first remote location.

As with other systems described herein, modular systems comprising a portable blood circuit adapter, a base module, and one or more remote modules, can be provided with an engagement verification subsystem. The engagement verification subsystem can be configured to indicate whether or not the portable blood circuit adapter is securely engaged with either the first remote module or the second remote module. The engagement verification subsystem can be configured to generate a first detectable signal when the portable blood circuit adapter is securely engaged with the first remote module or the second remote module, and can independently be configured to generate a second detectable signal when the portable blood circuit adapter is disengaged from both the first remote module and the second remote module. Such modular systems can also comprise a remote module lockout subsystem configured to lock-out use of one remote module when the portable blood circuit adapter is engaged with another remote module. In an exemplary configuration, the subsystem can lock-out use of the first remote module when the portable blood circuit adapter is engaged with the second remote module, and vice versa.

The method can use a modular system that comprises a portable blood circuit adapter, a base module, and one or more remote modules. The method can comprise connecting each of the patient ends of the venous line and the arterial line, for example, via one or more needles, to vascular access points of a patient. Then, the portable blood circuit adapter can be engaged with the first remote module and at least one blood treatment can be performed on the patient. The at least one blood treatment can comprise blood circulation, hemodialysis, hemofiltration, hemodiafiltration, apheresis, any combination thereof, or the like. The method can use a modular system that includes at least first and second remote modules, and the method can involve connecting a venous line and an arterial line to vascular access points of a patient, engaging the portable blood circuit adapter with the first remote module, performing at least one blood treatment on the patient, disengaging the portable blood circuit adapter from the first remote module, and engaging the portable blood circuit adapter with the second remote module without disconnecting the extracorporeal blood circuit tubing set from the patient.

The modular system can comprise a first base module and a first portable module. The first base module can comprise a dock and can be configured to dock the first portable module. The first portable module can be, for example, a portable extracorporeal blood circuit module. The first base module can comprise a base module housing and a primary dialysate circuit comprising a primary dialysate pump, a primary dialysate line, and a first inter-module connector. The first portable module can be configured to dock to the first base module and operate in a docked configuration, and can be configured to operate independently of the first base module in an undocked configuration. The first portable module can comprise a first portable module housing, a blood pump mounted in or on the first portable module housing, a first extracorporeal blood circuit tubing set, and a second inter-module connector, complementary to the first inter-module connector, and configured to connect to the first inter-module connector in the docked configuration. The blood pump can be configured to releasably engage the extracorporeal blood circuit tubing set and the tubing set can be disposable and replaceable. The primary dialysate circuit can further comprise a blood filter in fluid communication with the primary dialysate line and the first inter-module connector can be in fluid communication with the blood filter, in which case the second inter-module connector can be in fluid communication with the extracorporeal blood circuit tubing set. The blood filter can comprise, for example, a dialyzer. The primary dialysate circuit can further comprise a primary heater, a sorbent cartridge, any combination thereof, or the like. The primary dialysate circuit can further comprise a temperature sensor configured for sensing a temperature of dialysate in the dialysate circuit, a conductivity sensor configured for sensing a conductivity of dialysate in the dialysate circuit, a weighing subsystem configured for weighing dialysate in the dialysate circuit, a secondary heater, any combination thereof, or the like. The first base module can comprise a primary user interface, and the first portable module can comprise a secondary user interface. The modular system can also comprise a central control subsystem including a central control user interface configured to control the first portable module. The modular system can comprise a mobile communications device including a mobile communications device user interface, and can be configured to control the first portable module.

The extracorporeal blood circuit tubing set can comprise a blood filter, and the blood filter can comprise a membrane that separates the blood filter into a blood side of the blood filter and a dialysate side of the blood filter. The dialysate side of the blood filter can be in fluid communication with the second inter-module connector, and the primary dialysate line can be in fluid communication with the first inter-module connector. The extracorporeal blood circuit tubing set can comprise an arterial line, the blood filter, and a venous line, and both the arterial line and the venous line can be in fluid communication with the blood side of the blood filter. The blood filter can be, for example, a dialyzer.

The first portable module housing can be configured to engage the base module housing at an interface between the first and second inter-module connectors. The first base module housing can comprise a receptacle at least partially defining the first inter-module connector and being configured to receive and secure at least a portion of the first portable module housing, for example, including the second inter-module connector. The connection between the two modules can comprise a hook and loop combination connector, a latch, a lock, a snap-fit connector, a frictional engagement, a magnetic coupling connector, any combination thereof, or the like. The first portable module can comprise a cart, a set of wheels, a wheeled bag, a belt, a waist pack, a neck strap, a shoulder strap, a shoulder harness, a backpack, a chest pack, any combination thereof, or the like. The first inter-module connector can comprise one or more valves, hatches, or other closures that are configured to be in an open state in the docked configuration and to be in a closed state in the undocked configuration. The closures can be configured such that when a portable module is disengaged from a base module the closures shut, preventing any blood, dialysate, or both, from escaping through the second inter-module connector. A similar configuration, or the same configuration of closures, can be used for the first inter-module connector. The extracorporeal blood circuit tubing set used with such a system can comprise a blood filter. The blood filter can comprise a membrane that separates the blood filter into a blood side of the blood filter and a dialysate side of the blood filter. The first portable module can comprise a secondary dialysate circuit comprising a secondary dialysate pump, and the secondary dialysate circuit can be in fluid communication with the dialysate side of the blood filter. The second inter-module connector can be in fluid communication with a fresh dialysate reservoir and a spent dialysate reservoir, and the secondary dialysate pump can be located along the secondary dialysate circuit between the dialyzer and a jug of fresh dialysate.

The first inter-module connector can further comprise a first electrical connector and the second inter-module connector can comprise a second electrical connector that is complementary to the first electrical connector. The first portable module can further comprise a battery-operated auxiliary power source. As such, the first portable module can be powered by the base module when docked, and powered by its own battery when undocked. An engagement verification subsystem can be provided and can be configured to generate a detectable signal when the first portable module is securely engaged with the first base module. The detectable signal can comprise a visual signal, an audible signal, a haptic signal, any combination thereof, or the like. The engagement verification subsystem can be configured to generate a second detectable signal when the first portable module is disengaged from the first base module. The second detectable signal can comprise a visual signal, an audible signal, a haptic signal, any combination thereof, or the like.

A second portable module can also be provided, and, like the first portable module, can be configured to dock with the first base module in a docked configuration. The second portable module can be configured to operate independently of the first base module, in an undocked configuration. The second portable module can comprise a second portable module housing, a second blood pump mounted in or on the second portable module housing, a second extracorporeal blood circuit tubing set, and a third inter-module connector that is complementary to the first inter-module connector and configured to connect to the first inter-module connector. The second blood pump can be configured to releasably engage the second extracorporeal blood circuit tubing set. The third portable module differs from the second portable module and is configured to perform a different blood treatment on a patient than the treatment for which the second portable module is configured.

The modular system can comprise the first base module, the first portable module, and a second base module comprising a dock configured to dock the first portable module. The first and second base modules can be located in different respective rooms of a building, on different respective levels of a building, or in different respective buildings. One or both of the first and second base modules can be permanently installed, for example, plumbed, into different respective rooms of a building, into different respective levels of a building, or into different respective buildings. The second base module can comprise one or more of the same attributes, features, aspects, structure, and functions of the first base module. The second base module can comprise a dock and can be configured to dock the first portable module. The second base module can comprise a base module housing, a primary dialysate circuit comprising a primary dialysate pump, a primary dialysate line, and its own inter-module connector. The second base module can comprise a primary user interface, and the first portable module can comprise a secondary user interface. The modular system can also comprise a central control subsystem including a central control user interface configured to control the first portable module. The modular system can comprise a mobile communications device including a mobile communications device user interface and can be configured to control the first portable module. The second base module can differ from the first base module and the first and second base modules can be configured to perform the same or different blood treatments with respect to one another.

A method is provided that comprises connecting a patient to a first extracorporeal blood circuit tubing set that is part of a first portable module, engaging the first portable module with a first base module, and performing at least one blood treatment on the patient. The treatment can comprise blood circulation, hemodialysis, hemofiltration, hemodiafiltration, apheresis, any combination thereof, or the like. The method can further comprise disengaging the first portable module from the first base module and engaging a second portable module with the first base module. In some cases, the first portable module can be disengaged from the first base module, the patient can then move with the first portable module connected to the patient through the extracorporeal blood circuit tubing set, and the first portable module can be engaged with a second base module. The second base module can be located remotely relative to the first base module, for example, at least five feet away, at least ten feet away, at least fifty feet away, at least one hundred feet away, or at some other distance away from the first base module. The first portable module can then be dis-engaged from the first base module while the patient remains connected to the first extracorporeal blood circuit tubing set, and the first portable module can then be engaged with a second base module. During the switching of positions, the patient can remain connected to the first extracorporeal blood circuit tubing set. A second blood treatment can then be performed on the patient, for example, a treatment comprising blood circulation, hemodialysis, hemofiltration, hemodiafiltration, apheresis, any combination thereof, or the like. The method can also comprise disengaging the first portable module from the first base module and performing at least one blood treatment on the patient, using the first portable module, independent of the first or any other base module. The at least one blood treatment can comprise blood circulation, hemodialysis, hemofiltration, hemodiafiltration, apheresis, any combination thereof, or the like.

The method can comprise connecting a patient to a first extracorporeal blood circuit tubing set, performing at least one blood treatment on the patient, using a first portable module independent of a first base module, then, without disconnecting the patient from the first extracorporeal blood circuit tubing set, engaging the first portable module with the first base module. At least one blood treatment can then be performed on the patient while the first portable module is engaged with or docked to the first base module.

A portable blood circulation unit for an extracorporeal blood circuit is also provided. The portable blood circulation unit comprises a housing configured to engage a blood treatment apparatus, and a unit blood pump mounted in or on the housing and configured to releasably engage, and circulate blood through, an extracorporeal short circuit blood circuit. A battery-powered power source can be configured to power the unit blood pump. An extracorporeal short circuit blood circuit can be provided that is releasably engaged with the unit blood pump. The portable blood circulation unit can also include a first inter-module connector.

The blood treatment apparatus can comprise a blood pump configured to pump blood from and to a patient extracorporeally through an extracorporeal blood circuit. The extracorporeal short circuit blood circuit and the housing can together be configured to provide a bypass mode of operation wherein the portable blood circulation unit is not engaged with a blood treatment apparatus and blood is circulated to and from the patient, through the extracorporeal short circuit blood circuit, independent of a blood treatment apparatus. The first inter-module connector can be configured to connect the portable blood circulation unit to a blood treatment apparatus and form a fluid communication between the extracorporeal short circuit blood circuit and a base module blood circuit of the blood treatment apparatus.

A combination comprising the portable blood circulation unit and a blood treatment apparatus is also provided. In the combination, the blood treatment apparatus can comprise a base module blood circuit and a second inter-module connector complementary to, and configured to connect to, an inter-module connector of the blood treatment apparatus. The inter-module connectors can connect with one another to connect the portable blood circulation unit to the blood treatment apparatus, and to form a fluid communication between the extracorporeal short circuit blood circuit and the base module blood circuit. The first and second inter-module connectors can be configured such that, when connected, a full blood circulation mode of operation is provided wherein blood is circulated to and from the patient, through the extracorporeal short circuit blood circuit, and through the base module blood circuit.

In use, a method is provided that can comprise connecting a patient to a extracorporeal short circuit blood circuit, engaging the first inter-module connector to a blood treatment apparatus having a complementary second inter-module connector, disengaging the portable blood circulation unit from the blood treatment apparatus, and then either (i) engaging the first inter-module connector with a second blood treatment apparatus, or (ii) reengaging the first inter-module connector with the blood treatment apparatus.

A portable blood circulation adapter is provided that can comprise an adapter housing configured to alternatively engage respective apparatus housings of at least two different blood treatment apparatuses, with each apparatus comprising a respective blood pump configured to pump blood extracorporeally. The blood circulation adapter can also comprise an extracorporeal blood circuit attached to the adapter housing. The extracorporeal blood circuit can be configured to alternatively engage the respective blood pumps. The extracorporeal blood circuit can comprise an arterial blood line, a blood venous line, and a blood filter all in fluid communication with one another. The blood filter can be configured for fluid communication alternatively with respective dialysate circuits in the at least two different blood treatment apparatuses. The blood filter can be, for example, a dialyzer.

The blood circulation adapter can further comprise a closure system configured to (i) interrupt fluid communication between the blood filter and the respective dialysate circuits when the blood circulation adapter is disengaged from the respective blood treatment apparatuses, and (ii) provide fluid communication between the blood filter and the respective dialysate circuits when the blood circulation adapter is engaged with a blood treatment apparatus. The closure system can comprise, for example, a first valve set comprising a first plurality of valves configured to alternatively provide fluid communication between the blood filter and the respective dialysate circuits when the blood circulation adapter is engaged with one of the respective blood treatment apparatuses. A blood circulation adapter that is configured for fluid communication of dialysate flow, instead of blood flow, can instead be used and can include or share one or more components of an adapter configured for fluid communication of blood flow. Thus, both "blood-side" and "dialysate-side" adapters are part of the present invention. A given adapter can be configured to communicate fluidically with a blood treatment apparatus through an extracorporeal blood circuit, a dialysate circuit, or both. An adapter can be dedicated as a blood-side or dialysate side adapter, or be convertible between the two.

Methods of using, and systems comprising, the blood circulation adapter are also provided. A modular system is provided that can comprise a blood circulation adapter further comprising an adapter dialysate circuit and a blood filter in fluid communication with the extracorporeal blood circuit and the adapter dialysis circuit. The adapter dialysate circuit can include, for example, at least the dialysate side of a dialyzer. The modular system can also comprise a blood treatment apparatus comprising a blood pump and an apparatus dialysate circuit. The apparatus can be configured to engage the blood circulation adapter and to perform at least one blood treatment on a patient. The modular system can further include a closure system configured to provide fluid communication between the adapter dialysate circuit and the apparatus dialysate circuit. The modular system can include one or more additional blood processing apparatuses that can engage the blood circulation adapter. The apparatuses of the modular system can be of the same, similar, or differing designs, but can still be capable of engaging the blood circulation adapter in a universal fashion. For example, the apparatuses can differ in their blood processing configurations, functionalities, portabilities, combinations thereof, or the like. Herein, by universal, what is meant is as that an apparatus is not restricted in its use or compatibility with other apparatuses, adapters, and modules as described herein. An apparatus is universal if it can be used with more than a single type of adapter. For example, an interface can be said to be universal if it can engage with a portable adapter, a cleaning adapter, and a priming adapter, or with another combination of different components.

A method is provided that can include providing the modular system; connecting the extracorporeal blood circuit to a patient; engaging the portable blood circuit adapter with the blood treatment apparatus; opening the closure system to provide fluid communication of dialysate between the blood circulation adapter and the apparatus; and performing at least one blood treatment on the patient. The method can also comprise interrupting the treatment and disengaging the adapter from the apparatus without disconnecting the adapter from the patient. The method can further comprise reengaging the adapter with the same apparatus or engaging the adapter with a different apparatus, and resuming the same treatment or beginning a different treatment, also without disconnecting the adapter from the patient. The adapter can be engaged to an intermediate apparatus for transport between two different blood treatment apparatuses. The intermediate apparatus can simply maintain circulation of blood in the extracorporeal blood circuit or can be configured with greater functionality.

The portable blood circuit adapter can comprise an extracorporeal blood circuit tubing set, an adapter housing, and a closure system. The extracorporeal blood circuit tubing set can comprise a venous line and an arterial line. Each of the venous line and arterial line can include an adapter end and a patient end and each patient end can include a needle for insertion into a patient's vascular access. A single needle or double needle system can be used. See, for example, U.S. Pat. Nos. 4,514,295; 4,702,829; 6,738,052; and 8,500,671, which are incorporated by reference herein in their entireties. The adapter housing can comprise a module connector configured to engage a complementary inter-module connector of a blood treatment apparatus, for example, a blood treatment apparatus that comprises a blood pump configured to pump blood extracorporeally through the extracorporeal blood circuit tubing set. The adapter housing can comprise tube connectors for fixing the adapter ends of the venous line and the arterial line to the adapter housing. The tube connectors can be in fluid communication with the module connector and can provide interruptible fluid flow paths between the venous line and the module connector and between the arterial line and the module connector. The closure system can be mounted in or on the adapter housing and can be configured to interrupt fluid communication between the venous line and the module connector and between the arterial line and the module connector when the portable blood circuit adapter is disconnected from a blood treatment apparatus. The closure system can also be configured to provide fluid communication between the venous line and the module connector and between the arterial line and the module connector when the portable blood circuit adapter is connected to a complementary inter-module connector of a blood treatment apparatus. The portable blood circuit adapter can also comprise an anticoagulant dispenser mounted in or on the adapter housing, for example, in fluid communication with the extracorporeal blood circuit tubing set. The portable blood circuit adapter can also comprise a user interface, for example, on, or connected to, the adapter housing.

The module connector can be configured to engage a complementary inter-module connector of a blood treatment (processing) apparatus or to engage many different blood treatment apparatuses. The engagement can comprise a snap-fit connection, a hook, and loop combination connection, a latch, a lock, a press-fit connection, a friction-fit connection, a magnetic coupling connection, any combination thereof, or the like. For example, a snap-fit connection can be used as described in Bonenberger, "The First Snap-Fit Handbook," 2nd. ed., Hanser Publications, Inc., Cincinnati, Ohio, 2005, which is incorporated by reference herein in its entirety. A key and/or actuator-based mechanism can be used. A modular system is also provided comprising the portable blood circuit adapter and a portable blood processing module having an inter-module connector that is complementary to the module connector of the adapter housing. In an exemplary embodiment, the portable blood circuit adapter can be provided with a latch and the portable blood processing module can be provided with a catch designed to catch the latch. One of the two components can have a magnet, and the other component can have a metal plate to which the magnet is attracted. Other complementary connections can instead, or also, be used.

The portable blood processing module can also comprise a module blood circuit including a to-patient line and a from-patient line. The to-patient line does not necessarily extend all the way to a patient, but can instead fluidly connect to a to-patient line of another extracorporeal blood circuit tubing set, for example, that is part of the portable blood circuit adapter. The portable blood processing module can also comprise a blood pump, wherein each of the to-patient line and the from-patient line of the module blood circuit has a connector end in fluid communication with the inter-module connector. The blood pump can be configured to circulate blood through the module blood circuit, through the extracorporeal blood circuit tubing set, and to and from a patient. The portable blood processing module can further comprise a dialysate circuit and a blood filter, and the blood filter can be in fluid communication with the module blood circuit and the dialysate circuit. The blood filter can comprise, for example, a dialyzer. The portable blood processing module can comprise a dialysate pump in operable communication with the dialysate circuit, a sorbent cartridge in fluid communication with the dialysate circuit, a heater in operable communication with the dialysate circuit, any combination thereof, or the like. The portable blood processing module can comprise a battery-powered power source.

A method is provided that uses a modular system comprising a portable blood circuit adapter as described herein and a portable blood processing module as described herein. The method can comprise connecting each of the needles of the patient ends of the venous line and the arterial line to vascular access points of a patient, engaging the portable blood circuit adapter with the portable blood processing module, and performing at least one blood treatment on the patient. The at least one blood treatment can comprise blood circulation, hemodialysis, hemofiltration, hemodiafiltration, apheresis, any combination thereof, or the like. The method can also comprise disengaging the portable blood circuit adapter from the portable blood processing module and then withdrawing the needles from the vascular access points.

An engagement verification subsystem can be provided that is configured to indicate that the portable blood circuit adapter is securely engaged with the portable blood processing module. The engagement verification subsystem can be configured to generate a first detectable signal when the portable blood circuit adapter is securely engaged with the portable blood processing module. A second detectable signal can be generated when the portable blood circuit adapter is disengaged from the portable blood processing module. Each of the first detectable signal and the second detectable signal can independently comprise a visual signal, an audible signal, a haptic signal, any combination thereof, or the like.

A modular system is also provided that comprises a portable blood circuit adapter as described herein, and a non-portable first base module ("BM") comprising an inter-module connector that is complementary to the module connector of the adapter housing. The first base module can comprise a base module blood circuit including a to-patient line and a from-patient line, a second blood pump, a dialysate pump, and a dialysate circuit. The second blood pump can be configured to circulate blood through the base module blood circuit, through the extracorporeal blood circuit tubing set, and to and from a patient. The dialysate circuit can comprise a blood filter in fluid communication with the base module blood circuit and the dialysate circuit. The blood filter can comprise, for example, a dialyzer. The dialysate circuit can further comprise a sorbent cartridge, a heater in operable communication with the dialysate circuit, a temperature sensor configured to sense the temperature of dialysate in the dialysate circuit, a conductivity sensor configured to sense the conductivity of dialysate in the dialysate circuit, a weighing subsystem configured to weigh dialysate in the dialysate circuit or to weigh dialysate in a reservoir that can be part of the dialysate circuit, or any combination thereof. An engagement verification subsystem can be provided and configured to indicate that the portable blood circuit adapter is securely engaged with the first base module. The engagement verification subsystem can be configured to generate a first detectable signal when the portable blood circuit adapter is securely engaged with the first base module, and a second detectable signal when the portable blood circuit adapter is disengaged from the first base module. Each of the first detectable signal and the second detectable signal can independently comprise a visual signal, an audible signal, a haptic signal, any combination thereof, or the like.

A method is also provided that uses a modular system as described herein. The method can comprise connecting each of the needles of the patient ends of the venous line and the arterial line to vascular access points of a patient, engaging the portable blood circuit adapter with the first base module, and performing at least one blood treatment on the patient. The at least one blood treatment can comprise blood circulation, hemodialysis, hemofiltration, hemodiafiltration, apheresis, any combination thereof, or the like. The method can further comprise disengaging the portable blood circuit adapter from the first base module and, without disconnecting the extracorporeal blood circuit tubing set from the patient, engaging the portable blood circuit adapter with a portable blood processing module. The portable blood processing module can be as described herein, and, for example, can comprise an inter-module connector that is complementary to the module connector of the adapter housing. The portable blood processing module can comprise a module blood circuit including a patient line and a from-patient line, and a first blood pump. Each of the to-patient line and the from-patient line of the module blood circuit can have a connector end in fluid communication with the inter-module connector. The blood pump can be configured to circulate blood through the module blood circuit, through the extracorporeal blood circuit tubing set, and to and from the patient. The method can also comprise disengaging the portable blood circuit adapter from the portable blood processing module, and reengaging the portable blood circuit adapter with the first base module, for example, without disconnecting the extracorporeal blood circuit tubing set from the patient. The at least one blood treatment can be resumed. In some cases, the method can involve reengaging and then performing a different blood treatment on the patient compared to an original treatment that had been interrupted or stopped. The portable blood circuit adapter can be disengaged from a first base module, and then engaged with a second base module with which at least one blood treatment is performed on the patient, without ever disconnecting the patient from the extracorporeal blood tubing set of the adapter.

A modular system is also provided that comprises a portable blood circuit adapter as described herein, a base module comprising a dialysate circuit and a first dialysate pump in operative communication with the dialysate circuit, and a first remote module located away from the base module (e.g., at least one foot away, at least five feet away, at least ten feet away, at least twenty feet away, at least fifty feet away, at least 100 feet away, or some other distance away from the base module). The first remote module can comprise a first blood pump, an inter-module connector that is complementary to the module connector of the adapter housing, and a local blood circuit in fluid communication with the inter-module connector. The first blood pump can be in operative communication with the local blood circuit. The dialysate circuit can extend from the base module to the first remote module. A first blood filter can also be provided, for example, in fluid communication with both the local blood circuit and the dialysate circuit. The first remote module can comprise a remote user interface, and the base module can comprise a base module user interface. The first blood filter can comprise, for example, a dialyzer. The first remote module can comprise a fitting, and the first blood filter can be mounted or otherwise secured in the fitting. The base module can comprise a sorbent cartridge fitting, a heater in operative thermal communication with the dialysate circuit, a reservoir, any combination thereof, or the like. The dialysate circuit can comprise a sorbent cartridge and the sorbent cartridge can be configured to be secured by the sorbent cartridge fitting, or vice versa. A second dialysate pump can be provided in operative communication with the dialysate circuit. The base module can further comprise a temperature sensor configured for sensing the temperature of dialysate in the dialysate circuit, a conductivity sensor configured for sensing the conductivity of dialysate in the dialysate circuit, a weighing subsystem configured for weighing dialysate, any combination thereof, or the like. The base module and the first remote module can be located in different rooms of a building, on different levels of a building, or in different buildings. A second remote module can also be included in the system and can be located remotely from the base module. The second remote module can comprise a second blood pump, a second inter-module connector that is complementary to the module connector of the adapter housing, and a second local blood circuit in fluid communication with the second inter-module connector. The second blood pump can be in operative communication with the second local blood circuit. The dialysate circuit can extend from the base module to the second remote module, for example, in parallel or in series with plumbing extending to the first remote location.

As with other systems described herein, modular systems comprising a portable blood circuit adapter, a base module, and one or more remote modules can be provided with an engagement verification subsystem. The engagement verification subsystem can be configured to indicate whether or not the portable blood circuit adapter is securely engaged with either the first remote module or the second remote module. The engagement verification subsystem can be configured to generate a first detectable signal when the portable blood circuit adapter is securely engaged with the first remote module or the second remote module, and can independently be configured to generate a second detectable signal when the portable blood circuit adapter is disengaged from both the first remote module and the second remote module. Such modular systems can also comprise a remote module lockout subsystem configured to lock-out use of one remote module when the portable blood circuit adapter is engaged with another remote module. In an exemplary configuration, the subsystem can lock-out use of the first remote module when the portable blood circuit adapter is engaged with the second remote module, and vice versa.

The method can use a modular system that comprises a portable blood circuit adapter, a base module, and one or more remote modules. The method can comprise connecting each of the patient ends of the venous line and the arterial line, for example, via one or more needles, to vascular access points of a patient. Then, the portable blood circuit adapter can be engaged with the first remote module and at least one blood treatment can be performed on the patient.

The at least one blood treatment can comprise blood circulation, hemodialysis, hemofiltration, hemodiafiltration, apheresis, any combination thereof, or the like. The method can use a modular system that includes at least first and second remote modules, and the method can involve connecting a venous line and an arterial line to vascular access points of a patient, engaging the portable blood circuit adapter with the first remote module, performing at least one blood treatment on the patient, disengaging the portable blood circuit adapter from the first remote module, and engaging the portable blood circuit adapter with the second remote module without disconnecting the extracorporeal blood circuit tubing set from the patient.

The modular system can comprise a first base module and a first portable module. The first base module can comprise a dock and can be configured to dock the first portable module. The first portable module can be, for example, a portable extracorporeal blood circuit module. The first base module can comprise a base module housing and a primary dialysate circuit comprising a primary dialysate pump, a primary dialysate line, and a first inter-module connector. The first portable module can be configured to dock to the first base module and operate in a docked configuration and can be configured to operate independently of the first base module in an undocked configuration. The first portable module can comprise a first portable module housing, a blood pump mounted in or on the first portable module housing, a first extracorporeal blood circuit tubing set, and a second inter-module connector, a complementary to the first inter-module connector, and configured to connect to the first inter-module connector in the docked configuration. The blood pump can be configured to releasably engage the extracorporeal blood circuit tubing set, and the tubing set can be disposable and replaceable. The primary dialysate circuit can further comprise a blood filter in fluid communication with the primary dialysate line, and the first inter-module connector can be in fluid communication with the blood filter, in which case the second inter-module connector can be in fluid communication with the extracorporeal blood circuit tubing set. The blood filter can comprise, for example, a dialyzer. The primary dialysate circuit can further comprise a primary heater, a sorbent cartridge, any combination thereof, or the like. The primary dialysate circuit can further comprise a temperature sensor configured for sensing a temperature of dialysate in the dialysate circuit, a conductivity sensor configured for sensing a conductivity of dialysate in the dialysate circuit, a weighing subsystem configured for weighing dialysate in the dialysate circuit, a secondary heater, any combination thereof, or the like. The first base module can comprise a primary user interface, and the first portable module can comprise a secondary user interface. The modular system can also comprise a central control subsystem including a central control user interface configured to control the first portable module. The modular system can comprise a mobile communications device including a mobile communications device user interface and can be configured to control the first portable module.

The extracorporeal blood circuit tubing set can comprise a blood filter, and the blood filter can comprise a membrane that separates the blood filter into a blood side of the blood filter and a dialysate side of the blood filter. The dialysate side of the blood filter can be in fluid communication with the second inter-module connector, and the primary dialysate line can be in fluid communication with the first inter-module connector. The extracorporeal blood circuit tubing set can comprise an arterial line, the blood filter, and a venous line, and both the arterial line and the venous line can be in fluid communication with the blood side of the blood filter. The blood filter can be, for example, a dialyzer.

The first portable module housing can be configured to engage the base module housing at an interface between the first and second inter-module connectors. The first base module housing can comprise a receptacle at least partially defining the first inter-module connector and being configured to receive and secure at least a portion of the first portable module housing, for example, including the second inter-module connector. The connection between the two modules can comprise a hook and loop combination connector, a latch, a lock, a snap-fit connector, a frictional engagement, a magnetic coupling connector, any combination thereof, or the like. The first portable module can comprise a cart, a set of wheels, a wheeled bag, a belt, a waist pack, a neck strap, a shoulder strap, a shoulder harness, a backpack, a chest pack, any combination thereof, or the like. The first inter-module connector can comprise one or more valves, hatches, or other closures that are configured to be in an open state in the docked configuration and to be in a closed state in the undocked configuration. The closures can be configured such that when a portable module is disengaged from a base module, the closures shut thereby preventing any blood, dialysate, or both, from escaping through the second inter-module connector. A similar configuration, or the same configuration of closures, can be used for the first inter-module connector. The extracorporeal blood circuit tubing set used with such a system can comprise a blood filter. The blood filter can comprise a membrane that separates the blood filter into a blood side of the blood filter and a dialysate side of the blood filter. The first portable module can comprise a secondary dialysate circuit comprising a secondary dialysate pump, and the secondary dialysate circuit can be in fluid communication with the dialysate side of the blood filter. The second inter-module connector can be in fluid communication with a fresh dialysate reservoir and a spent dialysate reservoir, and the secondary dialysate pump can be located along the secondary dialysate circuit between the dialyzer and a jug of fresh dialysate.

The first inter-module connector can further comprise a first electrical connector and the second inter-module connector can comprise a second electrical connector that is complementary to the first electrical connector. The first portable module can further comprise a battery-operated auxiliary power source. As such, the first portable module can be powered by the base module when docked, and powered by its battery when undocked. An engagement verification subsystem can be provided and can be configured to generate a detectable signal when the first portable module is securely engaged with the first base module. The detectable signal can comprise a visual signal, an audible signal, a haptic signal, any combination thereof, or the like. The engagement verification subsystem can be configured to generate a second detectable signal when the first portable module is disengaged from the first base module. The second detectable signal can comprise a visual signal, an audible signal, a haptic signal, any combination thereof, or the like.

A second portable module can also be provided, and, like the first portable module, can be configured to dock with the first base module in a docked configuration. The second portable module can be configured to operate independently of the first base module, in an undocked configuration. The second portable module can comprise a second portable module housing, a second blood pump mounted in or on the second portable module housing, a second extracorporeal blood circuit tubing set, and a third inter-module connector that is complementary to the first inter-module connector and configured to connect to the first inter-module connector. The second blood pump can be configured to releasably engage the second extracorporeal blood circuit tubing set. The third portable module differs from the second portable module and is configured to perform a different blood treatment on a patient than treatment for which the second portable module is configured.

The modular system can comprise the first base module, the first portable module, and a second base module comprising a dock configured to dock the first portable module. The first and second base modules can be located in different respective rooms of a building, on different respective levels of a building, or in different respective buildings. One or both of the first and second base modules can be permanently installed, for example, plumbed, into different respective rooms of a building, into different respective levels of a building, or into different respective buildings. The second base module can comprise one or more of the same attributes, features, aspects, structure, and functions of the first base module. The second base module can comprise a dock and can be configured to dock the first portable module. The second base module can comprise a base module housing, a primary dialysate circuit comprising a primary dialysate pump, a primary dialysate line, and its inter-module connector. The second base module can comprise a primary user interface, and the first portable module can comprise a secondary user interface. The modular system can also comprise a central control subsystem including a central control user interface configured to control the first portable module. The modular system can comprise a mobile communications device including a mobile communications device user interface and can be configured to control the first portable module. The second base module can differ from the first base module and the first and second base modules can be configured to perform the same or different blood treatments with respect to one another.

A method is provided that comprises connecting a patient to a first extracorporeal blood circuit tubing set that is part of a first portable module, engaging the first portable module with a first base module, and performing at least one blood treatment on the patient. The treatment can comprise blood circulation, hemodialysis, hemofiltration, hemodiafiltration, apheresis, any combination thereof, or the like. The method can further comprise disengaging the first portable module from the first base module and engaging a second portable module with the first base module. In some cases, the first portable module can be disengaged from the first base module, the patient can move with the first portable module connected to the patient through the extracorporeal blood circuit tubing set, and the first portable module can be engaged with a second base module. The second base module can be located remotely relative to the first base module, for example, at least five feet away, at least ten feet away, at least fifty feet away, at least one hundred feet away, or at some other distance away from the first base module. The first portable module can be disengaged from the first base module while the patient remains connected to the first extracorporeal blood circuit tubing set, and the first portable module can be engaged with a second base module. During the switching of positions, the patient can remain connected to the first extracorporeal blood circuit tubing set. A second blood treatment can be performed on the patient, for example, a treatment comprising blood circulation, hemodialysis, hemofiltration, hemodiafiltration, apheresis, any combination thereof, or the like. The method can also comprise disengaging the first portable module from the first base module and performing at least one blood treatment on the patient, using the first portable module, independent of the first or any other base module. The at least one blood treatment can comprise blood circulation, hemodialysis, hemofiltration, hemodiafiltration, apheresis, any combination thereof, or the like.

The method can comprise connecting a patient to a first extracorporeal blood circuit tubing set, performing at least one blood treatment on the patient, using a first portable module independent of a first base module, then, without disconnecting the patient from the first extracorporeal blood circuit tubing set, engaging the first portable module with the first base module. At least one blood treatment can be performed on the patient while the first portable module is engaged with or docked to the first base module.

A portable blood circulation unit for an extracorporeal blood circuit is also provided. The portable blood circulation unit comprises a housing configured to engage a blood treatment apparatus, and a unit blood pump mounted in or on the housing and configured to engage releasably, and circulate blood through, an extracorporeal short circuit blood circuit. A battery-powered power source can be configured to power the unit blood pump. An extracorporeal short circuit blood circuit can be provided that is releasably engaged with the unit blood pump. The portable blood circulation unit can also include a first inter-module connector.

The blood treatment apparatus can comprise a blood pump configured to pump blood from and to a patient extracorporeally through an extracorporeal blood circuit. The extracorporeal short circuit blood circuit and the housing can together be configured to provide a bypass mode of operation wherein the portable blood circulation unit is not engaged with a blood treatment apparatus and blood is circulated to and from the patient, through the extracorporeal short circuit blood circuit, independent of a blood treatment apparatus. The first inter-module connector can be configured to connect the portable blood circulation unit to a blood treatment apparatus and form a fluid communication between the extracorporeal short circuit blood circuit and a base module blood circuit of the blood treatment apparatus.

A combination comprising the portable blood circulation unit and a blood treatment apparatus is also provided. In the combination, the blood treatment apparatus can comprise a base module blood circuit and a second inter-module connector complementary to, and configured to connect to, an inter-module connector of the blood treatment apparatus. The inter-module connectors can connect with one another to connect the portable blood circulation unit to the blood treatment apparatus, and to form a fluid communication between the extracorporeal short circuit blood circuit and the base module blood circuit. The first and second inter-module connectors can be configured such that, when connected, a full blood circulation mode of operation is provided wherein blood is circulated to and from the patient, through the extracorporeal short circuit blood circuit, and through the base module blood circuit.

In use, a method is provided that can comprise connecting a patient to an extracorporeal short circuit blood circuit, engaging the first inter-module connector to a blood treatment apparatus having a complementary second inter-module connector, disengaging the portable blood circulation unit from the blood treatment apparatus, and then either (i) engaging the first inter-module connector with a second blood treatment apparatus, or (ii) reengaging the first inter-module connector with the blood treatment apparatus.

A portable blood circulation adapter is provided that can comprise an adapter housing configured to alternatively engage respective apparatus housings of at least two different blood treatment apparatuses, with each apparatus comprising a separate blood pump configured to pump blood extracorporeally. The blood circulation adapter can also comprise an extracorporeal blood circuit attached to the adapter housing. Alternatively, the extracorporeal blood circuit can be configured to engage the respective blood pumps. The extracorporeal blood circuit can comprise an arterial blood line, a venous blood line, and a blood filter all in fluid communication with one another. The blood filter can be configured for fluid communication alternatively with respective dialysate circuits in the at least two different blood treatment apparatuses. The blood filter can be, for example, a dialyzer.

The blood circulation adapter can further comprise a closure system configured to (i) interrupt fluid communication between the blood filter and the respective dialysate circuits when the blood circulation adapter is disengaged from the respective blood treatment apparatuses, and (ii) provide fluid communication between the blood filter and the respective dialysate circuits when the blood circulation adapter is engaged with a blood treatment apparatus. The closure system can comprise, for example, a first valve set comprising a first plurality of valves configured to alternatively provide fluid communication between the blood filter and the respective dialysate circuits when the blood circulation adapter is engaged with one of the respective blood treatment apparatuses. A blood circulation adapter that is configured for fluid communication of dialysate flow, instead of blood flow, can instead be used and can include or share one or more components of an adapter configured for fluid communication with blood flow. Thus, both "blood-side" and "dialysate-side" adapters are part of the present invention. A given adapter can be configured to communicate fluidically with a blood treatment apparatus through an extracorporeal blood circuit, a dialysate circuit, or both. An adapter can be dedicated as a blood-side or dialysate side adapter, or be convertible between the two.

The methods of using and the systems comprising the blood circulation adapter are also provided. A modular system is provided that can comprise a blood circulation adapter further comprising an adapter dialysate circuit and a blood filter in fluid communication with the extracorporeal blood circuit and the adapter dialysis circuit. The adapter dialysate circuit can include, for example, at least the dialysate side of a dialyzer. The modular system can also comprise a blood treatment apparatus comprising a blood pump and an apparatus dialysate circuit. The apparatus can be configured to engage the blood circulation adapter and to perform at least one blood treatment on a patient. The modular system can further include a closure system configured to provide fluid communication between the adapter dialysate circuit and the apparatus dialysate circuit. The modular system can include one or more additional blood processing apparatuses that can engage the blood circulation adapter. The apparatuses of the modular system can be of the same, similar, or differing designs, but can still be capable of engaging the blood circulation adapter in a universal fashion. For example, the apparatuses can differ in their blood processing configurations, functionalities, portability, combinations thereof, or the like.

A method is provided that can include providing the modular system; connecting the extracorporeal blood circuit to a patient; engaging the portable blood circuit adapter with the blood treatment apparatus; opening the closure system to provide fluid communication of dialysate between the blood circulation adapter and the apparatus; and performing at least one blood treatment on the patient. The method can also comprise interrupting the treatment and disengaging the adapter from the apparatus without disconnecting the adapter from the patient. The method can further comprise re-engaging the adapter with the same apparatus or engaging the adapter with a different apparatus, and resuming the same treatment or beginning a different treatment, also without disconnecting the adapter from the patient. The adapter can be engaged to an intermediate apparatus for transport between two different blood treatment apparatuses. The intermediate apparatus can maintain circulation of blood in the extracorporeal blood circuit or can be configured with greater functionality.

Figure 1B:
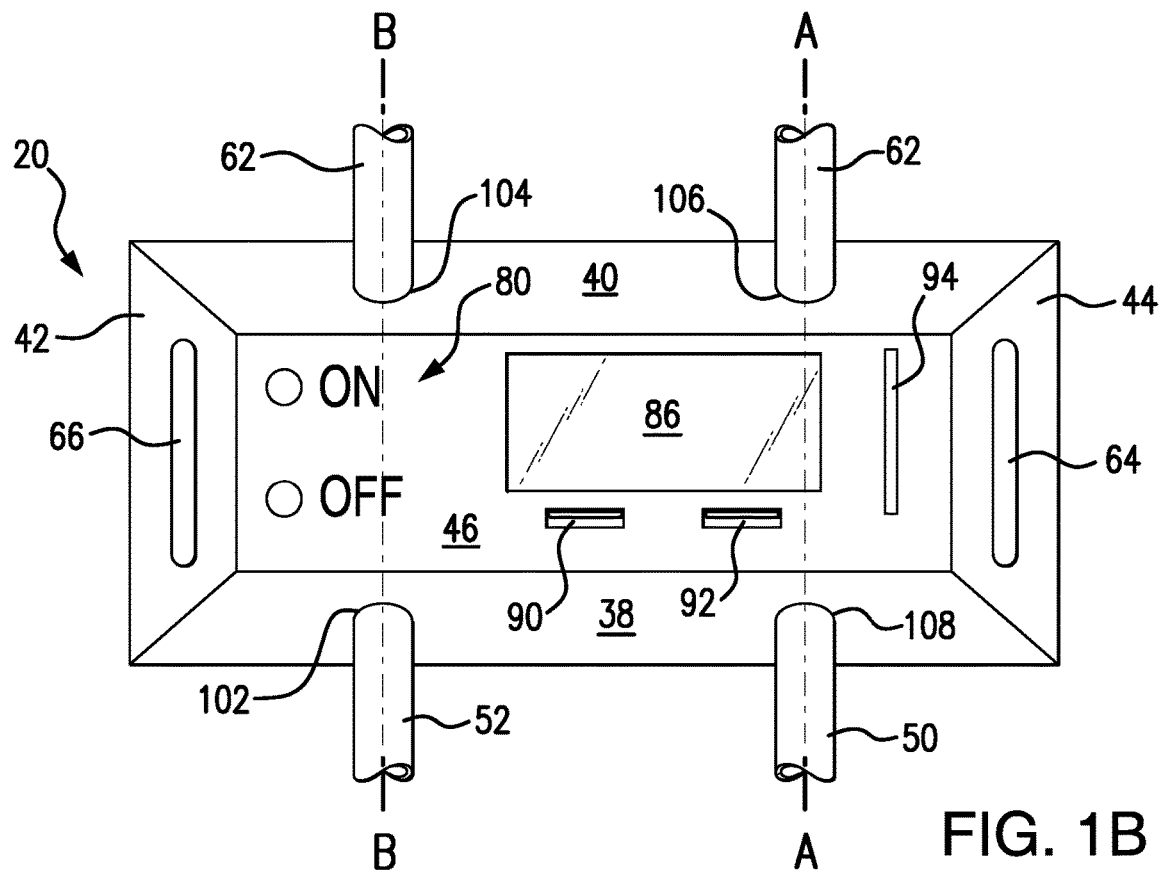
FIG. 1B is a top (plan) view of the adapter shown in FIG. 1A.
Figure 1C:
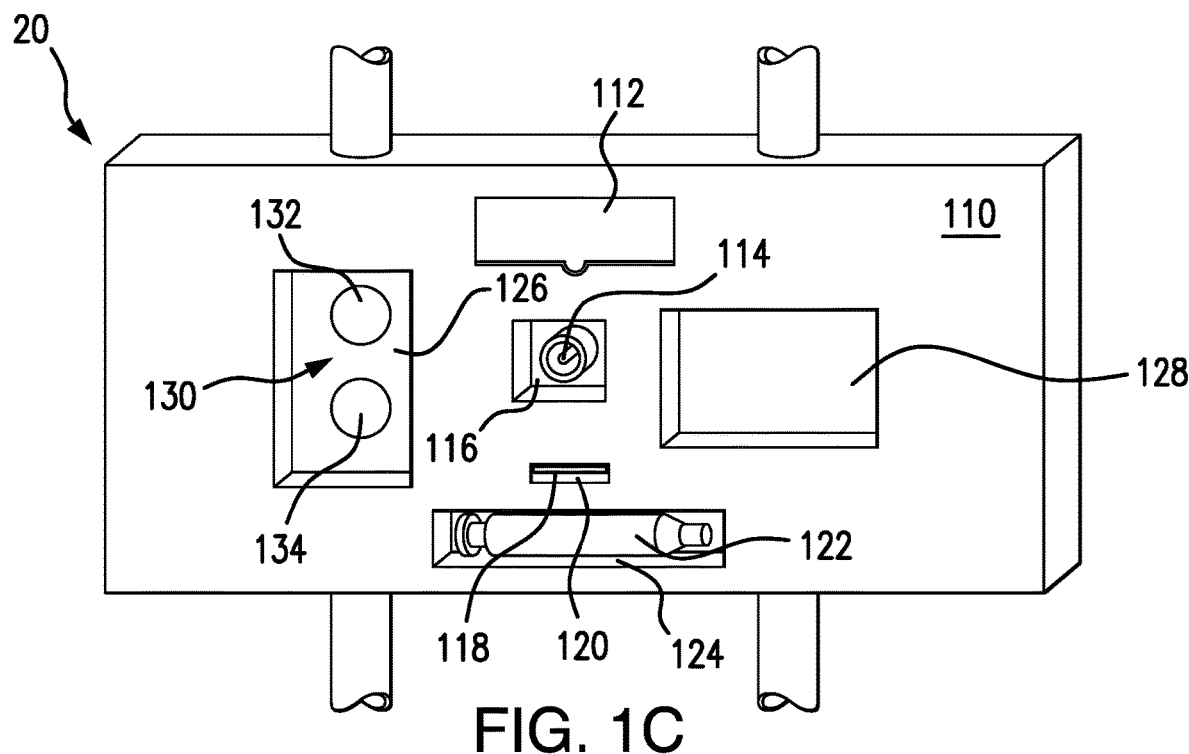
FIG. 1C is a bottom view of the adapter shown in FIG. 1A.
Figure 1D:
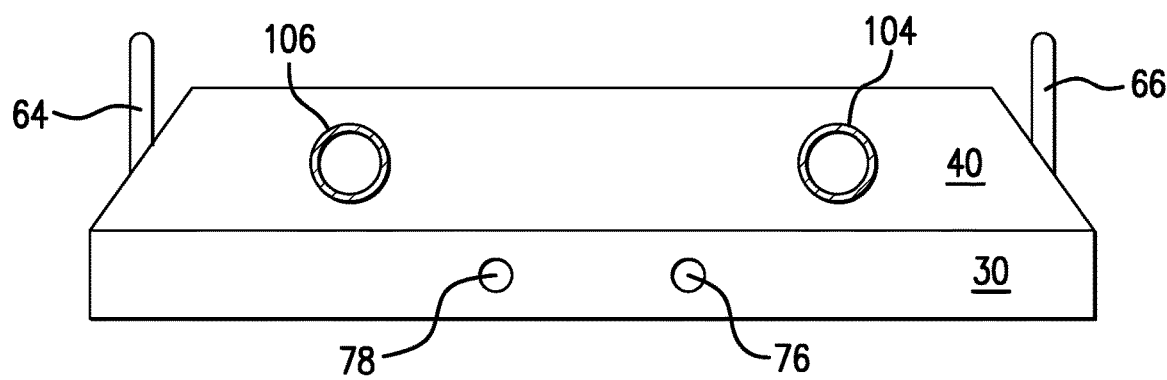
FIG. 1D is a back view of the adapter shown in FIG. 1A with a blood pump engagement loop cut away.
Figure 1E:
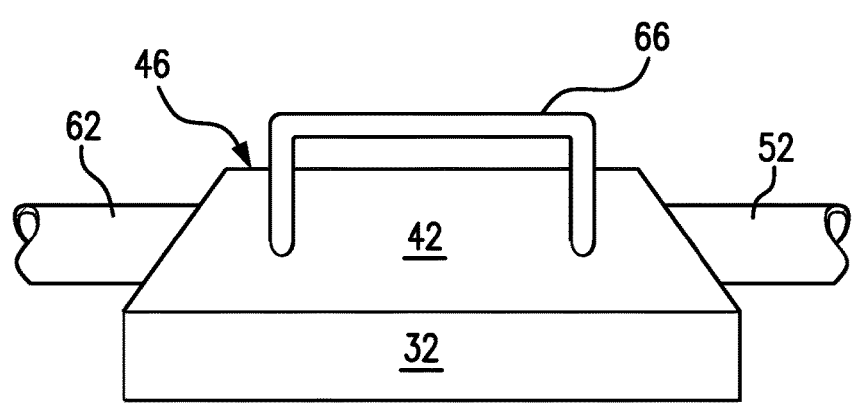
FIG. 1E is a left side view of the adapter shown in FIG. 1A.

With reference now to the drawings, FIG. 1A is a perspective view of a first (portable blood circuit) adapter 20 configured to engage with a base module or portable module in accordance with the present invention. FIG. 1B is a top (plan) view of first adapter 20 shown in FIG. 1A. FIG. 1C is a bottom view of first adapter 20 shown in FIG. 1A. FIG. 1D is a back view of the first adapter 20 shown in FIG. 1A with a blood pump engagement loop cut away. FIG. 1E is a left side view of first adapter 20 shown in FIG. 1A.

The first blood line set 48 is configured to carry blood between the patient, the first portable adapter 20, a blood processing apparatus (not shown in FIGS. 1A-1H) engaged with the first portable adapter 20, or some combination thereof. The first blood line set 48 can include a first venous line 50, an arterial line 52, and an engagement loop 62. The venous line 50 extends from the patient end 54 to the adapter end 56. The arterial line 52 extends from the patient end 58 to the adapter end 60. The engagement loop 62 extends from the adapter body 26 (e.g., from a side opposing the venous and arterial lines).

The engagement loop 62 is configured to engage a pump, for example, a peristaltic pump, on a face of a blood processing apparatus. If the blood pump is instead situated internal to the housing of a blood processing apparatus, then the engagement loop 62 can be modified or omitted. The first blood line set 48 and the engagement loop 62 can be separately packaged or supplied together. In some examples, the first blood line set 48, the engagement loop 62, or both are packaged or supplied while connected to the adapter 20.

The individual parts, lines, tubing lengths, and the like, of the first blood line set 48 can be distinct components or form one or more continuous tubes. The first blood line set 48 can be integral, in whole or in part, with the housing 22 or can be a distinct component. The blood line set 48 and the housing 22 can be supplied in a sterilized state. The first portable adapter 20 can be supplied in sterilized form. Removable end caps can be included on tube ends to aid in sterilization and to avoid contamination. Adapters can be packaged individually or in sets of two or more adapters. The first adapter the housing 22 can be configured to be stackable to enable stacking of multiple adapters in individual or separate packages. A desiccant can be included in the packaging. A date, expiration, sterilization, and/or contamination indicator can be located in or on the packaging. For example, a color change type indicator can be included in the packaging and be configured to change color in response to, for example, sterilization, contamination, humidity, an air breach, and/or elapse of a predetermined period. The first portable adapter 20, any component thereof, or any other component or device described herein, can include one or more scannable tag, for example, a barcode (one-dimensional, two-dimensional, or the like), a radio frequency identification (RFID) tag, an alphanumeric code, a color code, an infrared code, a symbolic code, or the like.

The first portable adapter 20 can include one or more elements to aid a user in his or her handling and movement of the adapter (e.g., a first handle 64 and a second handle 66). For example, the first handle 64 is shown with a circular cross-section and with a wide, shallow, and with a generally U-shaped structure extending from the first right sloped side 44. Similarly, the second handle 66 is shown extending from the first adapter body left the sloped side 42. The design, number, type, and placement of handles can be varied to accommodate the user and/or the machines to which the first portable adapter 20 is designed to engage. Handles can be fixed or detachable. Although the figures show the first and the second handles 64, 66 extending from the first top surface 46, other configurations are possible. For example, one or both of the first and second handles 64, 66 can extend to or below the first top surface 46. The configuration of the handles (e.g., the height, position, design, and/or angle) can be modified to suit the needs of a user or environment. For example, the handles can be configured to minimize or prevent complications with tubing, a machine engaged with the portable adapter 20, and/or a patient.

The base 24 is depicted, for example, as a rectangular prism and the body is depicted, for example, as a frustum rectangular pyramid. The base 24 includes a base front, back, left, and the right lateral sides 28, 30, 32, and 34, respectively. The body 26 has corresponding first adapter front, back, left, and the right sloped sides 38, 40, 42, and 44, respectively. The sides can be continuous or interrupted, and there can be a rectilinear or curvilinear transition between adjacent sides. The transition can be beveled or rounded. The geometry of the first portable adapter 20 shown in the figures is for exemplary purposes only. The first portable adapter 20 can have any suitable geometry that enables its functional use and its engagement with base modules, portable modules, remote modules, and other compatible devices and apparatus. As described herein, by remote, what is meant is a modular component that is spaced away from, for example, at least one foot away, at least five feet away, at least ten feet away, at least twenty feet away, at least fifty feet away, at least 100 feet away, or some other distance away from a base module, portable module, or other remote module with which the remote module interacts. Remote modules can be portable or non-portable, can rely on a remote power source, or can be battery operated. By base module what is meant is a non-portable installation that is not intended to be picked up and moved. A base module can be hard-wired, plumbed, and the like, so as to be permanently installed at a base location. Portable modules of the present invention can be brought to and connected with the base modules, remote modules, or other portable modules and can rely on a remote power source or be battery operated. The housing geometry can be rectilinear, curvilinear, or both. The respective sides of the adapter housing base 24 and the body 26 can, for example, be continuous sides such that the base 24 and the body 26 appear indistinguishable. The base 24 and the body 26 can be distinct elements or elements with no particular demarcation. That is, for example, the entirety of the housing 22 can be a rectangular prism or a frustum rectangular pyramid, such that base and body sides are both perpendicular to a first top surface 46 or are both angular and not perpendicular with respect to the first top surface 46.

The first top surface 46 also includes a first data port 90, a second data port 92, and a first card reader 94. The size, type, placement, and number of these components can be varied. For example, a single data port can be provided or omitted. Any number of data ports can be provided, for example, from zero to about ten or from one to five, or two, three, or four data ports, can be provided. The data ports 90, 92 can use various connections having sufficient performance and data transfer capabilities (e.g., a universal serial bus (UBS) or FIREWIRE connection). The first card reader 94 can accept any suitable card type, for example, an SD card. The card can be used for identification of a patient, identification of a prescription or protocol, payment for a blood processing procedure, and/or the like. In some examples, the card reader 94 is omitted. In other examples, the adapter 20 operates using the card reader 94 and one or more the data ports, 90, 92.

Other user or control interfaces can be used. For example, a control interface for the blood processing apparatus, a personal (mobile) communication device (e.g., a smartphone, tablet, and/or smartwatch), and/or an interface at a central control station can be used alternatively or in addition to the user interface 86.

The first portable adapter 20, alone or in combination with a blood processing apparatus, can include a locking system 70. FIGS. 1A and 1D show the locking system 70 including a first bolt hole 72, a second bolt hole 74, a third bolt hole 76, and a fourth bolt hole 78. An adapter engagement verification subsystem 80 can be provided as part of the first portable adapter 20 and/or as part of a blood processing apparatus engaged with the first portable adapter 20. The adapter engagement verification subsystem 80 can optionally include one or more sensors (e.g., a pressure transducer, a photocell, a contact sensor, an electrical sensor, or the like) to detect information about the engagement between the first portable adapter 20 and a blood processing apparatus. The adapter engagement verification subsystem 80 can work independently from, or in operative communication with, the locking system 70 to indicate whether or not the first portable adapter 20 is securely engaged to a blood processing apparatus so that blood processing can begin or resume. The adapter engagement verification subsystem 80 can also detect, identify, and/or indicate engagement information (e.g., if the first portable adapter 20 is disengaged from the blood processing apparatus). In some examples, other components (e.g., modules, systems, subsystems, and/or stations) can use this engagement information to identify whether the first portable adapter 20 can be safely removed or to prevent blood processing.

The adapter verification subsystem 80 can relay the engagement information using one or more visual, audible, or haptic signals. For example, an indicator (e.g., a LED 82 on the first top surface 46) can visually signal the engagement. A different indicator and/or indication (e.g., a LED 84 differing in color from a LED 82) can visually signal disengagement.

Alternatively, or additionally, a user interface 86 can display whether the adapter 20 is engaged or disengaged. In some examples, the user interface 86 is on the top surface 46, but the user interface 86 can be omitted or repositioned from the top first surface 46. The size, type, placement, and number of screens or components of the user interface 86 can vary. The user interface 86 can comprise a touchscreen display or simply a liquid crystal or LED display. The user interface 86 can have various functionalities, for example, display and/or control of a blood processing mode of operation, display of a processing step/stage, display of a warning, and/or display of user preferences.

The first blood line set 48 can account for all or part of a first adapter blood circuit. The first blood line set 48 passes in and out of the first adapter the housing 22 at the first port 102, the second port 104, the third port 106, and the fourth port 108. Although the first blood line set 48 is shown passing in and out of the first portable adapter 20 in the first adapter body 26, this is for exemplary purposes only. The location of the ports can be varied in position and number to accommodate various embodiments and uses of the first portable adapter 20.

A first bottom surface 110 is shown in FIG. 1C. A battery panel 112 can cover a recess containing one or more batteries, fuel cells, or other energy sources, whether rechargeable or single-use. Power can also be provided to the first portable adapter 20 through the power connector 114 set in a power recess 116, for example, power can be provided directly from an AC power outlet, indirectly through a power cable, indirectly through the interface of a blood processing apparatus, or from another source. A data connector 118 can be, for example, set in a data recess 120 in the first bottom surface 110. Although only a single adapter data connector is shown, multiple such connectors can be provided, for example, one for each of the first data port 90, the second data port 92, and optionally the first card reader 94. Adapter data connector can connect directly to a computer, indirectly through a data cable, through an interface on a blood processing apparatus, or through another route. A common power/data connector can be used instead of, or in addition to, separate power and data connectors. The power connector 114 and/or the data connector 118 can be omitted, and, for example, power and/or data can be supplied through the first adapter first or second data ports, 90, 92. An inductive power source/transfer and/or wireless data connection can be provided.

An anticoagulant dispenser 122 can be set in an anticoagulant recess 124 in the first bottom surface 110. The anticoagulant dispenser 122 can be a syringe containing one or more anticoagulants, for example, heparin, citrate, chelators, and/or coumarin-based agents. Anticoagulants can be dispensed into the first adapter blood circuit that includes the first blood line set 48, for example, at a point in the first blood line set 48 that passes through the first adapter housing 22, for example, through a fluid communication to the blood line set 48 inside the first adapter housing 22. The anticoagulant dispenser 122 can be actuated manually or by an actuator of the system. In some examples, the first portable adapter 20 includes an actuator. In other examples, the first portable adapter 20 is mounted to a blood processing machine with an actuator. The anticoagulant dispenser 122 can be omitted, replaced, or complemented with another anticoagulant dispenser, for example, one mounted on the face of a blood processing apparatus and/or attached to an auxiliary tubing to the first blood line set 48.

In addition to the power recess 116, the data recess 120, and the anticoagulant recess 124, two other recesses are shown located in the first bottom surface 110. These recesses can include positioning recesses, for example, the first positioning recess 126 and the second positioning recess 128. Any suitable, number, type, or configuration of recesses can be used, or recesses can be omitted altogether. The first and the second positioning recesses 126, 128 are shown, for example, with similar shapes and sizes, but offset by about ninety degrees. In some examples, the positioning recesses can be provided with no offset or can be symmetrical about one or more planes, having offset and/or asymmetric positioning recesses. In other examples, protrusions on the blood treatment apparatus align with the first and the second positioning recesses 126, 128. Together, these protrusions and recesses help to prevent a connection when the portable adapter 20 is misoriented (e.g., inverted).

A connector 130 is shown in the first positioning recess 126. The connector 130 provides a fluid connection for fluid flow (e.g., the flow of blood and/or dialysate between the first portable adapter 20 and a blood processing apparatus). The connector 130 can include an exit port 132 for liquid flow from the first portable adapter 20 and an entry port 134 for liquid flow into the first portable adapter 20. The connector 130 can enable, for example, blood flow or dialysate flow between the first portable adapter 20 and a blood processing apparatus.

The terms "exit" and "entry" are used herein for ease of description. It is to be understood that the flow of fluid entering or exiting any device described herein can be reversed. The positioning and/or function of the exit port 132 and the entry port 134 can be varied or reversed, for example, by the configuration of one or more pumps in fluid communication with the first portable adapter 20 and/or in fluid communication with the first adapter blood circuit.

Figure 1F:
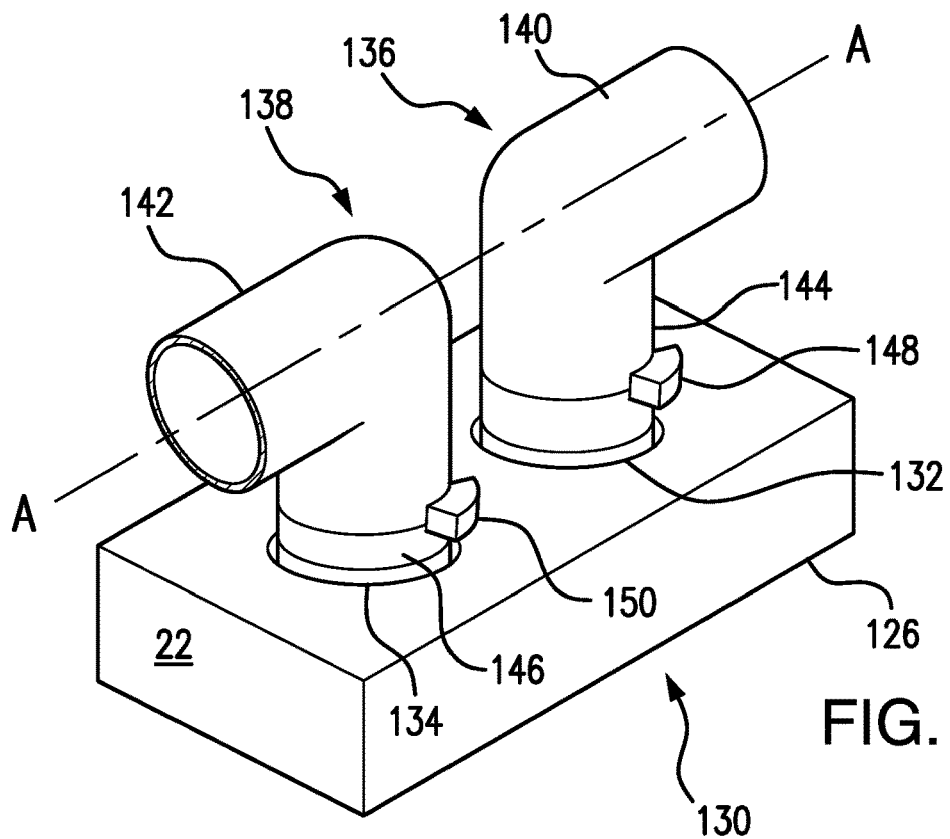
FIG. 1F is a partial internal view of the adapter shown in FIG. 1A and shows details of the adapter inter-module connector.
Figure 1G:
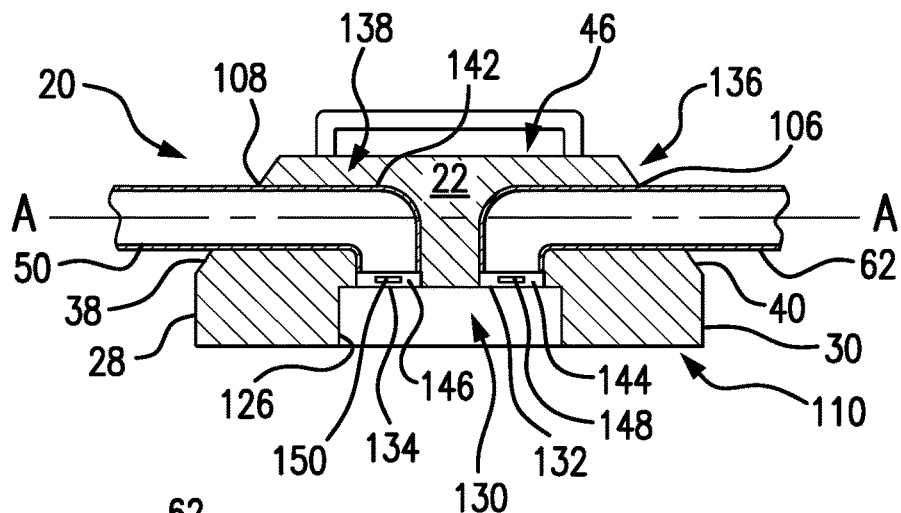
FIG. 1G is a cross-sectional view of the adapter shown in FIG. 1B taken along line A-A of FIG. 1B.
Figure 1H:
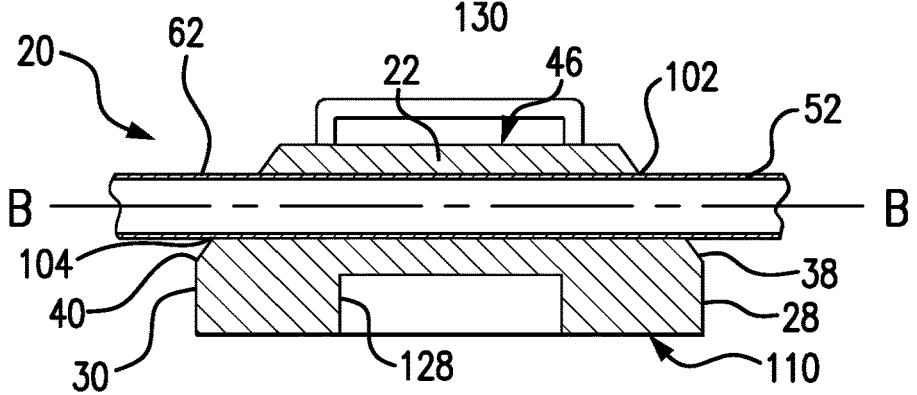
FIG. 1H is a cross-sectional view of the adapter shown in FIG. 1B taken along line B-B of FIG. 1B.

FIG. 1F is an enlarged view of a portion of the adapter shown in FIG. 1A, showing the adapter inter-module connector 130 details along line A-A shown in FIG. 1B. FIG. 1G is a cross-sectional view of the adapter taken along line A-A in FIG. 1B. In FIG. 1G, the first positioning recess 126 is visible. FIG. 1H is a cross-sectional view taken along line B-B in FIG. 1B, wherein the second positioning recess 128 is visible. In addition to the exit port 132 and the entry port 134, the inter-module connector 130 includes the exit connector 136 and the entry connector 138. The exit connector 136 and the entry connector 138 can include the exit connector 140 and the entry connector 142, respectively, which can be components of and/or in engagement with the first blood line set 48. The tube connectors can simply be passages in the housing 22 or distinct tubes that pass through such passages. The exit connector 136 and the entry connector 138 can include exit valve 144 and the entry valve 146 respectively. Exit valve 144 and the entry valve 146 can be controlled by or through the exit valve actuator 148 and the entry valve actuator 150 respectively. Valves complementary to the exit valve 144 and the entry valve 146 can be provided on the face or internal to a blood processing apparatus mounted to first portable adapter 20.

Any type of valve and/or actuator can be used. For example, a spring-actuated trapdoor valve coupled with a complementary O-ring connection can be used. Examples of valves include hydraulic valves, pneumatic valves, manual valves, solenoid valves, motor valves, ball valves, butterfly valves, disc valves, clapper valves, check valves, choke valves, diaphragm valves, gate valves, glove valves, knife valves, needle valves, pinch valves, piston valves, plug valves, poppet valves, spool valves, expansion valves, pressure valves, cone valves, duck-bill valves, multi-turn valves, quarter-turn valves, strainer valves, angle valves, orbit valves, bellow sealed valves, automatic valves, recirculation valves, and the like. One-way, two-way, three-way, four-way, and similar valves can be used. Valves can be controlled through the first portable adapter 20, a blood processing apparatus, and/or a central control center, through electrical, wired, wireless, mechanical, pneumatic, hydraulic, or other controls, any combination thereof, or the like. Such connection types are also applicable to any other valve or other actuator described herein.

Figure 2:
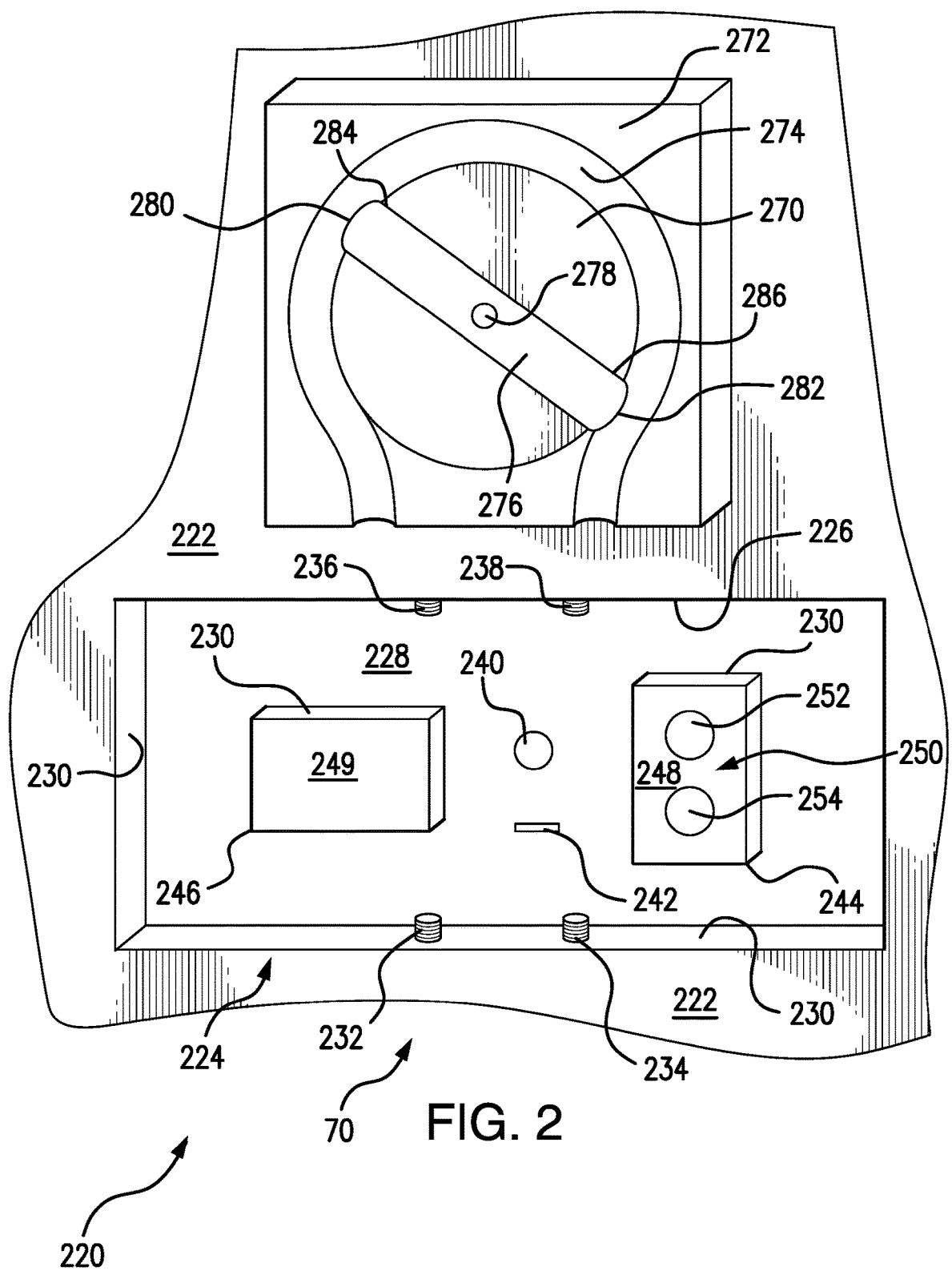
FIG. 2 is a perspective view of a blood processing apparatus interface configured to receive the adapter of FIGS. 1A-1H.

FIG. 2 is a perspective view of a blood processing apparatus interface 220 configured to receive the first portable adapter 20 shown in FIGS. 1A-1H, demonstrating, for example, a closure system. Blood processing apparatus interface 220 can be located on an apparatus front surface 222 of a blood processing apparatus. An interface receptacle 224 can include a receptacle recess 226 configured to receive the first portable adapter 20 or another compatible adapter. The receptacle recess 226 includes a rear surface 228 and a lateral surface 230 with one or more retractable bolts (e.g., bolts 232, 234, 236, and 238). The bolts 232, 234, 236, and 238 engage a corresponding bolt hole 72, 74, 76, and 78. The bolts 232, 234, 236, and 238 are shown in an extended position. To mount the first portable adapter 20, the bolts 232, 234, 236, and 238 are retracted until the portable adapter 20 is correctly positioned, and are then actuated to extend into and secure the first portable adapter 20 once mounted. Bolts and/or bolt holes can be omitted if the locking system 70 is used or if the locking system 70 is omitted.

Several components are shown in or extending from a receptacle rear surface 228, including a complementary power connector 240, a complementary data connector 242, first positioning protrusion 244, second positioning protrusion 246, and front surfaces 248 and 249. These components are complementary to the power connector 114, the data connector 118, the first positioning recess 126, and the second positioning recess 128, respectively, of the first portable adapter 20 as shown in FIG. 1C. A common complementary power/data connector can be used instead of or in addition to separate complementary power and data connectors. Complementary components described herein can have, for example, corresponding male/female designs, or can have alternative designs. Components shown having a male-design can alternatively have a female-design, and vice versa while preserving a complementary relationship. Auxiliary converters with or without intervening wiring, tubing, and/or housings can be used to provide complementarity.

A complimentary inter-module connector 250 is located in the first positioning protrusion 244. The complimentary inter-module connector 250 is complementary to the inter-module connector 130. Those two connectors can connect directly or through one or more connecting lines and/or other components. The complimentary inter-module connector 250 includes an entry port 252 and an exit port 254, which are complementary to the exit connector 136 and the entry connector 138, respectively.

Mounted on and extending from apparatus front surface 222 above an interface receptacle 224 is a blood pump 270. The blood pump 270 includes a pump frame 272, a tubing loop engagement track 274 configured to receive the first adapter blood pump the engagement loop 62 (FIGS. 1A, 1B, 1E, 1G, and 1H), and an blood pump rotor 276. The blood pump rotor 276 is configured to rotate about a blood pump axle 278. The blood pump rotor 276 can include a first blood pump head 280 and a second blood pump head 282 positioned at a blood pump rotor first end 284 and at a blood pump rotor second end 286, respectively. Although the blood pump 270 is shown as, and can be, a peristaltic pump, other kinds of pumps can be used in the alternative or in addition to a peristaltic pump, for example, a positive displacement pump, a rotary-type displacement pump, a reciprocating-type displacement pump, a linear-type displacement pump, a gear pump, a screw pump, a vane pump, a scroll compressor, a plunger pump, a diaphragm pump, a piston pump, a rotary lobe pump, a progressive cavity pump, a hydraulic pump, a flexible impeller pump, an impulse pump, a ram pump, a velocity pump, a radial-flow pump, an axial-flow pump, a mixed-flow pump, an educator-jet pump, a gravity pump, a valved pump, a valveless pump, and the like. The blood pump 270 can alternatively or additionally be wholly or partly positioned within the housing of the blood treatment apparatus.

The structural nature of the blood processing apparatus interface 220 enables engagement of the interface not only with the first portable adapter 20, but also with other alternative adapters of the present invention, for use in blood processing (treatment) procedures. Thus, the blood processing apparatus interface 220 is referred to herein as universal as its use is not restricted to use with only a single type of adapter. The blood processing apparatus interface 220 can engage a cleaning adapter to allow a blood processing apparatus to be cleaned and/or sterilized between procedures or use. Similarly, a priming adapter can be engaged for a priming sequence. A cleaning or other adapter can also be left in place as a cover between uses to minimize or prevent contamination of blood processing apparatus interface 220. Being universal, the blood processing apparatus interface 220 can connect with these other types of adapters also.

The blood processing apparatus interface 220 can be equipped with a cover, for example, hinged, sliding, snap-fit, or the like, for protection. Surfaces of the first portable adapter 20 and the blood processing apparatus interface 220 can be treated with one or more antimicrobial compounds, compositions, films, particles, or the like to minimize or prevent contamination, for example, before and after use. The first bottom surface 110 can similarly be treated. A cover module can be used to store the blood processing apparatus and can comprise, for example, a bottom surface similar to that of the first bottom surface 110, including an adapter-first-positioning recess similar to 126 and an adapter-second-positioning recess similar to 128, but that otherwise has a blank or solid housing apart from optional bolt holes or alternative components of the locking system 70.

Figure 3A:
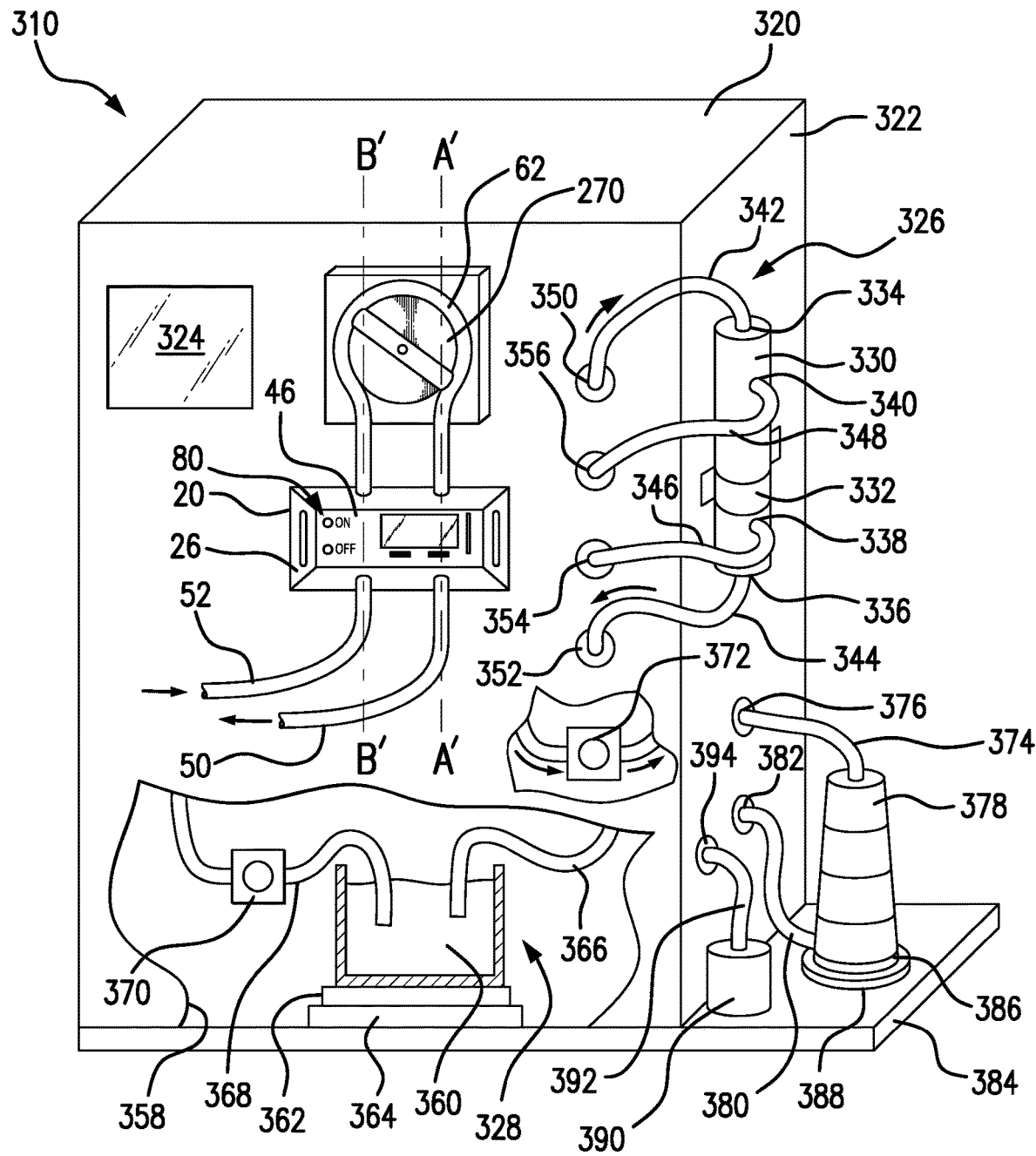
FIG. 3A is a perspective view of a modular system including a base module ("BM") and the adapter of FIGS. 1A-1H connected to the blood processing apparatus interface of FIG. 2.

FIG. 3A is a perspective view of a first modular system 310 including the first portable adapter 20 mounted on blood processing apparatus interface 220 of a first BM 320. The first BM 320 includes a first BM housing 322 on which a first BM user interface 324 can be positioned. Alternative or additional user interfaces can be included. The first BM 320 can include a first BM blood circuit 326 and a first BM dialysate circuit 328, which can interact with, complete, and/or complement blood and/or dialysate circuits in the first portable adapter 20. Blood from a patient can pass through both a first adapter blood circuit (including the engagement loop 62) and the first BM blood circuit 326. These two circuits can be considered to form a common or grand extracorporeal blood circuit. The first BM blood circuit 326 can include a blood filter 330, which can be secured to the first BM housing 322 by a blood filter fitting 332. The blood filter 330 can be, for example, a dialyzer that enables the flow of blood and/or dialysate through its interior. The blood filter 330 can include a blood entry port 334, a blood exit port 336, a dialysate entry port 338, and a dialysate exit port 340. A blood filter entry line 342, a blood filter exit line 344, a dialysate entry line 346, and a dialysate exit line 348 can extend to and from the respective ports of blood filter 330. These lines can also connect respectively to a first BM blood filter exit port 350, a first BM blood-from-filter entry port 352, a first BM dialysate filter exit port 354, and a first BM dialysate-from-filter entry port 356 in and/or on the first BM housing 322.

The partial cutaway nature of FIG. 3A shows a first BM interior 358 of BM 320. Located in the first BM interior 358 are a first BM dialysate reservoir 360, a first BM dialysate weighing subsystem 362, and a first BM dialysate heater 364. Dialysate can flow into the first BM dialysate reservoir 360 through a first BM dialysate reservoir entry line 366 and out of the reservoir 360 through a first BM dialysate reservoir exit line 368. A first BM primary dialysate pump 370 and a first BM secondary dialysate pump 372 can be located on and/or in fluid communication with first BM dialysate reservoir exit line 368 and a first BM sorbent entry line 374, respectively.

The first BM 320 is depicted in FIG. 3A as a sorbent-based blood processing apparatus for exemplary purposes only. The first base module can alternatively or additionally be a single-pass dialysate-based blood processing apparatus. The first BM sorbent entry line 374 can pass through a first BM dialysate-to-sorbent exit port 376 to a sorbent cartridge 378. Dialysate that has passed through the sorbent cartridge 378 can return to the first BM housing 322 through sorbent exit line 380, which can pass through a first BM dialysate-from-sorbent entry port 382. The sorbent cartridge 378 is depicted in FIG. 3A mounted on an accessory platform 384 outside of the first BM housing 322, but can alternatively be located partially or entirely inside the first BM housing 322. The sorbent cartridge 378 can be secured using sorbent cartridge fitting 386 directly to accessory platform 384 or through a sorbent cartridge weighing subsystem 388. Because the sorbent cartridge 378 may remove desirable electrolytes or levels thereof from the dialysate, an electrolyte supply 390, which can contain concentrated electrolytes, can be included on an accessory platform 384 or can alternatively be located partially or entirely inside the first BM housing 322. Concentrated electrolytes can be transferred to the first BM dialysate circuit 328 through an electrolyte line 392 that can pass through a first BM electrolyte entry port 394 in the first BM housing 322. Sorbent and electrolyte components and systems that can be used include, for example, those described in U.S. Pat. No. 8,784,668 B2 and in U.S. Patent Application Publication No. US 2014/0263062 A1, which are incorporated by reference herein in their entireties. Although the first BM 320 is depicted as a sorbent/regenerative-type system, this is for exemplary purposes only, and it is to be understood the first BM 320 can instead be provided, for example, as a single-pass-type system.

Figure 3B:
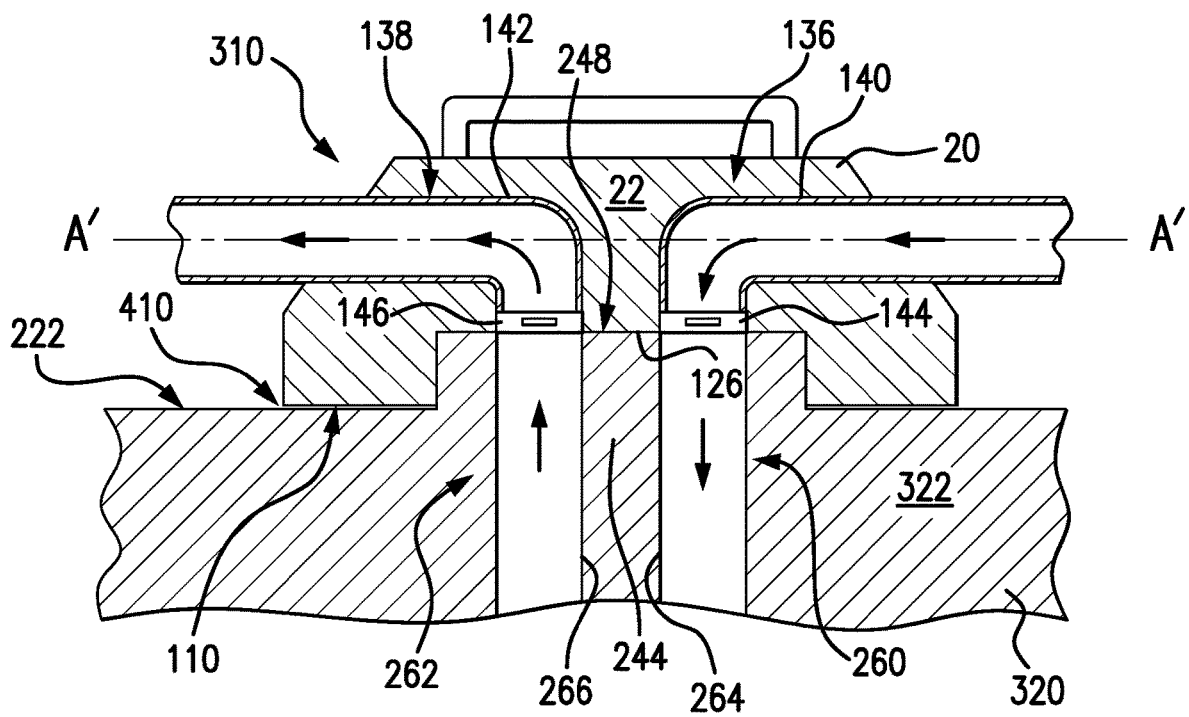
FIG. 3B is a cross-sectional view of the modular system shown in FIG. 3A taken along line A'-A' of FIG. 3A.

FIG. 3B is a cross-sectional view of the modular system shown in FIG. 3A taken along line A'-A' of FIG. 3A. As shown, the first BM 320 is connected to the first portable adapter 20 such as shown in FIG. 1G, at a first modular system interface 410, and demonstrates, for example, a closure system of the present invention. An entry connector 260 extends from the entry port 252 (FIG. 2) and an exit connector 262 extends from the exit port 254 (FIG. 2). The entry connector 260 can include entry connector tube 264. Exit connector 262 can include exit connector tube 266. Although not depicted in FIG. 3A, entry connector 260 and an exit connector 262 can include valves and a corresponding valve actuators complementary to the exit valve actuator 148 and the entry valve actuator 150, respectively. Valves can alternatively or additionally be located on auxiliary fluid lines configured to connect the adapter inter-module connector to a complementary base module inter-module connector.

Figure 3C:
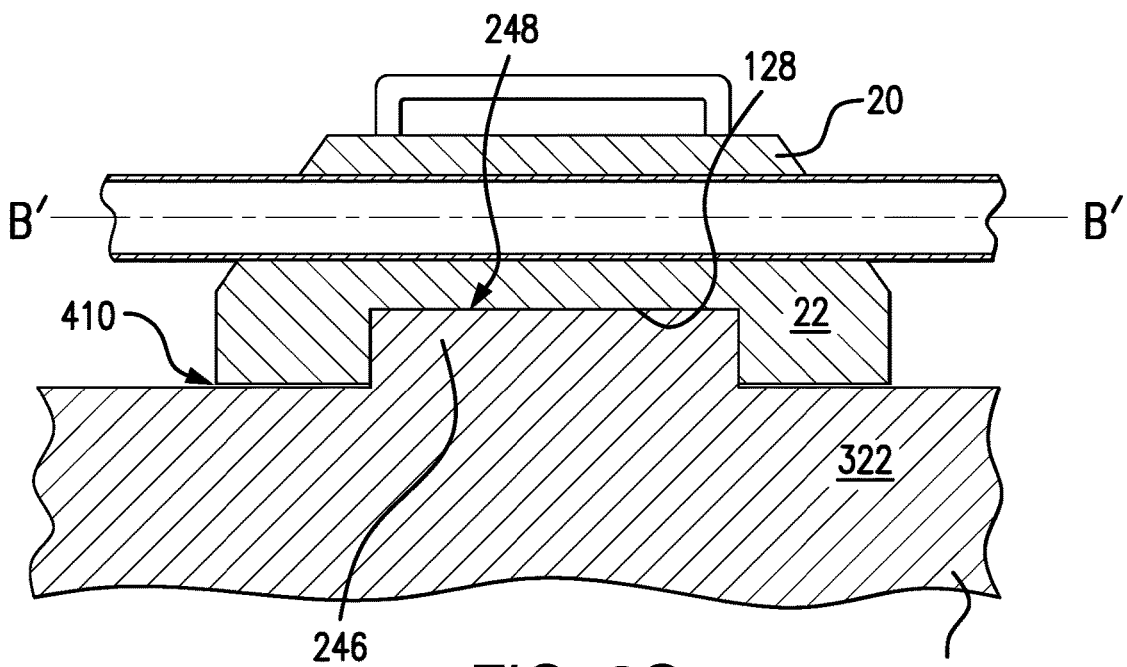
FIG. 3C is a cross-sectional view of the modular system shown in FIG. 3A taken along line B'-B' of FIG. 3A.

FIG. 3C is a cross-sectional view of the modular system shown in FIG. 3A along line B'-B' of FIG. 3A. The first BM 320 connects to the first portable adapter 20, such as shown in FIG. 1H, at a first modular system interface 410. While the BM 320 is described as a "base" module and is shown as a stationary apparatus, the BM 320 can convert into a portable module, for example, by the addition of wheels to the first BM housing 322 or placement on a cart or other conveyance. A portable module of the present invention can include all, additional, and/or a subset of the components shown and described for first BM 320. Examples of such portable modules are described herein.

Figure 4:
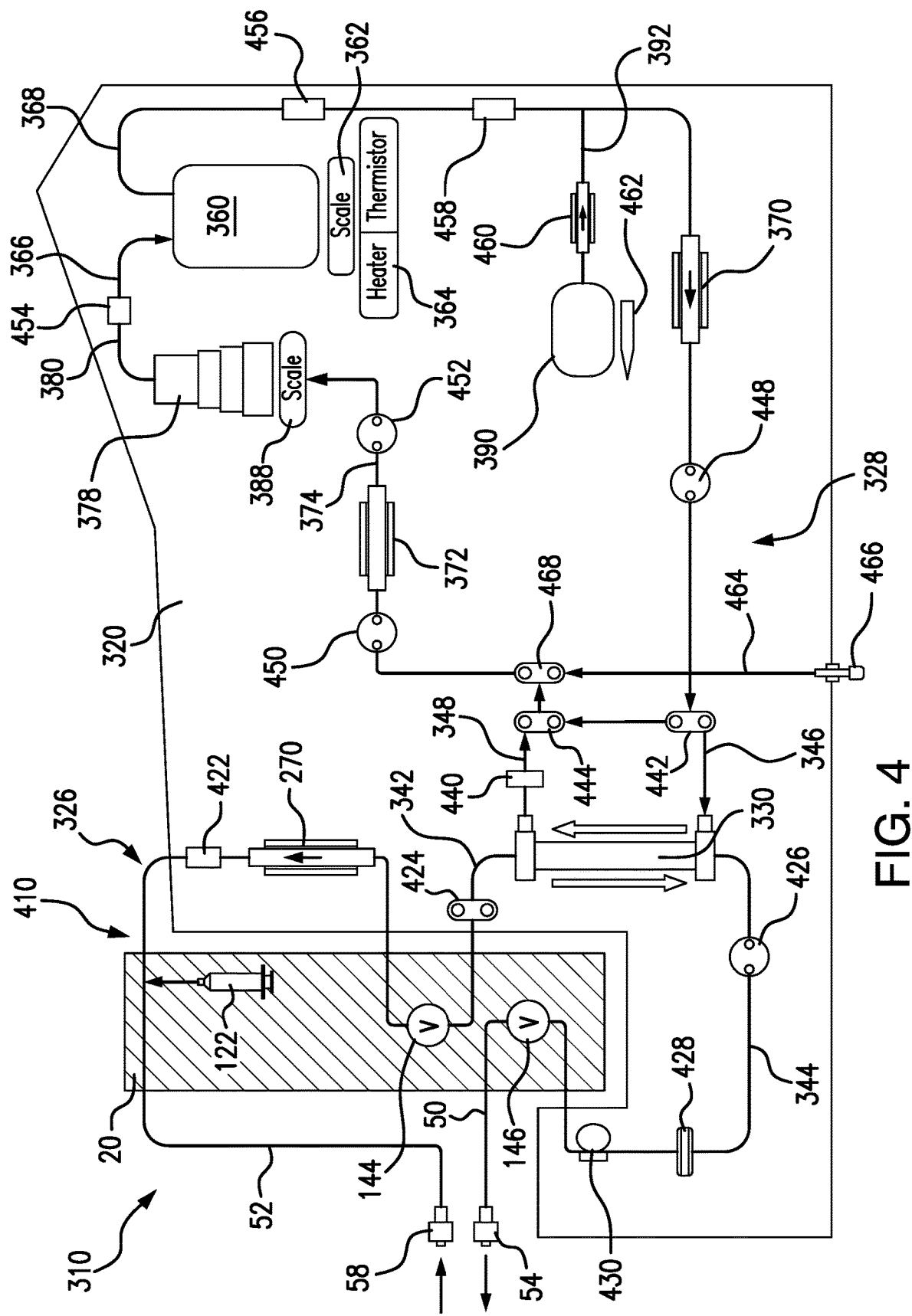
FIG. 4 is a schematic diagram of the modular system shown in FIGS. 3A-3C.

FIG. 4 is a schematic hydraulic circuit diagram of the first modular system 310 shown in FIG. 3A, including the blood and dialysate circuits. Beyond the components visible in FIG. 3A, additional elements of the first portable adapter 20 and the first BM 320 are depicted in FIG. 4. These components include, for example, an occlusion detector 422, a first (entry) blood pressure sensor 424, a second (exit) blood pressure sensor 426, an air bubble sensor 428, a pinch valve 430, and a blood leak sensor 440 in the blood circuit(s). The first BM dialysate circuit 328 can include an apparatus first auxiliary valve 442 and an apparatus second auxiliary valve 444 to provide additional control of the flow of dialysate. Pressure can be monitored in the first BM dialysate circuit 328 using one or more of a first (entry) dialysate pressure sensor 448, a second (exit) dialysate pressure sensor 450, and a third (sorbent entry) dialysate pressure sensor 452. The first BM dialysate circuit 328 can include an ammonia sensor 454, a temperature sensor 456, and/or a conductivity sensor 458. An electrolyte pump 460 and an electrolyte level sensor 462 can be used to monitor and control the supply of electrolyte concentrate in and from electrolyte supply 390. Fresh dialysate, water, and/or concentrate can be supplied to the first BM dialysate circuit 328. Spent dialysate can be discarded from the first BM dialysate circuit 328 using one or more of a fill/drain line 464, a fill/drain port 466, and a fill/drain valve 468.

Figure 5A:
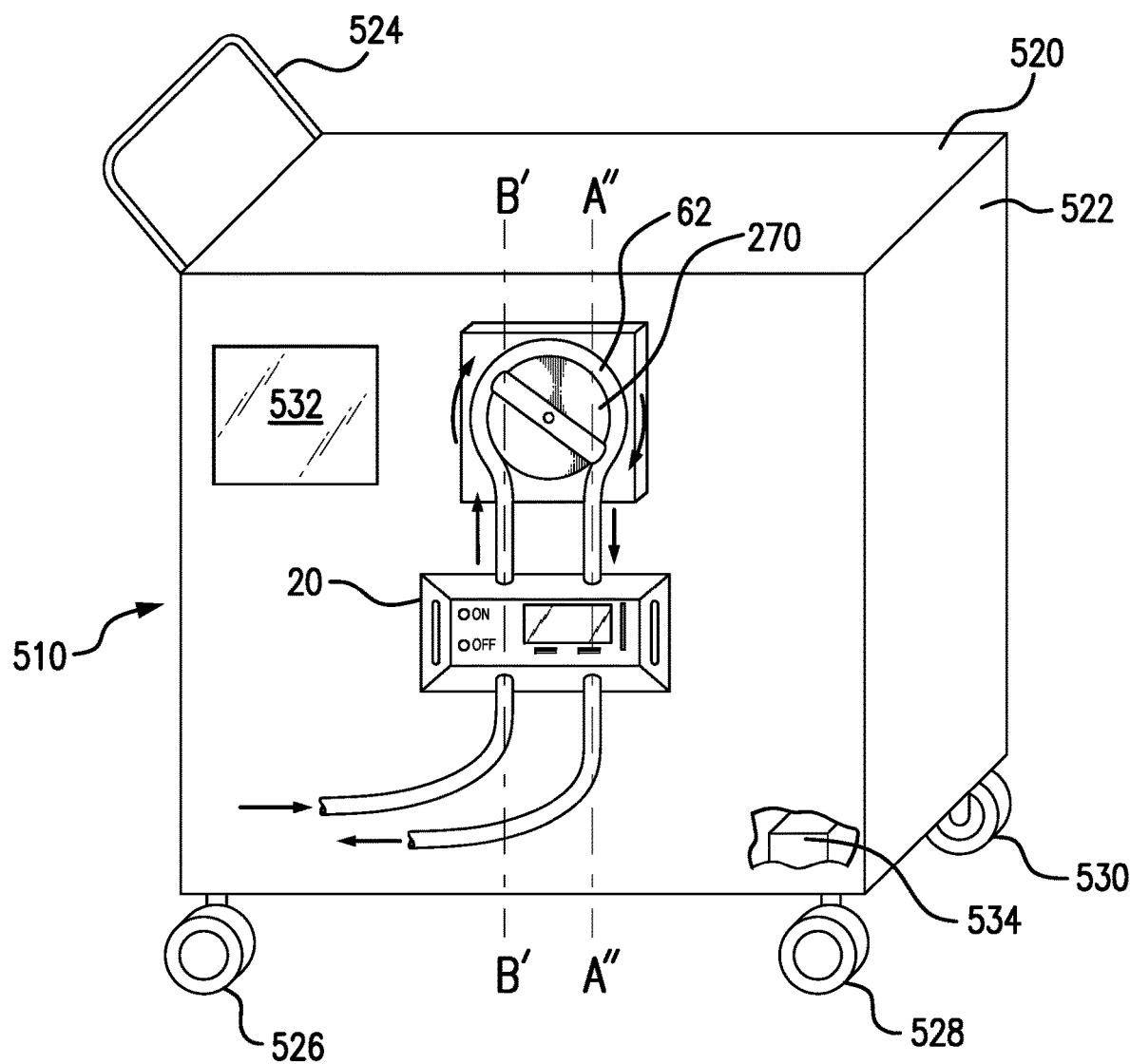
FIG. 5A is a perspective view of a modular system including a portable module and the adapter of FIGS. 1A-1H connected to the blood processing apparatus interface of FIG. 2.

FIG. 5A is a perspective view of a second modular system 510 including the first portable adapter 20 as shown in FIGS. 1A-1H mounted on a blood processing apparatus interface such as 220 shown in FIG. 2, of a first portable (blood processing) module 520. The first portable module 520 can include a first portable housing 522 upon which is mounted a first portable handle 524. The first portable module 520 can be conveyed by any suitable means. For example, one or more wheels may be mounted on the first portable housing 522 such as first portable wheels 526, 528, 530, and a fourth wheel (not visible). Wheels need not be mounted directly on the first portable housing 522. Alternatively, or additionally, first portable module can be placed on a cart or other vehicle for conveyance. A portable module in accordance with the present invention can also be conveyed by other means, for example, by being worn using a belt or harness on a patient. A first portable user interface 532 can be provided on the first portable housing 522 to enable operation and control of the first portable module 520. Alternatively, or additionally, first portable module 520 can be controlled through the user interface 86 (FIG. 1A), a base module user interface, a central control station interface, a personal communications device, or the like. The first portable module 520 can include a first portable power source 534, for example, a rechargeable battery, a fuel cell, a solar cell, or the like.

Figure 5B:
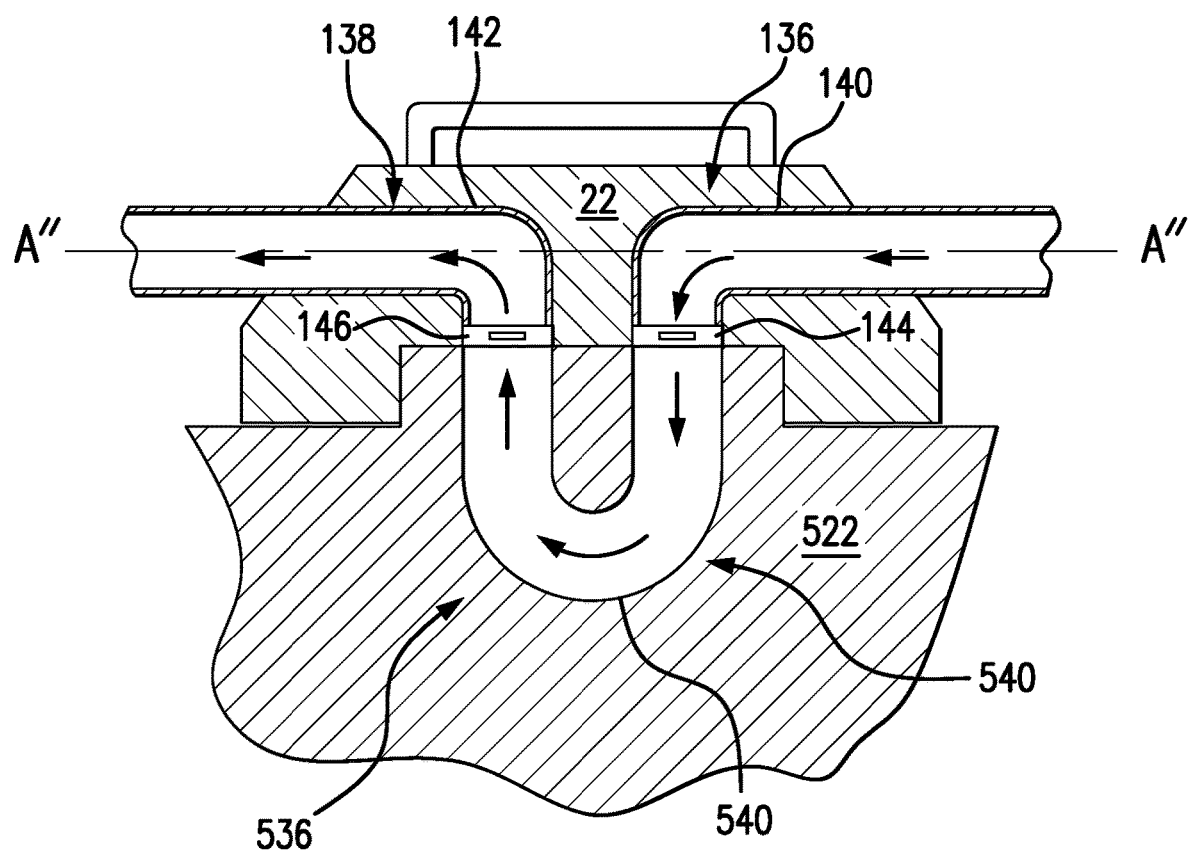
FIG. 5B is a cross-sectional view of the modular system shown in FIG. 5A taken along line A"-A" of FIG. 5A.

FIG. 5B is a cross-sectional view of second modular system 510 taken along line A"-A" of FIG. 5A. The connection of the first portable adapter 20 to the first portable module 520 is shown in a manner analogous to that between the first portable adapter 20 and the first BM 320 shown in FIG. 3A. The first blood circuit 536 includes, or can be, a first portable module short circuit or bypass circuit. Blood from a patient can pass through both the first adapter blood circuit and the first blood circuit 536. When connected, these two circuits can be considered to form a common or grand extracorporeal blood circuit. The first blood circuit 536 can include a blood bypass conduit 540 that joins and provides a fluid passage between the exit connector 140 and the entry connector 142 of the exit connector 136 and the entry connector 138 of the first portable adapter 20.

Figure 6:
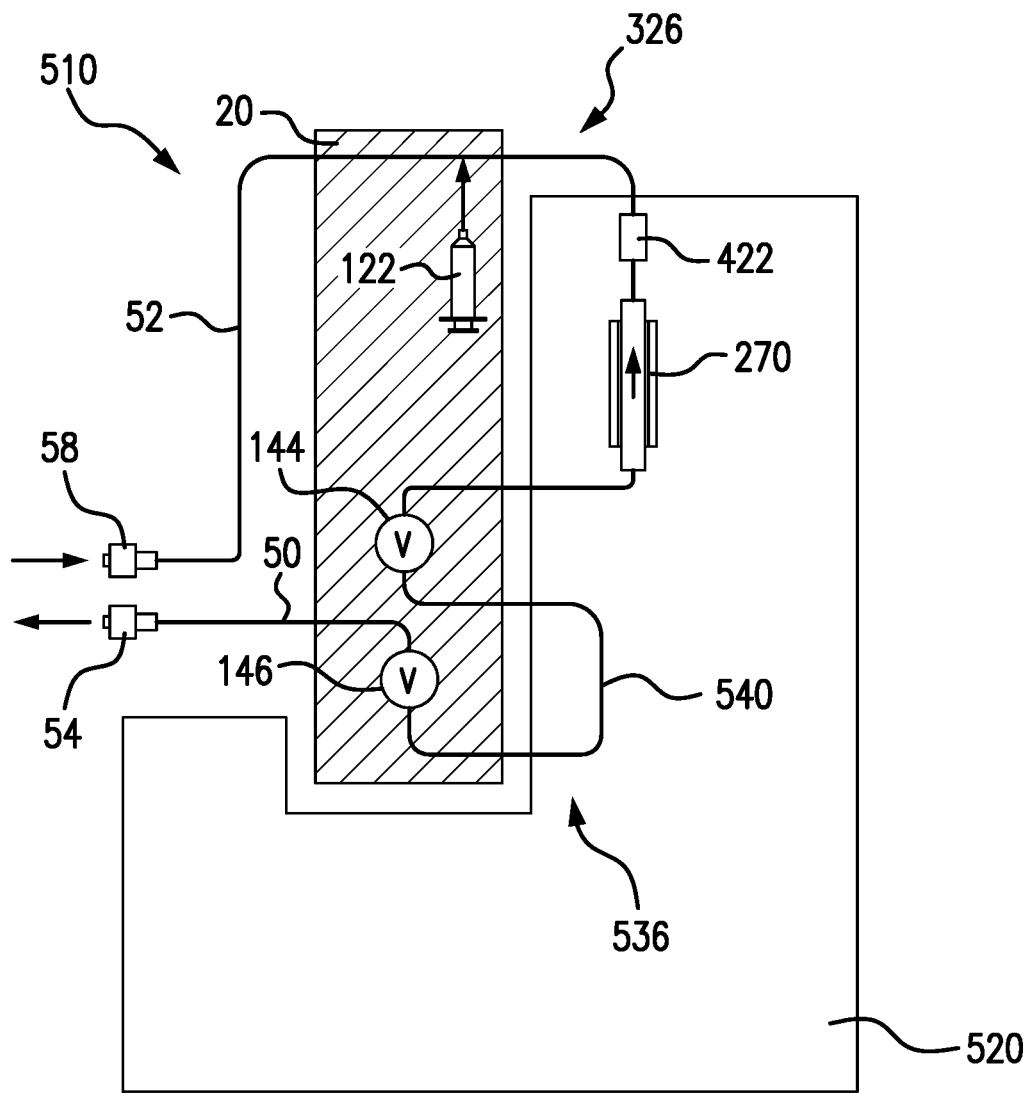
FIG. 6 is a schematic diagram of the modular system shown in FIGS. 5A-5B.
Figure 14:
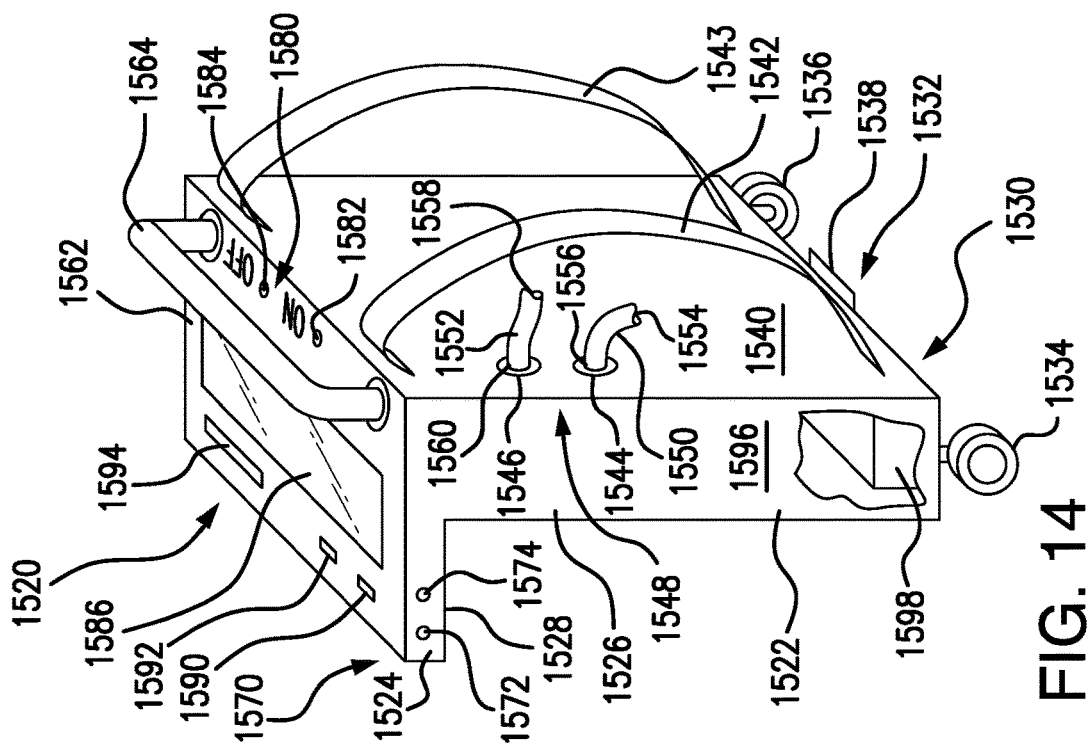
FIG. 14 is a perspective view of a portable module configured to dock with a BM.

FIG. 6 is a schematic diagram of the modular system shown in FIGS. 5A and 5B. The same reference numerals used in FIGS. 5A, 5B, and 6 that are used in other drawings herein represent the same features. The first portable module 520 enables a patient to disengage from one base module where blood processing has begun and to resume blood processing at another base module some distance away. Thus, the first portable module 520 can act as an intermediate-type module. By using the first portable module 520 engaged with the first portable adapter 20, the patient can maintain blood circulation and decrease the likelihood of clotting or other complications during travel between two BMs or travel from and return to the same BM. The patient can thus travel without having to remove the blood line set 48 from his or her vasculature. Given the reduced number of components of the first portable module 520, it can have a relatively small size that facilitates portability and can take the form, for example, of a backpack as described herein. As an example, the portable module can be a third portable module 1520 as shown in FIG. 14.

Figure 7:
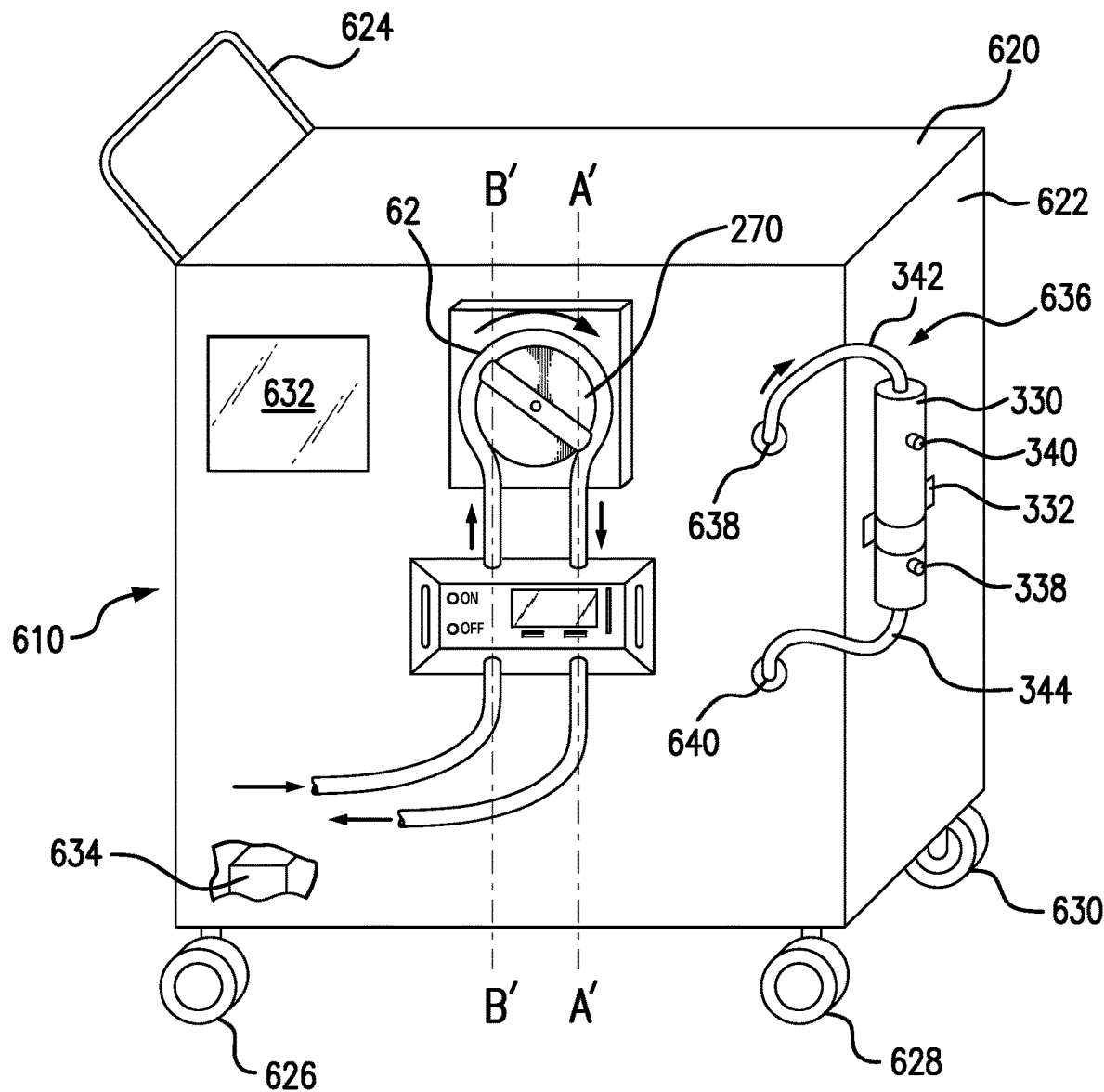
FIG. 7 is a perspective view of a modular system including a portable module and the adapter of FIGS. 1A-1H connected to the blood processing apparatus interface of FIG. 2.
Figure 8:
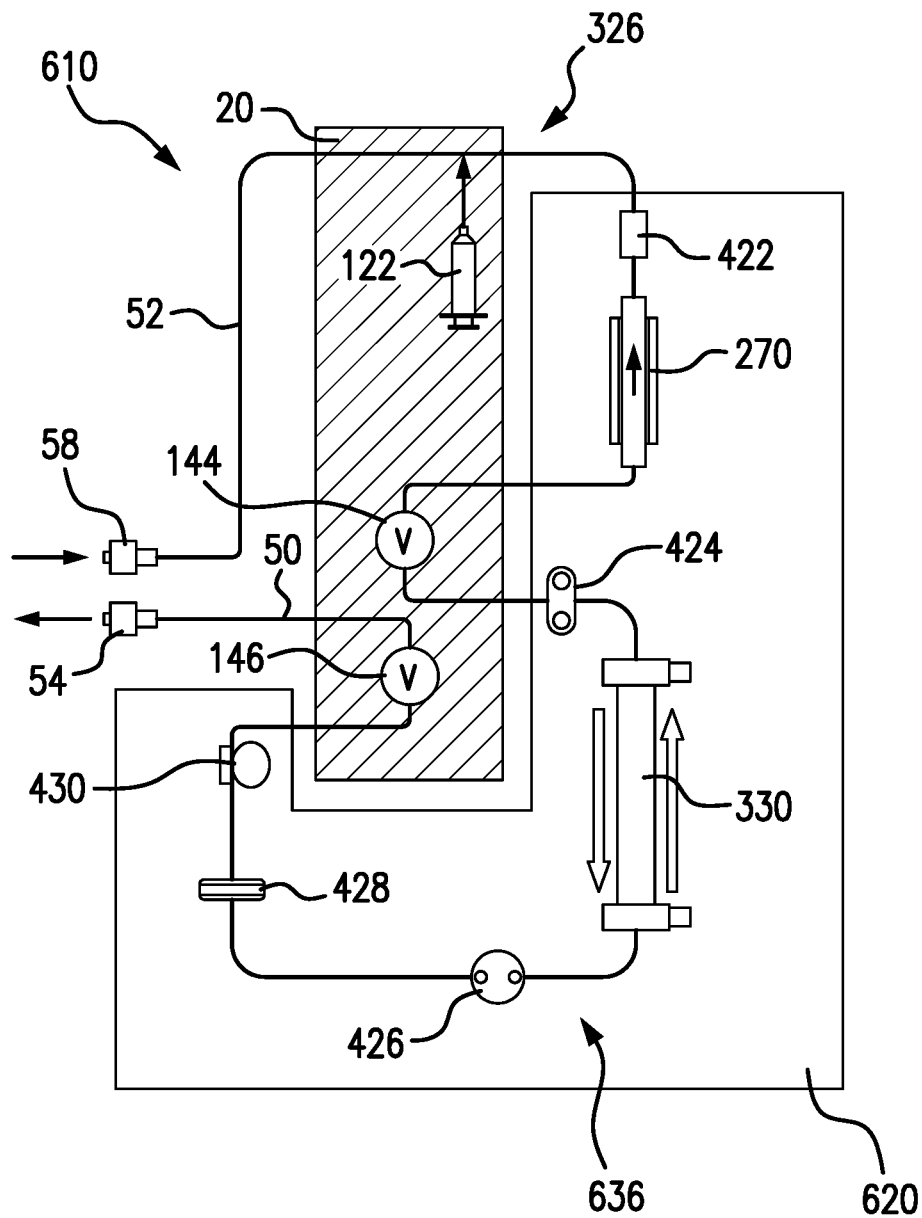
FIG. 8 is a schematic diagram of the modular system shown in FIG. 7.

FIG. 7 is a perspective view of a third modular system 610 including the first portable adapter 20 shown in FIG. 1A mounted on a blood processing apparatus interface 220 (as shown in FIG. 2) of a second portable (blood processing) module 620. FIG. 8 is a schematic diagram of the modular system shown in FIG. 7. The same reference numerals used in FIGS. 7 and 8 that are used in other drawings herein represent the same features. The second portable blood processing module 620 as depicted and described has some of the functionalities shown and described for the first BM 320 and some of the functionalities of the first portable module 520. For example, in addition to just circulating blood, the second portable module 620 is equipped to also filter blood by the inclusion of the blood filter 330. Cross-sectional views of the second portable module 620 are analogous to those shown in FIGS. 3B and 3C. The second portable module 620 can have a second portable housing 622 on which is mounted a second portable handle 624.

The second portable module 620 can be conveyed by any suitable means. For example, one or more wheels may be mounted on second portable housing 622 such as first portable wheels 626, 628, 630, and a fourth wheel not shown. Wheels need not be mounted directly on second portable housing 622. Alternatively, or additionally, second portable module 620 can be placed on a cart or other vehicle for conveyance. A second portable user interface 632 can be provided on second portable housing 622 to enable operation and control of second portable module 620. Alternatively, or additionally, the second portable module 620 can be controlled through the first adapter user interface, though a base module user interface, through a central control station interface, through a personal communications device, or the like. The second portable module 620 can include a second portable power source 634, for example, a rechargeable battery, a fuel cell, a solar cell, or the like.

The second portable blood circuit 636 can function like, and include components identical, similar, or analogous to those described for, the first BM blood circuit 326 shown in FIG. 3A. Blood from a patient can pass through the first adapter blood circuit and through the second portable blood circuit 636. These two circuits can together form a common or grand extracorporeal blood circuit. The second portable housing 622 can include a second portable blood-to-filter exit port 638 and a second portable module blood-from-filter entry port 640. A blood filter entry line 342 and a filter exit line 344 can extend from and to ports 638 and 640, respectively, and to and from the respective entry and an exit ports of blood filter 330. A dialysate entry port 338 and a dialysate exit port 340 can be sealed off, for example, with caps, when blood filter 330 is not used with second portable module 620. The second portable module 620 can be modified to include a dialysate circuit in which case dialysate ports can be provided in second portable housing 622.

Figure 9A:
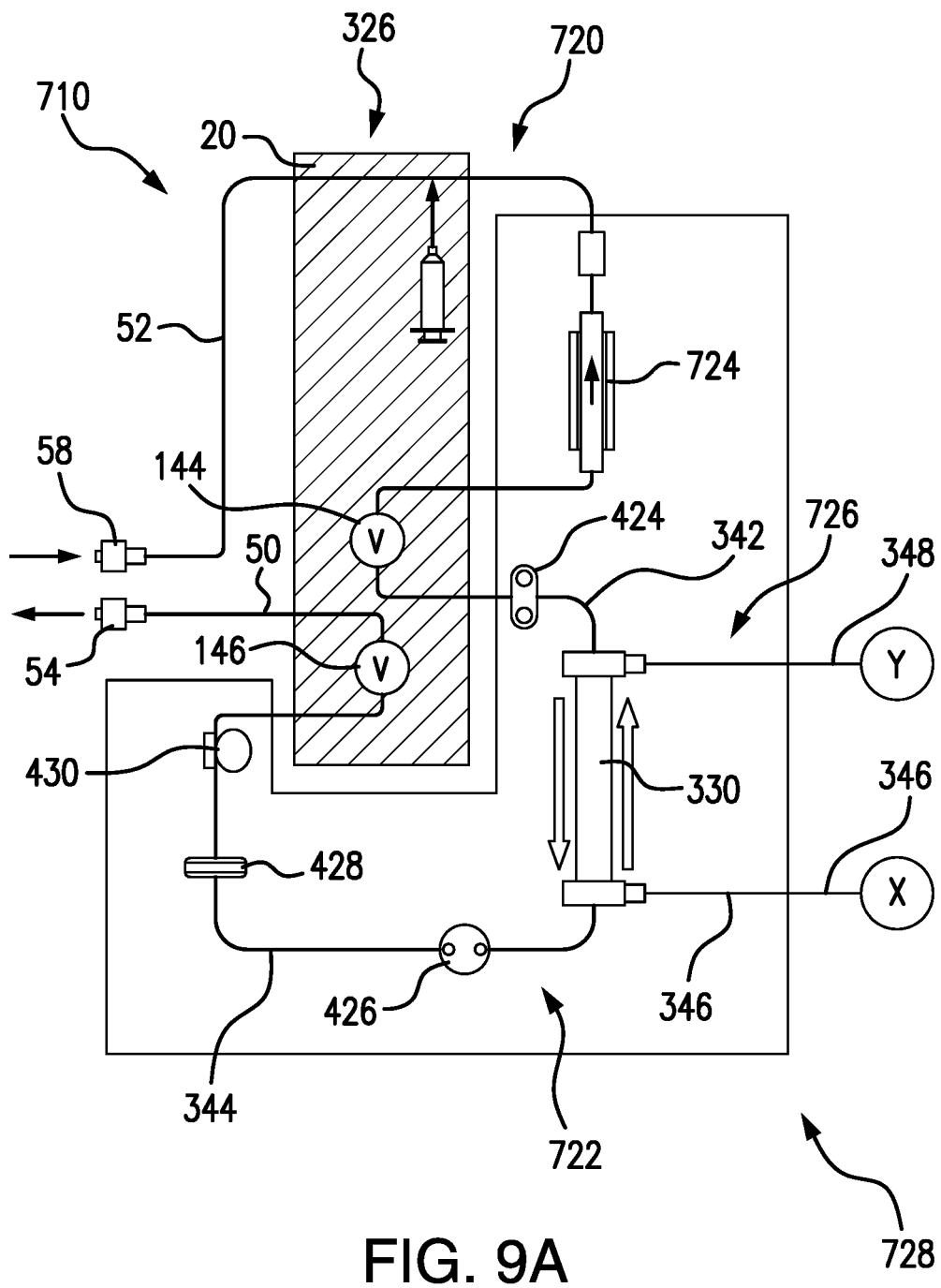
FIG. 9A is a first portion of a schematic diagram of a modular system including the adapter of FIGS. 1A-1H mounted on a first remote module.
Figure 9B:
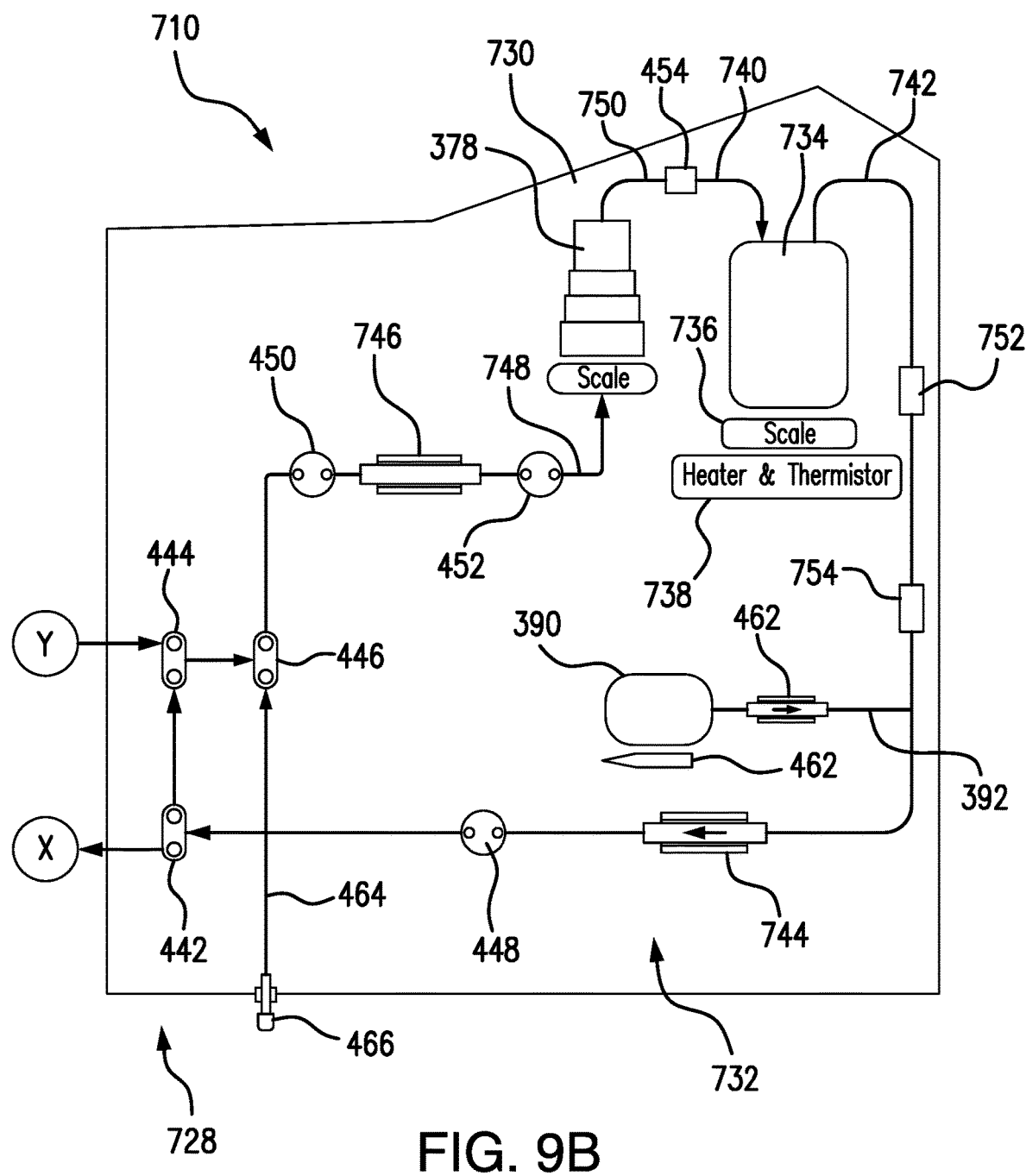
FIG. 9B is a second portion of a schematic diagram of a modular system including a base module.

FIG. 9A is a first portion of a schematic diagram of a fourth modular system 710 that includes the first portable adapter 20 (shown in FIGS. 1A-1H) mounted on a first remote module 720 in accordance with the present invention. FIG. 9B is a second portion of a schematic diagram of the fourth modular system 710 including a first base module 730 in accordance with the present invention. The schematic diagrams of FIGS. 9A and 9B are analogous in many respects to the schematic diagram of FIG. 4. The same reference numerals used in FIGS. 9A and 9B that are used in other drawings herein represent the same features. Indeed, fourth modular system 710 can include components in common with first modular system 310 shown in FIGS. 3A-4. The fourth modular system 710, however, differs in various ways from the first modular system 310, including, but not limited to, separation, sharing, and/or assignment of various components to and between the first remote module 720, the first base module 730, and/or various intermediate systems and subsystems.

The first remote module 720 can include a first remote module (local) blood circuit 722 including a first remote module blood pump 724 and other components as described herein. The first remote module 720 can include a first remote module dialysate circuit 726. A first extended dialysate circuit 728 can connect the first remote module dialysate circuit 726 to the first base module dialysate circuit 732 of the first base module 730. The first base module dialysate circuit 732 can include various components of the first BM dialysate circuit 328 (shown in FIGS. 3A and 4) including, for example, a first base module dialysate reservoir 734, a first base module dialysate weighing subsystem 736, a first base module heater 738, a first base module dialysate reservoir entry line 740, a first base module dialysate reservoir exit line 742, a first base module primary dialysate pump 744, a first base module secondary dialysate pump 746, a first base module sorbent entry line 748, a first base module sorbent exit line 750, a first base module temperature sensor 752, and a first base module conductivity sensor 754.

Figure 10:
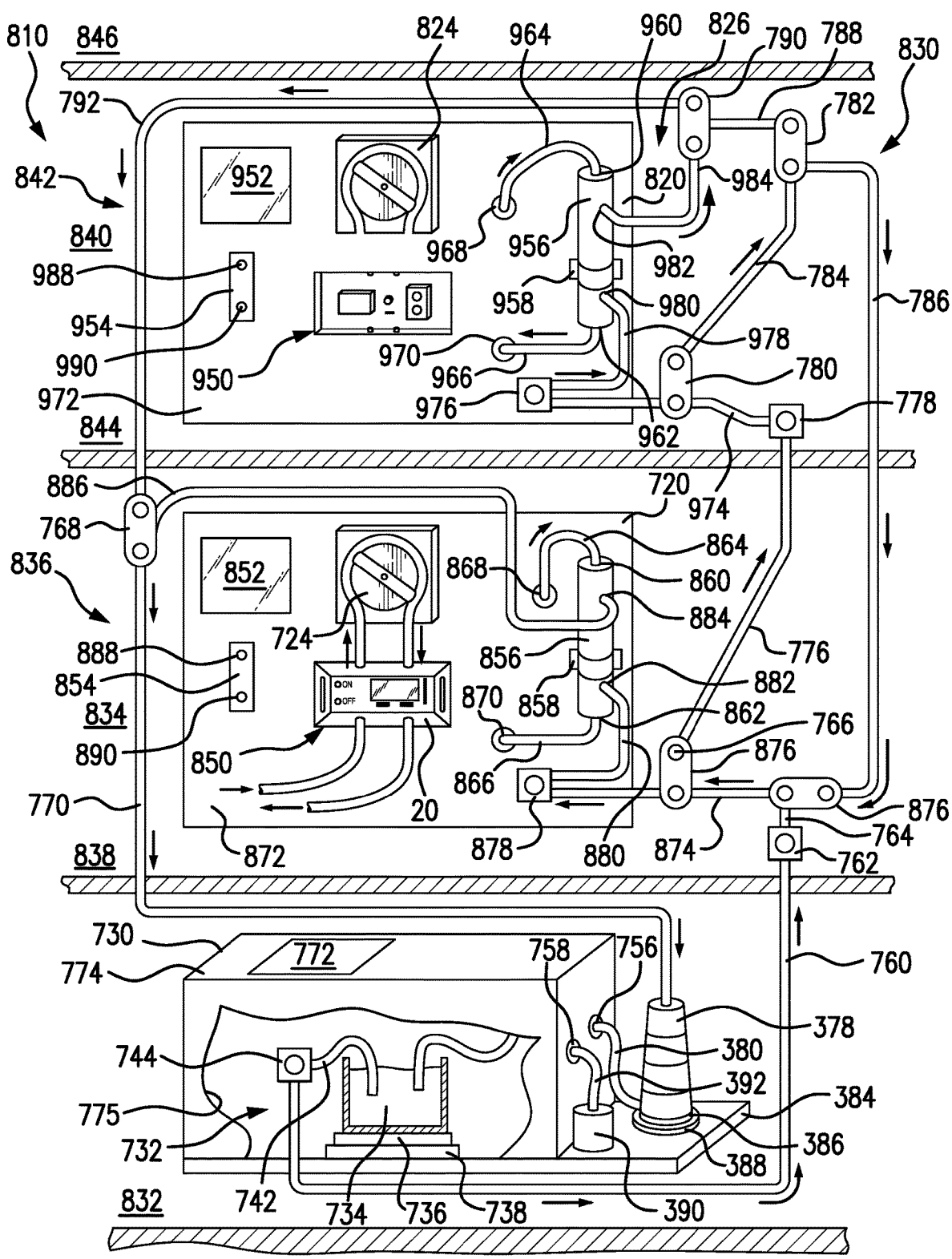
FIG. 10 is a perspective view of a modular system including a base module and two remote modules.

FIG. 10 is a perspective view of a fifth modular system 810 including a first base module 730 and two remote modules 720, 820 in accordance with the present invention. The fifth modular system 810 expands the fourth modular system 710 to include a second remote module 820 and components involved with assisting dialysate flow between the base module 730 and the remote modules 720, 820. The second remote module 820 can include similar or identical components to those of the first remote module 720 (e.g., second remote module (local) blood circuit, a second remote module blood pump 824, and a second remote module dialysate circuit 826). In accordance with the present system, a modular system can be expanded to include any number of base modules and remote modules. The universal nature of the first portable adapter 20 enables it to interact with the remote modules as well as BMs and portable modules of the present invention. Although the base module 730 is not depicted in FIG. 10 with a blood processing apparatus interface or a local blood circuit, it can comprise either or both. For example, base module 730 can be modified to have a configuration similar to the first BM 320 (shown in FIG. 3A). Also, although the remote modules 720, 820 are not shown with independent dialysate supplies, they can be modified to have them. For example, a local dialysate reservoir or bag can be provided in a remote module in case of an interruption of dialysate supply from the base module or another system failure.

The fifth modular system 810 can be arranged in different configurations. For example, base module 730, the first remote module 720, and the second remote module 820 can be located in the same room but spaced apart from one another, in different rooms on the same floor of a building, on two different floors of a building, or in different buildings. This flexibility enables, for example, a patient to begin a blood processing procedure on one floor or room of a building, for example, during the evening, and then complete the procedure after going to bed. In FIG. 10, the fifth modular system 810 is shown spread over three floors of a building 830 including a basement 832, a first floor 838, and a second floor 844. Although the remote modules 720, 820 are shown as wall mounted in FIG. 10, the remote modules 720, 820 can alternatively be located, for example, on the floor, a table, or a cart. The first base module 730 can be located in the basement 832. The first remote module 720 can be located on a first wall 834 in a first room 836 on the first floor 838. The second remote module 820 can be located on a second wall 840 in a second room 842 on the second floor 844. The first base module 730 can, for example, alternatively be located in an attic 846. Locating the base module 730 in an attic or a higher floor than one or more remote modules has the advantage of reducing, minimizing, or eliminating gravity assist products, especially for single pass embodiments in which the dialysate need not be returned to the base module and can be allowed to drain to a lower elevation.

The first remote module 720 can have a first remote module inter-module connector 850 analogous to or including blood processing apparatus interface 220 (shown in FIG. 2). The first remote module 720 can have a first remote module user interface 852. A remote module need not include a separate (local) user interface and can be alternatively or additionally controlled, for example, by a first adapter user interface or by a personal communications device. The first remote module 720 can include a first remote module lock-out unit 854 as part of a lockout system that prevents the second remote module 820 from operating and/or from accepting a first portable adapter 20 when the first portable adapter 20 is mounted on, and/or in operation on the first remote module 720. The first remote module lockout unit 854 can also prevent engagement of the first adapter if the first remote module 720 is out-of-order or dirty or if the fifth modular system 810 is otherwise malfunctioning. The first remote module user interface 852 or another indicator can indicate to a patient which other remote modules are available for use.

The first remote module 720 inclusive of the first remote module (local) blood circuit 722 can have components similar or identical to those of the first BM 320 shown in FIGS. 3A-4 and the first BM blood circuit 326 (FIGS. 3A and 4). For example, a first remote module blood filter 856 can be attached to the first remote module housing 872 with a first remote module blood filter fitting 858. The first remote module blood filter 856 can be a dialyzer. The first remote module blood filter 856 can have a blood entry port 860, a blood exit port 862, and a corresponding blood entry line 864, and the blood exit line 866. These lines can exit and enter through the first remote module-blood-filter exit port 868 and the first remote module blood-from-filter entry port 870.

As depicted in FIGS. 9A and 10, dialysate can be supplied to the first remote module dialysate circuit 726 (FIG. 9A) via a first base module dialysate exit line 760, a first assist dialysate pump 762, a first floor dialysate access line 764, a first floor dialysate bypass valve 766, a first remote module dialysate access line 874, a first floor dialysate access valve 876, and a first remote module dialysate pump 878. Dialysate can travel to the first remote module blood filter 856 via a first remote module filter dialysate entry line 880 through a first remote module filter dialysate entry port 882. Spent dialysate can exit the first remote module blood filter 856 through a first remote module filter dialysate exit port 884 and into the first remote module filter dialysate exit line 886, through the first floor dialysate return valve 768, and then via a primary dialysate return line 770 to return to base module 730. The first base module 730 can include a first base module user interface 772 on a first base module housing 774. Due to the partial cutaway view, a first base module interior 775 is shown including components of the first base module dialysate circuit 732.

As depicted in FIG. 10, dialysate can be supplied to the second remote module dialysate circuit 826 of a second remote module 820 via a first floor dialysate bypass line 776. The second remote module 820 can have a second remote module inter-module connector 950 analogous to the first remote module inter-module connector 850 and/or can include a blood processing apparatus interface. The second remote module 820 can include a second remote module user interface 952 and a second remote module lock-out unit 954 analogous to those described for first remote module 720. A second remote module blood filter 956, which can be, for example, a dialyzer, can be secured using a second remote module blood filter fitting 958. The second remote module blood filter 956 can include a blood entry port 960 and a blood exit port 962 connected to blood entry line 964 and the blood exit line 966, respectively. These lines can pass through a second remote module-blood-filter exit port 968 and a second remote module blood-from-filter entry port 970, respectively, in the second remote module housing 972.

Dialysate can flow to the second remote module dialysate circuit 826 via a second assist dialysate pump 778, a second floor dialysate primary bypass valve 780, a second remote module dialysate access line 974, a second remote module dialysate pump 976, a second remote module filter dialysate entry line 978, and into a second remote module filter dialysate entry port 980 of the second remote module blood filter 956. Spent dialysate can exit through a second remote module filter dialysate exit port 982 and pass through a second remote module filter dialysate exit line 984 to a second floor dialysate return valve 790, through a second floor dialysate return line 792, through first floor dialysate return valve 768, through primary dialysate return line 770, and back to the first base module 730.

The lock-out system of the fifth modular system 810 can include various indicators to aid a patient. For example, a remote module lockout unit 854 can include a remote module availability indicator 888 and a remote module lock-out indicator 890 to indicate whether or not the first remote module 720 is available for blood processing procedures. A second remote module lock-out unit 954 can similarly include a remote module availability indicator 988 and a remote module lock-out indicator 990 to indicate whether or not the second remote module 820 is available for blood processing procedures The second-floor dialysate primary bypass valve 780 can divert dialysate from the second remote module 820 back to the first base module 730 or to the first remote module 720 when used in combination with the second-floor dialysate secondary bypass valve 782. Dialysate can flow between those two valves via a second-floor dialysate bypass line 784. Dialysate can flow down to the first floor via a primary dialysate bypass line 786 or through an auxiliary dialysate return line 788 to the second-floor dialysate return valve 790.

Figure 11C:
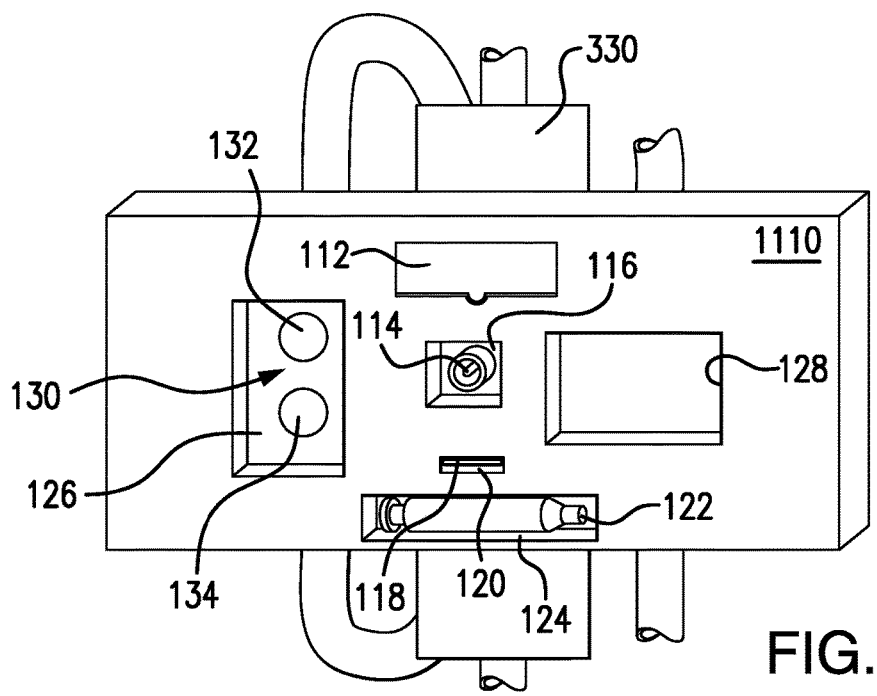
FIG. 11C is a bottom view of the adapter shown in FIGS. 11A and 11B.
Figure 11D:
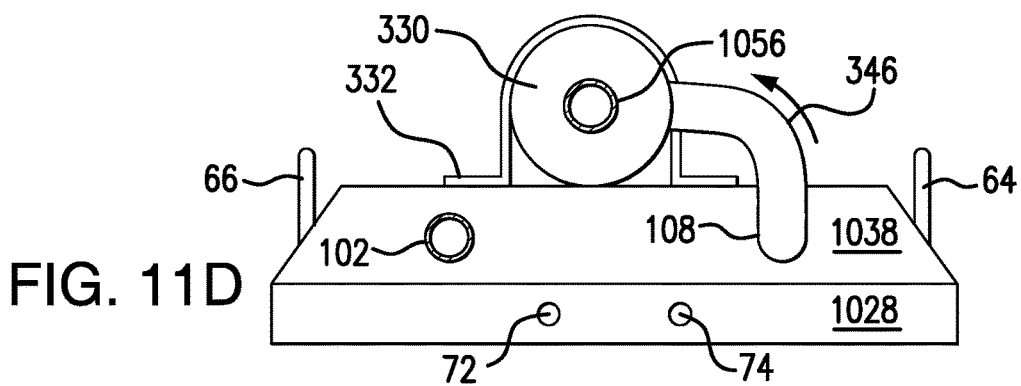
FIG. 11D is a front view of the adapter shown in FIGS. 11A-11C.
Figures 11E, 11F:
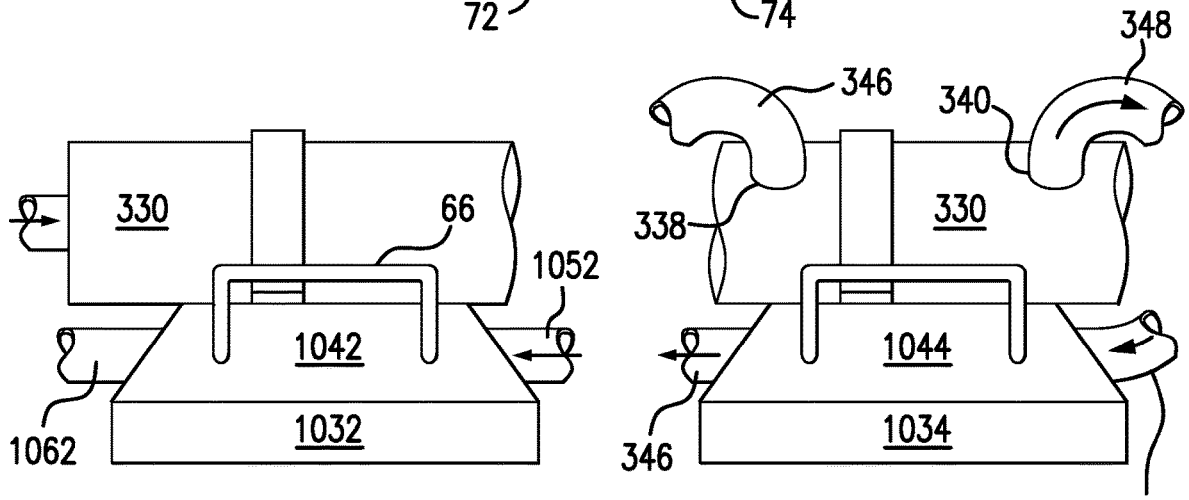
FIG. 11E is a left side view of the adapter shown in FIGS. 11A-11D.
FIG. 11F is a right-side view of the adapter shown in FIGS. 11A-11E.

FIG. 11A is a perspective view of a second (portable dialysate circuit) adapter 1020 configured to engage with a second BM such as the second BM 1320 shown in FIG. 11A, or to engage with a portable module through a blood processing apparatus interface such as 220 (shown in FIG. 2). FIG. 11B is a top (plan) view of the adapter shown in FIG. 11A. FIG. 11C is a bottom view of the adapter shown in FIG. 11A. FIG. 11D is a front view of the adapter shown in FIG. 11A. FIG. 11E is a left side view of the adapter shown in FIG. 11A. FIG. 11F is a right side view of the adapter shown in FIG. 11A. The second adapter 1020 is similar in design to the first portable adapter 20 shown in FIGS. 1A-1H but has been configured for connection to a blood processing apparatus via a dialysate circuit instead of via a blood circuit. The second adapter 1020, however, can be modified in ways described for modification of the first portable adapter 20, and vice versa. A user interface has been omitted and the data ports are arranged to enable the inclusion and attachment of blood filter 330.

The second adapter 1020 has a second adapter housing 1022 including a second adapter housing base 1024 and a second adapter housing body 1026. The second adapter housing base 1024 includes second adapter housing lateral sides (front, back, left, right) 1028, 1030, 1032, and 1034. The second adapter housing body 1026 includes the second adapter housing sloped sides (front, back, left, right) 1038, 1040, 1042, and 1044. The second adapter 1020 includes a second adapter housing top surface 1046. A second blood line set 1048 passes through a second adapter housing body 1026. The second blood line set 1048 can include a second venous line 1050 with a patient end 1054 and a dialyzer end 1056, a second arterial line 1052 with a patient end 1058 and an adapter end 1060, and a second engagement loop 1062. In contrast to the first adapter blood pump the engagement loop 62, the second engagement loop 1062 is connected to the blood filter 330 instead of to the second adapter housing body 1026.

The blood filter 330 can be secured to the second adapter housing top surface 1046 through blood filter fitting 332 or by using another suitable device. A curved recess can optionally be set in second adapter housing top surface 1046 to more stably secure the blood filter 330 and to prevent or minimize wobbling and rotation of the filter. The second adapter housing top surface 1046 also can include a second adapter first data port 1090 and second adapter second data port 1092, as well as second adapter card reader 1094. The second adapter blood circuit can include second blood line set 1048 and blood filter 330. As indicated, second blood line set 1048 can pass through a second adapter housing body 1026. The second adapter-arterial linearterial line 1052 passes through the first port 102 (FIG. 11B). The second tubing blood pump engagement loop 1062 connects the second port 104 to the blood filter 330 through a blood entry port. The second adapter-venous line 1050 extends from filter blood exit port in connection with the second adapter-venous line dialyzer end 1056. The dialysate entry line 346 extends from the fourth port 108 to the dialysate entry port 338 of blood filter 330. Dialysate exit line 348 extends from the dialysate exit port 340 to the third port 106. The second adapter bottom surface 1110 is analogous to the first bottom surface 110 shown in FIG. 1C. Fresh or regenerated dialysate can enter the second adapter 1020 through the entry port 134 and spent dialysate can exit through the exit port 132.

Figure 12:
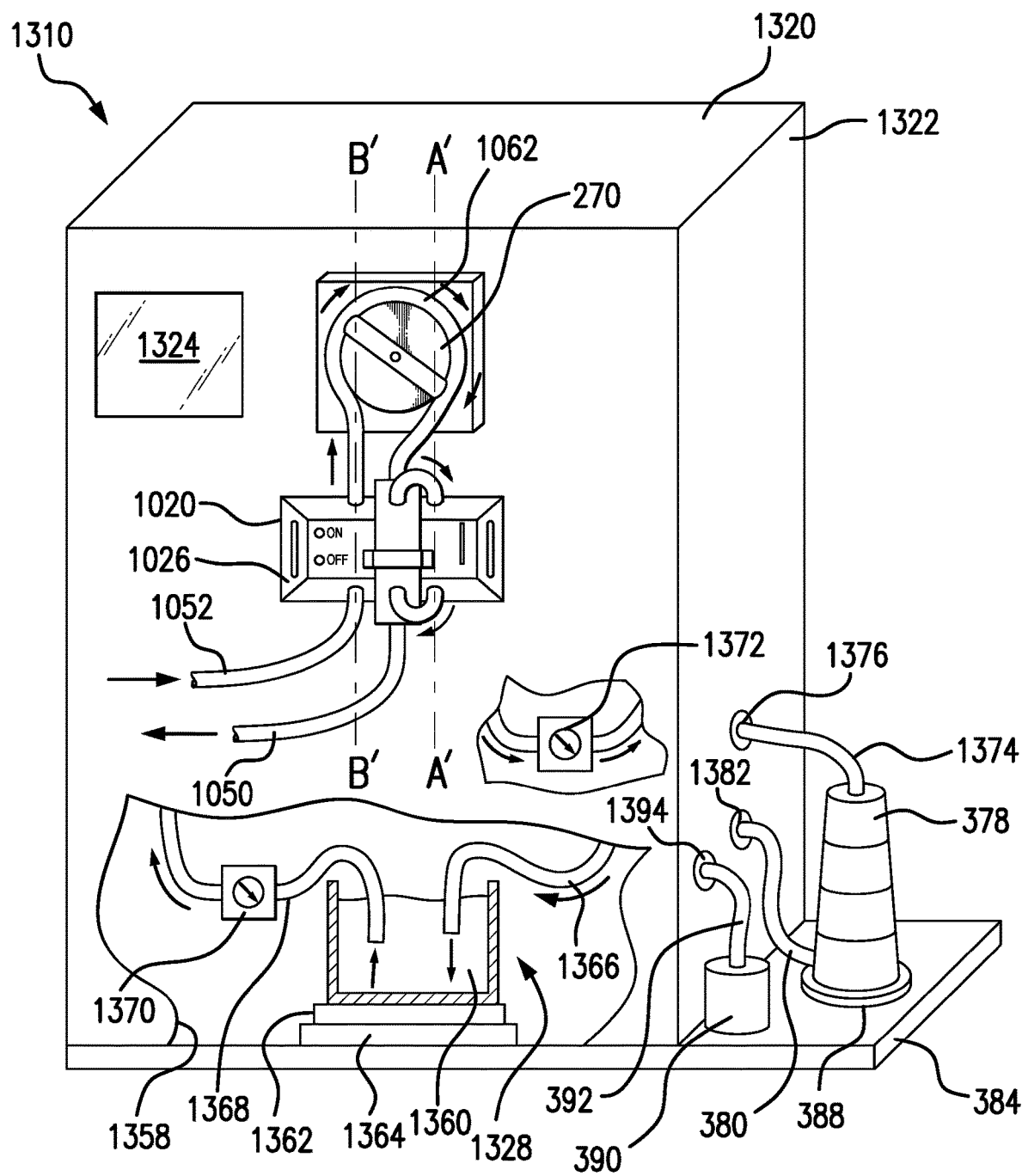
FIG. 12 is a perspective view of a modular system including a BM and the adapter of FIGS. 11A-11F connected to the blood processing apparatus interface of FIG. 2.
Figure 13:
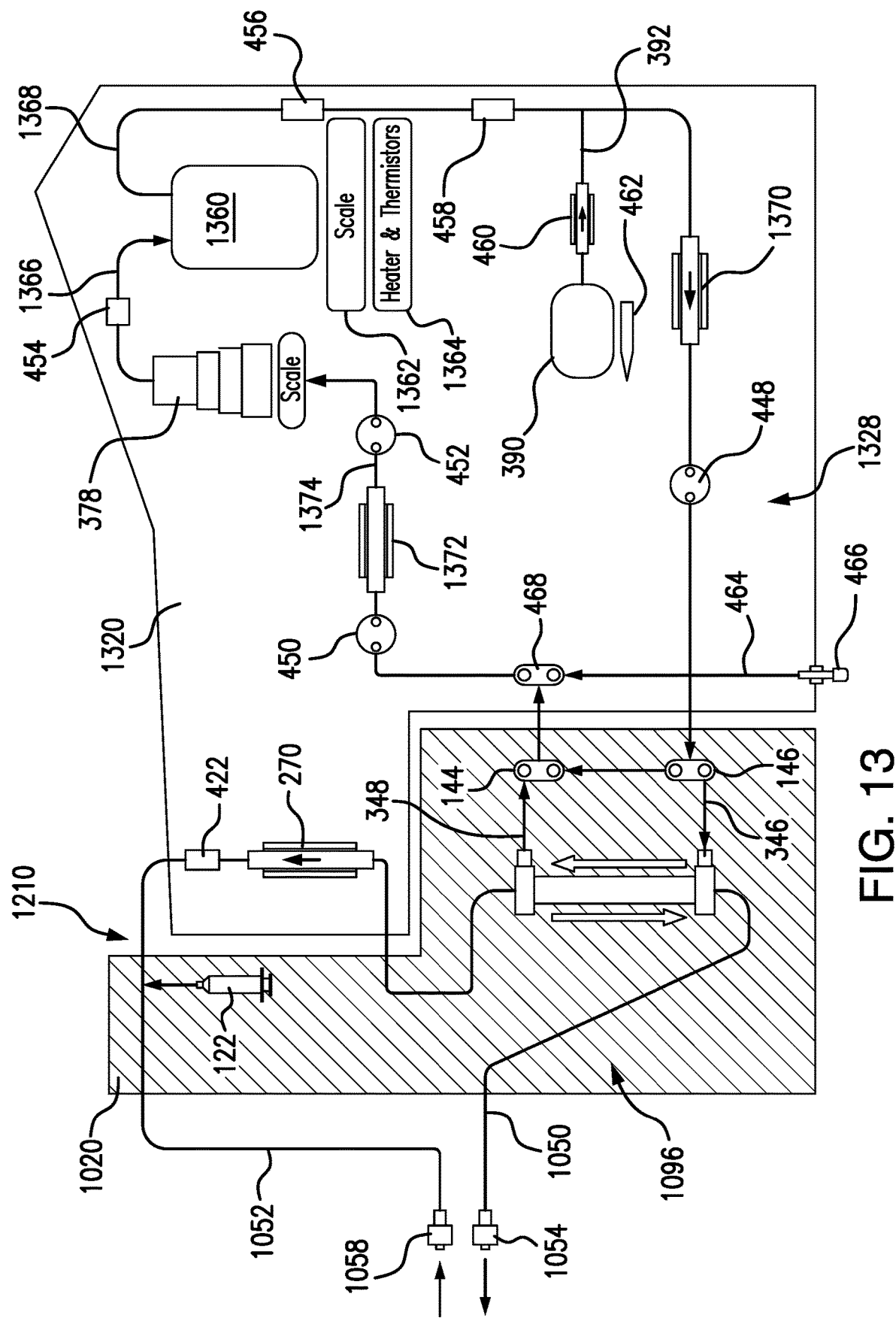
FIG. 13 is a schematic diagram of the modular system shown in FIG. 12.

FIG. 12 is a perspective view of a sixth modular system 1310 including second adapter 1020 shown in FIGS. 11A-11F mounted on a blood processing apparatus interface such as 220 shown in FIG. 2, but of a second BM 1320 through a modular interface. FIG. 13 is a schematic diagram of sixth modular system 1310. Reference numerals in FIGS. 12 and 13, which also appear in other drawings herein, represent the same or similar components. Sixth modular system 1310 is similar in some aspects to the first modular system 310 shown in FIGS. 3A-3C. The second BM 1320 is also similar in some aspects to the first BM 320 shown in FIGS. 3A-3C and can share similar components. Differences can include, for example, compartmentalization of the extracorporeal blood flow to the second adapter blood circuit.

The second BM 1320 can include a second BM housing 1322 on which a second BM user interface 1324 is located. Alternative or additional user interfaces can be used as described for first BM 320 shown in FIGS. 3A-3C. The second BM 1320 can have a second BM dialysate circuit 1328 that complements and/or completes a dialysate circuit or partial circuit of second adapter 1020. The second BM dialysate circuit 1328 is visible, in part, through the cutaway in FIG. 12 that depicts second BM interior 1358. The second BM dialysate circuit 1328 can include, for example, components from or analogous to those of the first BM dialysate circuit 328 shown in FIG. 3A. The second BM dialysate circuit 1328 can include, for example, a second BM dialysate reservoir 1360, a second BM dialysate weighing subsystem 1362, a second BM heater 1364, a second BM dialysate reservoir entry line 1366, a second BM dialysate reservoir exit line 1368, a second BM primary dialysate pump 1370, a second BM secondary dialysate pump 1372, a second BM sorbent entry line 1374, an electrolyte supply 390, and an electrolyte line 392. The second BM housing 1322 can include a second BM dialysate-to-sorbent exit port 1376, a second BM dialysate-from-sorbent entry port 1382, and a second BM electrolyte entry port 1394 to enable ingress and egress of fluid through these lines. Although second BM 1320 is depicted as a sorbent/regenerative-type system, this is for exemplary purposes only and the module can instead be provided, for example, as a single-pass-type system.

FIG. 14 is a perspective view of a third portable (blood processing) module 1520 configured to dock with a BM in accordance with the present invention. The third portable module 1520 can have a third portable module housing 1522 including a third portable module horizontal section 1524 and a third portable module vertical section 1526. The third portable module horizontal section 1524 can include a third portable module overhang 1528. The third portable module vertical section 1526 can include a third portable module bottom surface 1530. A third portable module tripod base 1532 can be positioned on third portable module bottom surface 1530 including a third portable module first wheel 1534, a third portable module second wheel 1536, and a third portable module leg stand 1538. A third portable module back surface 1540 can provide an additional or alternative means for conveyance by providing a first back strap 1542 and a second back strap 1543. These straps enable third portable module 1520 to be carried as a backpack by a patient.

A third portable module blood exit port 1544 and a third portable module blood entry port 1546 in a third portable module housing 1522 enable ingress and egress of fluid through a third blood line set 1548 through third portable module back surface 1540. The third blood line set 1548 can include a third venous line 1550, a third portable module arterial line 1552, a third portable module venous line patient end 1554, a third portable module venous line adapter end 1556, a third portable module arterial line patient end 1558, and a third portable module arterial line adapter end 1560. The third portable module venous line 1550 extends from third portable module blood exit port 1544, and third portable module arterial line 1552 extends from third portable module blood entry port 1546. The third portable module blood exit port 1544 and third portable module blood entry port 1546 can instead be located on a different surface, for example, on a third portable module top surface 1562.

The third portable module top surface 1562 can include various components. A third portable module handle 1564 can extend from the third portable module top surface 1562 and can, for example, be in the form of an extendible/retractable luggage handle. The third portable module 1520 can have an inter-module locking system analogous to the locking system 70 shown in FIG. 1A. The inter-module locking system can take the form of a bolt-actuator system, but this is for exemplary purposes only as any suitable type of locking system can be used or such a system can be omitted altogether. The inter-module locking system can include, for example, a module first bolt hole 1572, a module second bolt hole 1574, a module third bolt hole (not shown), and a module fourth bolt hole (not shown) extending into the third portable module overhang 1528. A portable module engagement verification subsystem 1580 (analogous to the adapter engagement verification subsystem 80 shown in FIGS. 1A-1H) can be provided on the third portable module top surface 1562 including a portable module engagement first detectable signal LED 1582 and a portable module engagement second detectable signal LED 1584. The third portable module top surface 1562 can also include a third portable module user interface 1586 analogous to the user interface 86 shown in FIGS. 1A-1H. The third portable module user interface 1586 can be omitted, however, if a BM user interface or a personal communications device user interface is used instead. The third portable module top surface 1562 can further include one or more of a third portable module first data port 1590, a third portable module second data port 1592, and a third portable module card reader 1594, analogous to the first data port 90, the first second data port 92, and the first card reader 94 shown in FIGS. 1A-1H.

Figure 15:
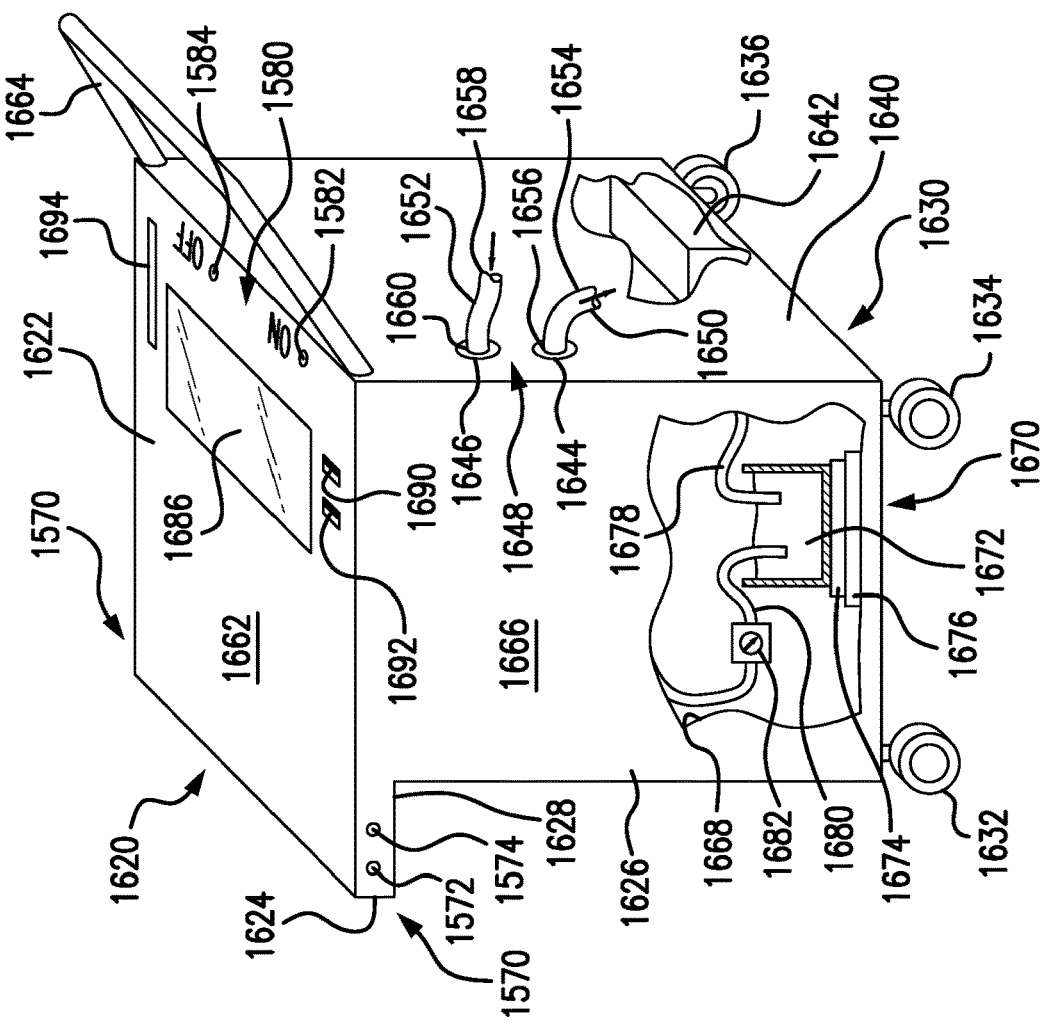
FIG. 15 is a perspective view of another portable module configured to dock with a BM.

Power can be supplied to the third portable module 1520, for example, directly from an AC power outlet, indirectly through a power cable, indirectly through an interface with a blood processing apparatus, or from another source. As visible through the cutaway view is shown in FIG. 15, in a third portable module lateral surface 1596, a third portable module power source 1598 can be included that is analogous to the first portable power source 534 shown in FIG. 5A. The third portable module power source 1598 can be, for example, a rechargeable battery, a fuel cell, a solar cell, or the like. For embodiments including a solar cell, a solar panel in electrical or optical communication with the solar cell can be provided on one or more surfaces of the module housing.

FIG. 15 is a perspective view of a fourth portable (blood processing) module 1620 configured to dock with a BM in accordance with the present invention. The fourth portable module 1620 is similar to the third portable module 1520 shown in FIG. 14, however, its larger size enables inclusion of additional components, functionalities, and systems. The fourth portable module 1620 can include a fourth portable module housing 1622. The fourth portable module housing 1622 can include a fourth portable module horizontal section 1624 and a fourth portable module vertical section 1626. The fourth portable module horizontal section 1624 can include fourth portable module overhang 1628. The fourth portable module vertical section 1626 can include a fourth portable module bottom surface 1630. A fourth portable module first wheel 1632, a fourth portable module second wheel 1634, a fourth portable module third wheel 1636, and a fourth portable module fourth wheel (not shown) can be mounted on fourth portable module bottom surface 1630. Alternatively, fourth portable module 1620 can be conveyed on a cart or on another vehicle.

The fourth portable module 1620 can have a fourth portable module back surface 1640. The cutaway view of fourth portable module back surface 1640 shows a fourth portable module power source 1642 analogous to the third portable module power source 1598 shown in FIG. 14. Power can be supplied to the fourth portable module 1620 as described for the third portable module 1520 (FIG. 14). A fourth portable module blood exit port 1644 and a fourth portable module blood entry port 1646 in the fourth portable module housing 1622 enable ingress and egress of fluid through a fourth blood line set 1648. The fourth portable module blood exit port 1644 and fourth portable module blood entry port 1646 can be located, for example, on fourth portable module back surface 1640. The fourth blood line set 1648 is analogous to the third blood line set 1548 shown in FIG. 15 and can include a fourth portable module venous line 1650, a fourth portable module arterial line 1652, a fourth portable module venous line patient end 1654, a fourth portable module venous line adapter end 1656, a fourth portable module arterial line patient end 1658, and a fourth portable module arterial line adapter end 1660.

The fourth portable module 1620 can include a fourth portable module top surface 1662. A fourth portable module handle 1664 can extend from fourth portable module back surface 1640 and/or from fourth portable module top surface 1662. The cutaway view of fourth portable module lateral surface 1666 reveals a fourth portable module interior 1668 wherein a fourth portable module dialysate circuit 1670 is visible, in part, including a fourth portable module dialysate reservoir 1672, a fourth portable module dialysate weighing subsystem 1674, a fourth portable module heater 1676, a fourth portable module dialysate reservoir entry line 1678, a fourth portable module dialysate reservoir exit line 1680, and a fourth portable module dialysate pump 1682.

Portable module engagement verification subsystem 1580 (analogous to the adapter engagement verification subsystem 80 shown in FIGS. 1A-1H) can be provided on fourth portable module top surface 1662 including portable module engagement first detectable signal LED 1582 and portable module engagement second detectable signal LED 1584. The fourth portable module top surface 1662 can also include a fourth portable module user interface 1686 analogous to the user interface 86 (shown in FIGS. 1A-1H) and analogous to the third portable module user interface 1586

(shown in FIG. 15). The fourth portable module top surface 1662 can further include one or more of a fourth portable module first data port 1690, a fourth portable module second data port 1692, and a fourth portable module card reader 1694, analogous to the first data port 90, the first second data port 92, and the first card reader 94 shown in FIGS. 1A-1H.

Figure 16A:
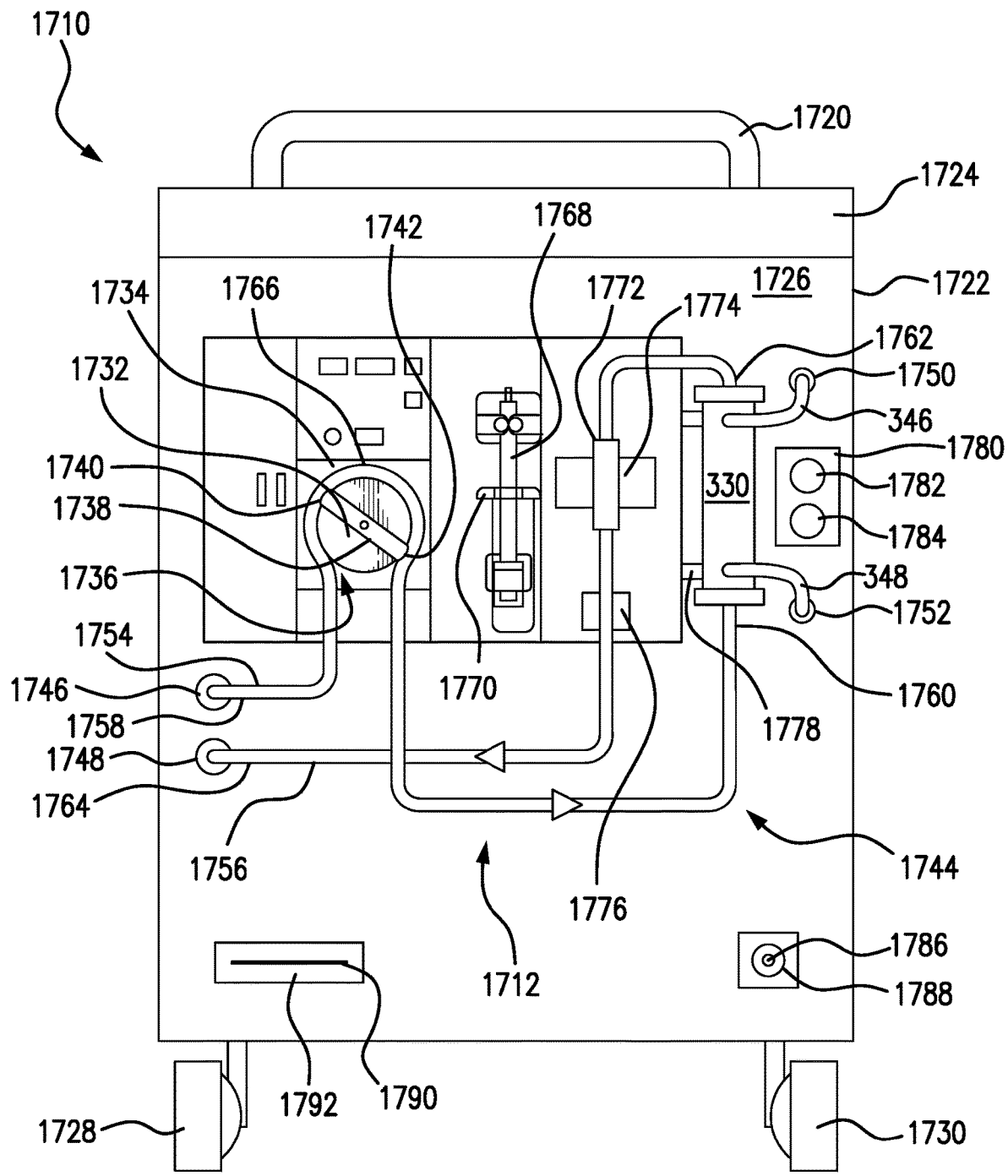
FIG. 16A is a front view of a portable module similar to that shown in FIG. 14 or FIG. 15 and shows a blood processing apparatus interface configured to engage with a BM through a dialysate circuit.

FIG. 16A is a front view of a portable-module-dialysate-connect interface 1710 configured to engage with a BM through a dialysate circuit. The portable-module-dialysate-connect interface 1710 includes a portable module blood circuit 1712, which can correspond to or include the third or fourth blood line sets 1548, 1648 shown in FIGS. 14 and 15, respectively. FIG. 16A also shows a portable module handle 1720 and a portable module housing 1722. A portable module first wheel 1728 and a portable module second wheel 1730 are also provided.

The portable-module-dialysate-connect interface 1710 can include a portable module horizontal portion front surface 1724 and a portable module vertical portion front surface 1726. The portable-module-dialysate-connect interface 1710 can include, for example, features described for the first bottom surface 110 (FIG. 1C) and for the blood processing apparatus interface 220 (FIG. 2). For example, portable-module-dialysate-connect interface 1710 can include a portable module blood pump 1732, portable module pump frame 1734, a portable tubing loop engagement track 1736, portable blood pump rotor 1738, a portable module first blood pump head 1740, and a portable module second blood pump head 1742. A portable-module-extracorporeal-blood-circuit-tubing set 1744 is provided and can correspond to the third or the fourth blood line sets 1548, 1648 of FIGS. 14 and 15, respectively. The blood line set 1744 can pass through portable module vertical portion front surface 1726 at portable module front service arterial exit port 1746, portable module front surface venous entry port 1748, as well as connecting to the blood filter 330. The portable-module-extracorporeal-blood-circuit-tubing set 1744 can include a portable module arterial line 1754, a portable module venous line 1756, a portable module arterial line first end 1758, a portable module arterial line second end 1760, a portable module venous line first end 1762, a portable module venous line second end 1764, and a portable module tubing blood pump engagement loop 1766. Portable module tubing blood pump engagement loop 1766 can be received by portable tubing loop engagement track 1736. A portable module first tube port 1750 and a portable module second tube port 1752 in portable module vertical portion front surface 1726 receive dialysate entry line 346 and dialysate exit line 348, which are also connected to the blood filter 330, enabling the flow of dialysate to and from the filter.

A portable module front surface anticoagulant supply 1768 can be attached to portable module vertical portion front surface 1726 by a portable module front surface anticoagulant supply receptacle 1770. The portable module blood circuit 1712 and/or the portable-module-extracorporeal-blood-circuit-tubing set 1744 can include a portable module front surface drip chamber 1772 held to portable module vertical portion front surface 1726 by a portable module drip chamber receptacle 1774. A portable module front surface drip chamber valve 1776 on portable module vertical portion front surface 1726 can be in operable communication with portable-module-extracorporeal-blood-circuit-tubing set 1744. The blood filter 330 can be held to portable module vertical portion front surface 1726 by a portable module blood filter fitting 1778. A portable module inter-module connector 1780 can be recessed in or otherwise located on or above portable module vertical portion front surface 1726. The portable module inter-module connector 1780 can function in a manner analogous to the inter-module connector 130 (FIG. 11C) in second adapter 1020 (FIG. 11A). The portable module inter-module connector 1780 can include a portable module exit port 1782 and a portable module entry port 1784 analogous to the exit port 132 and the entry port 134 (FIG. 11C) in the second adapter 1020, enabling the flow of dialysate between the portable module and a BM. A portable module power connector 1786 can be located in a portable module power connector recess 1788, and a portable module data connector 1790 can be located in a portable module data connector recess 1792 in portable module vertical portion front surface 1726. A common power/data connector can be used instead of or in addition to separate power and data connectors. Portable module horizontal portion front surface 1724, portable module vertical portion front surface 1726, and or other module surfaces can be treated with one or more antimicrobial compounds, compositions, films, particles, or the like to minimize or prevent contamination.

Figure 16B:
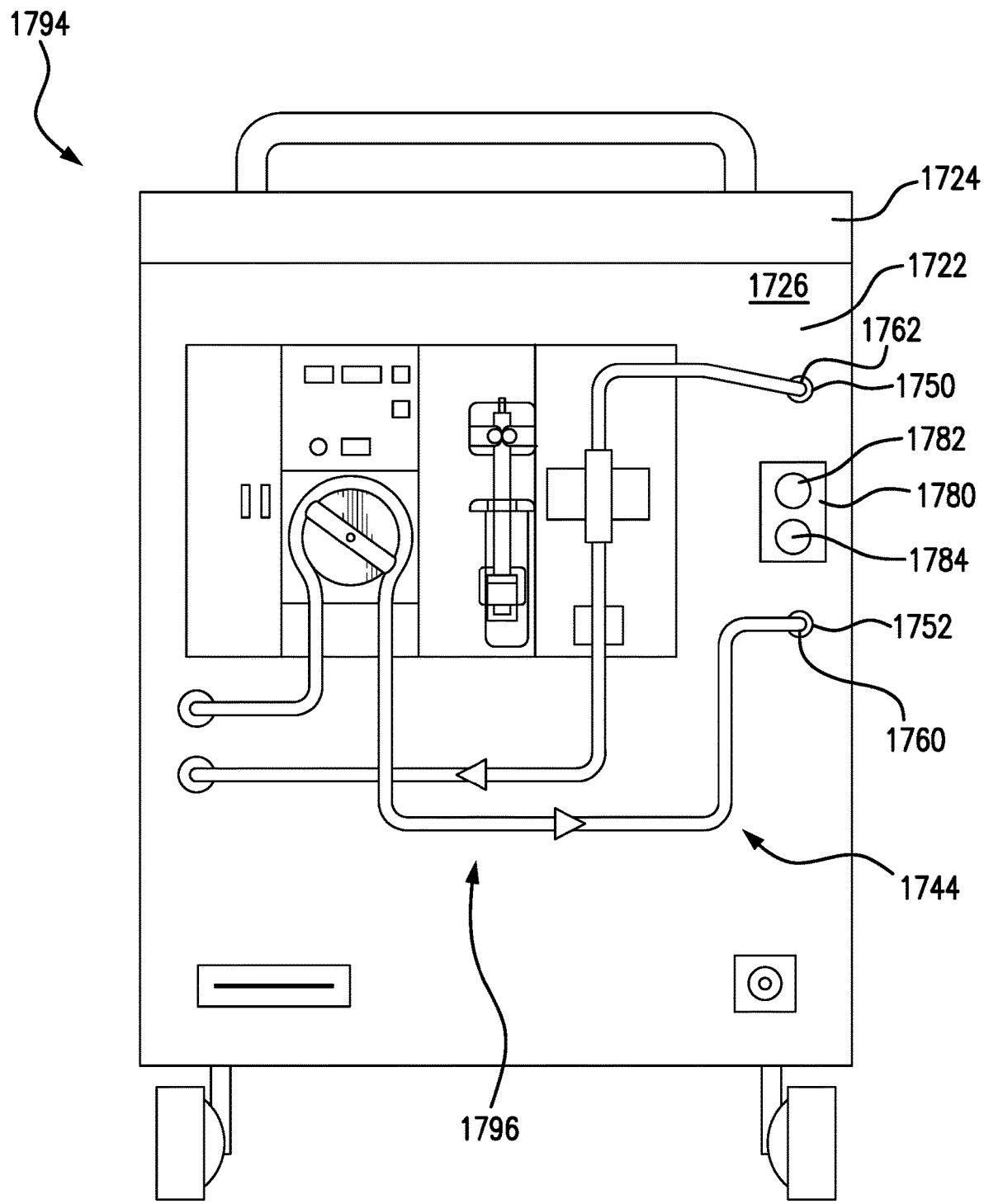
FIG. 16B is a front view of a portable module similar to that shown in FIG. 14 or FIG. 15 and shows another blood processing apparatus interface configured to engage with a BM through a blood circuit.

FIG. 16B is a front view of a portable module such as shown in FIG. 14 or 15 and showing a portable module blood connect interface 1794 configured to engage with a BM. Portable module blood connect interface 1794 can include a portable module blood connect blood circuit 1796. Portable module blood connect interface 1794 is similar to the portable-module-dialysate-connect interface 1710 (FIG. 16A) in some respects but can differ in various respects including, for example, omitting blood filter 330. The portable module blood connect interface 1794 can include portable-module-extracorporeal-blood-circuit-tubing set 1744 in which portable module arterial line second end 1760 is connected to portable module second tube port 1752 and portable module venous line first end 1762 is connected to portable module first tube port 1750. Portable module inter-module connector 1780 can function in a manner analogous to the inter-module connector 130 in the first portable adapter 20 (FIG. 11C). The portable module exit port 1782 and portable module entry port 1784 can function analogous to the exit port 132 and the entry port 134 in the first portable adapter 20 (FIG. 1C) thereby enabling blood flow between the portable module and a BM.

Figure 17A:
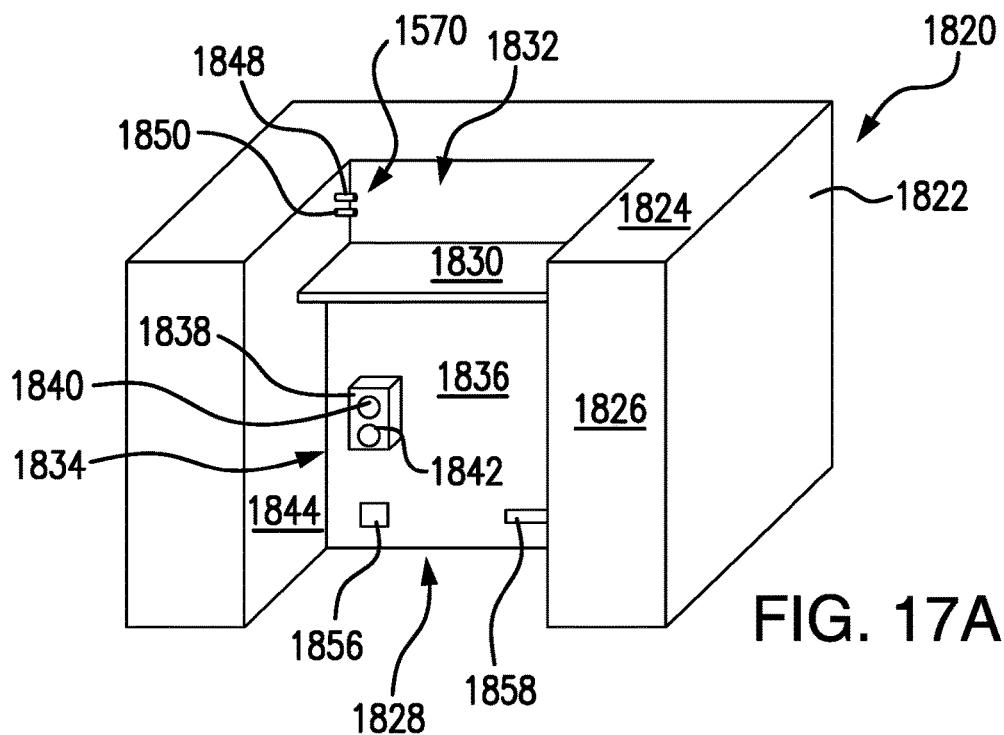
FIG. 17A is a right, top perspective view of a BM configured to dock a portable module.
Figure 17B:
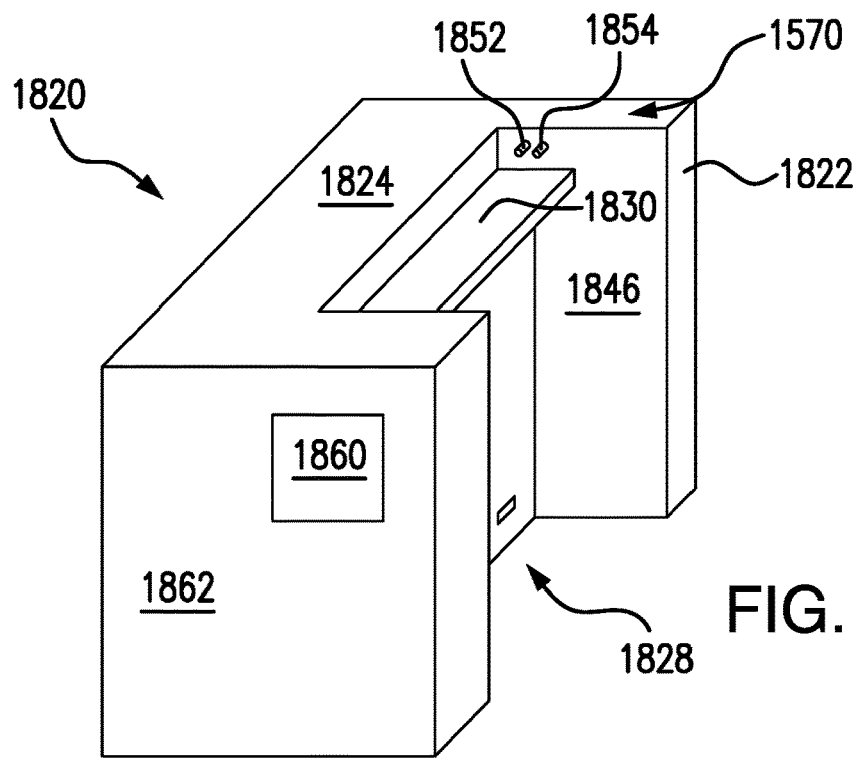
FIG. 17B is a left, top perspective view of the BM shown in FIG. 17A.

FIG. 17A is a right perspective view of a third BM 1820 configured to dock a portable module and demonstrates a closure system. The third BM 1820 can dock, for example, third portable module 1520 (FIG. 14) or fourth portable module 1620 (FIG. 15). FIG. 17B is a left perspective view of third BM 1820 shown in FIG. 17A. The third BM 1820 can include a third BM housing 1822, a third BM top surface 1824, and a third BM front surface 1826. A universal BM dock (receptacle) 1828 is recessed into the third BM top surface 1824 and third BM front surface 1826. The universal BM dock 1828 can include a BM dock shelf 1830 that divides the universal BM dock 1828 into a BM upper bay 1832 and a BM lower bay 1834, and is configured to support a portable module overhang, for example, third portable module overhang 1528 (FIG. 14) or fourth portable module overhang 1628 (FIG. 15).

The universal BM dock 1828 can include a BM bay front surface 1836. A BM complementary inter-module connector 1838 can protrude from or otherwise be positioned on or in BM bay front surface 1836. A BM complementary inter-module connector 1838 can be complementary to portable module inter-module connector 1780 of FIG. 16A or 16B. Those two connectors can connect directly or through one or more connecting lines and/or other components. A BM complementary inter-module connector 1838 can be analogous to complimentary inter-module connector 250 of blood processing apparatus interface 220 (shown in FIG. 2). A BM complementary inter-module connector 1838 can include BM entry port 1840 and BM exit port 1842, which can be analogous to the entry port 252 and an exit port 254 (shown in FIG. 2). Thus, these components demonstrate a closure system in accordance with the present invention.

The universal BM dock 1828 can include a first lateral surface 1844 and a second lateral surface 1846. These lateral surfaces can include retractable bolts that engage bolt holes located on a docked portable module to form an inter-module locking system 1570. The first lateral surface 1844 can include a first retractable bolt 1848 and a second retractable bolt 1850. The second lateral surface 1846 can include a third retractable bolt 1852 and a fourth retractable bolt 1854. These bolts can retract to allow a portable module to engage a third BM 1820 and then extend to secure the portable module in place.

A BM bay front surface 1836 can include BM complementary power connector 1856 and BM complementary data connector 1858, which can engage with portable module power connector 1786 and portable module data connector 1790, respectively, of the portable module shown in FIG. 16A. A common complementary power/data connector can be used instead of, or in addition to, separate complementary power and data connectors. A third BM outer lateral surface 1862 can include a third BM (primary) user interface 1860. The third BM user interface 1860 is shown as a touch screen but can take the form of other types of user interfaces. The third BM user interface 1860 can be positioned differently on third BM housing 1822 or omitted.

Figure 18A:
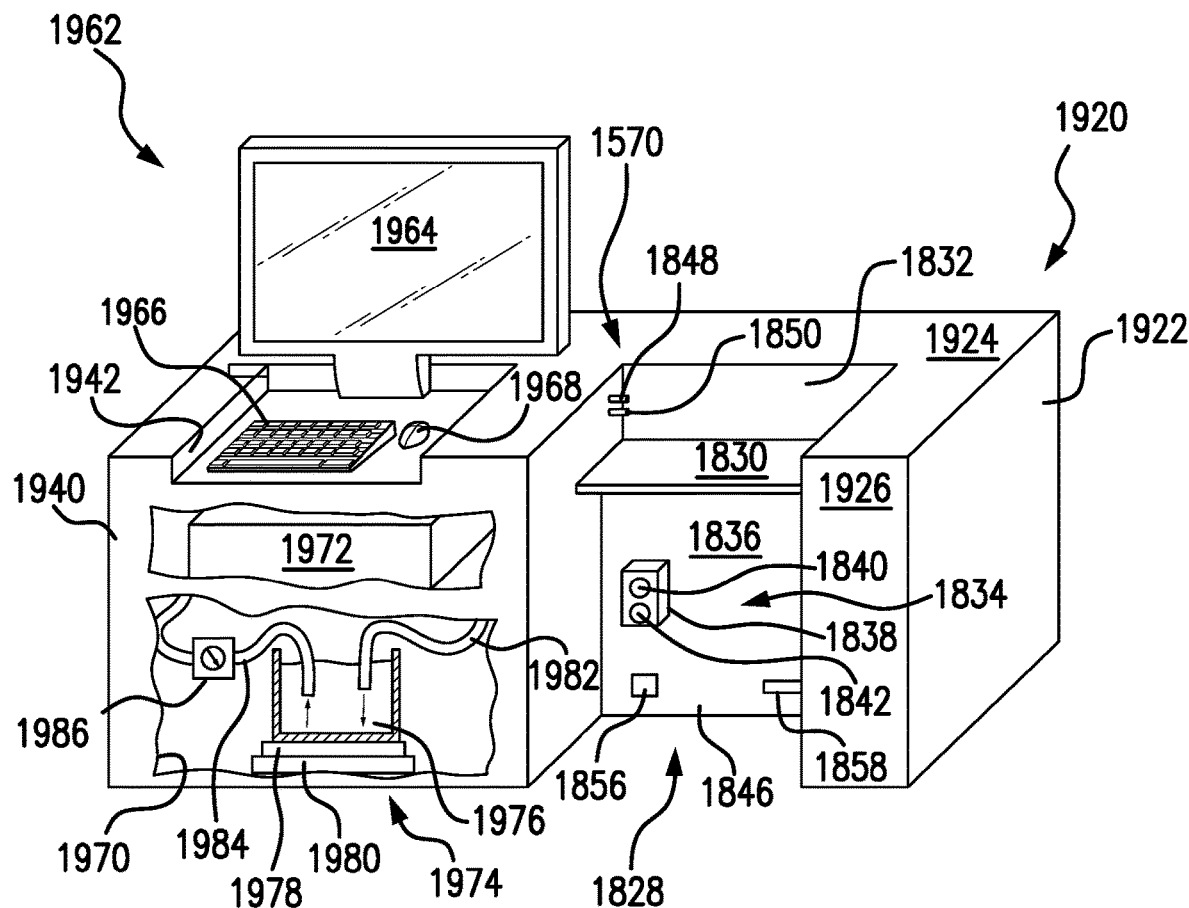
FIG. 18A is a right, top perspective view of another BM configured to dock a portable module.
Figure 18B:
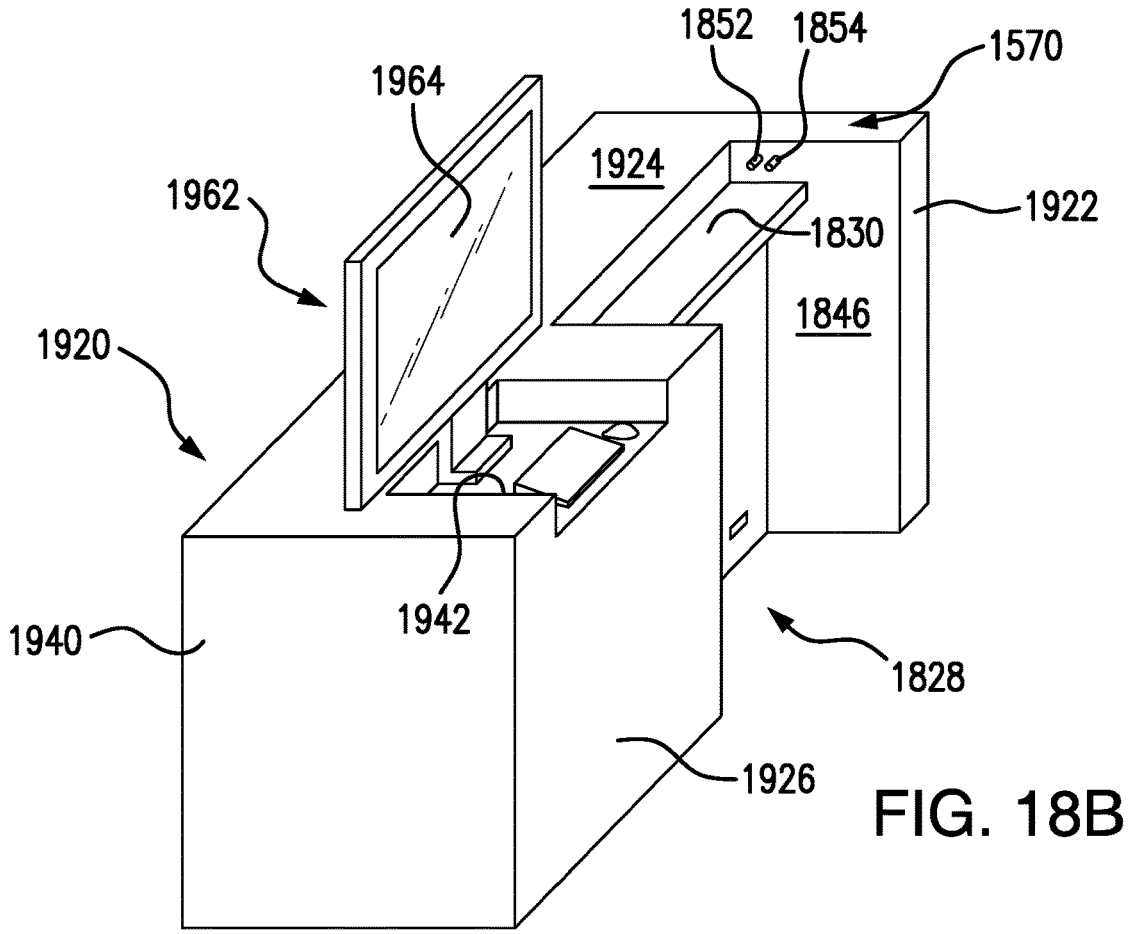
FIG. 18B is a left, top perspective view of the BM shown in FIG. 18A.

FIG. 18A is a right perspective view of a fourth BM 1920 configured to dock a portable module, and demonstrating a closure system. FIG. 18B is a left perspective view of the BM shown in FIG. 18A. The fourth BM 1920 can dock, for example, third portable module 1520 (FIG. 14) or fourth portable module 1620 (FIG. 15). The fourth BM 1920 can include a fourth BM housing 1922, a fourth BM top surface 1924, and a fourth BM front surface 1926. The fourth BM 1920 is similar to the third BM 1820 (FIGS. 17A and 17B) by having a universal BM dock 1828, but the fourth BM 1920 also features a fourth BM extended housing unit 1940. The fourth BM extended housing unit 1940 enables the inclusion of more components and systems. The fourth BM extended housing unit 1940 can include a fourth BM tray recess 1942, which can hold a fourth BM user interface 1962. The fourth BM user interface 1962 can include, for example, a monitor 1964, a keyboard 1966, and a mouse 1968, but can take the form of other types of user interfaces.

A fourth BM interior 1970 is partially visible in the cutaway view of FIG. 18A. The fourth BM interior 1970 can include, for example, a central control subsystem 1972. Central control subsystem 1972 can form part of a smart control system. The smart control system can be located at home, at a treatment center, or at multiple locations. The smart control system can be used, for example, to monitor a blood processing procedure and to allow for the procedure to be monitored on and/or from more than one machine. The central control subsystem 1972 can be accessed through a user interface such as fourth BM user interface 1962 and can interact with other devices (e.g., through a wireless communication with a mobile device functioning as an auxiliary user interface).

The fourth BM interior 1970 can also include, for example, a fourth BM dialysate circuit 1974. The fourth BM dialysate circuit 1974 can include, for example, a fourth BM dialysate reservoir 1976, a fourth BM dialysate weighing subsystem 1978, a fourth BM heater 1980, a fourth BM dialysate reservoir entry line 1982, a fourth BM dialysate reservoir exit line 1984, and a fourth BM dialysate pump 1986. The fourth BM dialysate circuit 1974 can include components and designs of other dialysate circuits described herein.

Figure 19:
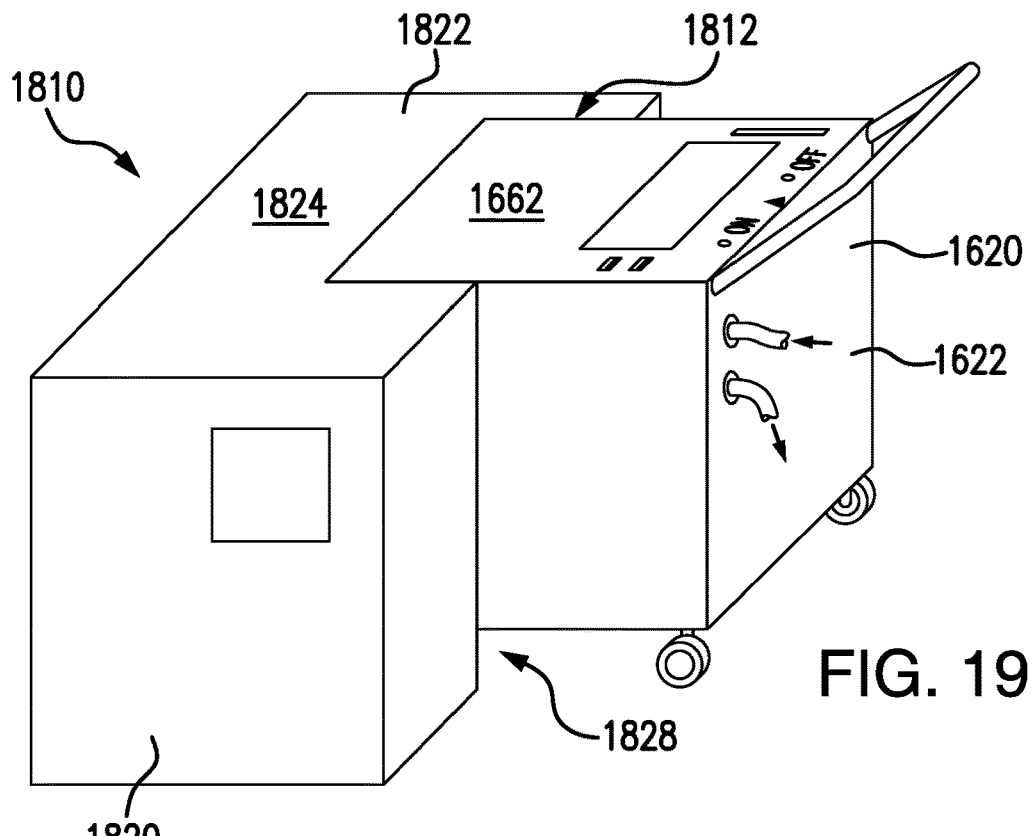
FIG. 19 is a modular system including the portable module shown in FIG. 15 docked with the BM shown in FIG. 17A.
Figure 20:
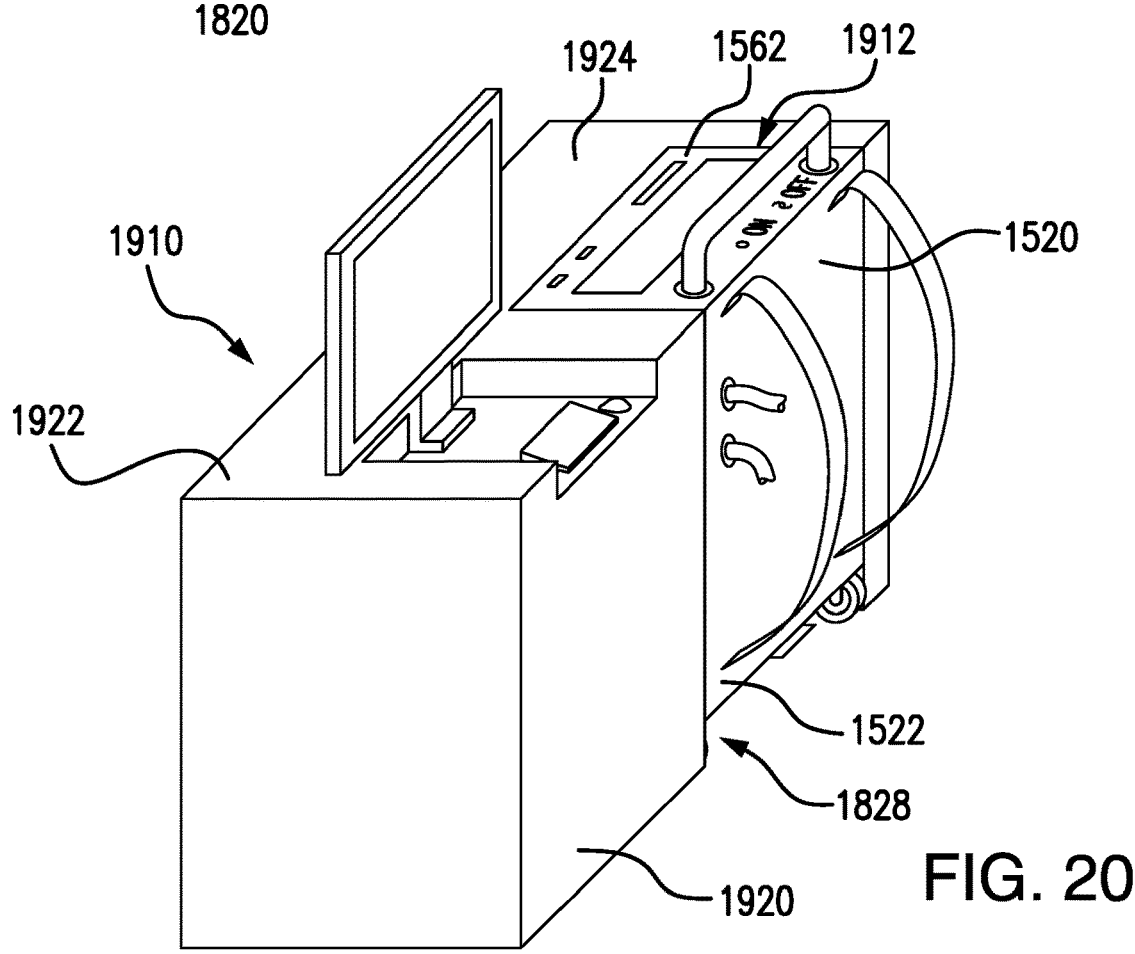
FIG. 20 is a left, top perspective view of a modular system including the portable module shown in FIG. 14 docked with the BM shown in FIG. 18A.

FIG. 19 is a seventh modular system 1810 including fourth portable module 1620 shown in FIG. 15 docked with third BM 1820 shown in FIGS. 17A and 17B. The two components connect at a first inter-modular boundary 1812. FIG. 20 is an eighth modular system 1910 including third portable module 1520 shown in FIG. 14 docked with fourth BM 1920 shown in FIGS. 18A and 18B. The two components connect at a second inter-modular boundary 1912. Given the universal nature of the docking system, the third portable module 1520 could alternatively dock with third BM 1820, and the fourth portable module 1620 could dock with fourth BM 1920.

FIGS. 21-27 schematically illustrate examples of layouts that can be used in, or modified for use in, systems of the present invention. The layouts can be used, for example, in: the modular systems 310, 510, 610, 710, 810, 1310, 1810, and 1910; the BM described herein (e.g., the first BM 320, the first base module 730, the second BM 1320, the third BM 1820, and the fourth BM 1920); and the portable modules described herein (e.g., the first portable module 520, the second portable module 620, the third portable module 1520, and the fourth portable module 1620). These layouts and others described herein enable a more flexible and more convenient dialysis treatment including re-initiating and continuing a dialysis therapy in different locations (e.g., at home or throughout a dialysis clinic).

A blood processing system in accordance with the present invention can include a user interface. The user interface can include such input elements as a monitor, a keyboard, a touchpad, a touchscreen, LEDs, treatment data display screens, and the like. The user interface serves to convey the treatment status visually and can provide the ability to adjust treatment settings. In an emergency situation, display of a potentially hazardous alarm state can be maintained, but the ability to tailor a treatment setting need not be included in all embodiments. For example, the ability to adjust a blood pump rate can facilitate patient disconnect in an emergency situation. The ability to adjust the ultrafiltration rate during an emergency disconnect, however, need not be included as the treatment is being terminated. LEDs, for example, can be used to signal or illustrate arterial, venous, and transmembrane pressure, for example, as provided on a Fresenius Medical Care 2008H machine, instead of having a monitor display or illustrate such pressures. One or more components, systems, machines, steps, and methods can be used from Fresenius Medical Care blood processing machines, for example, components, disposables, systems, and methods used with the 2008 series hemodialysis machines such as the 2008H and 2008K, available from Fresenius Medical Care, Waltham, Mass. The Operator's Manual for the Fresenius 2008H Hemodialysis Machine (1994-2001), the 2008K Hemodialysis Machine Operator's Manual (2000-2014), and the 2008 Series Hemodialysis Machine Spare Parts Manual (2008, 2015) are incorporated by reference herein in their entireties.

A blood processing system in accordance with the present invention can also include a dialysate (hydraulic) circuit. A dialysate circuit can include, for example, a dialysis generation unit, dialysate lines for supplying dialysate to a dialyzer, an ultrafiltration pump, a fluid heater, a fluid deaeration subsystem, a temperature sensor, a conductivity sensor, and a blood leak detector. A blood processing system in accordance with the present invention can further include an extracorporeal blood circuit, which can interconnect with the dialysate circuit at the dialyzer. The extracorporeal blood circuit can include, for example, bloodlines, arterial pressure sensors, venous pressure sensors, heparin and/or other anticoagulant infusion devices and supplies, a saline bag used for priming, a level detector, and a venous clamp. The interaction of the dialysate circuit and the blood circuit enables the blood processing apparatus to measure transmembrane pressure.

The user interface, the dialysate circuit, the extracorporeal blood circuit, and/or additional components can be modularized to provide a modularized machine capable of being disconnected during operation. The modularized systems enable greater flexibility to address various situations that may arise. For example, a patient can continue therapy, at least for a limited period, in a mobile no-dialysate flow state to transition to another blood processing apparatus in the event of a machine issue, a patient preference, a bathroom break, or a patient backlog at a treatment center. Therapy can be continued for a limited period in a mobile active dialysate flow state, for example, to enable a patient to use the restroom. Therapy can be continued for an extended period in a mobile active dialysate flow state, for example, to enable dialysis outside a treatment center or at home.

Figure 21:
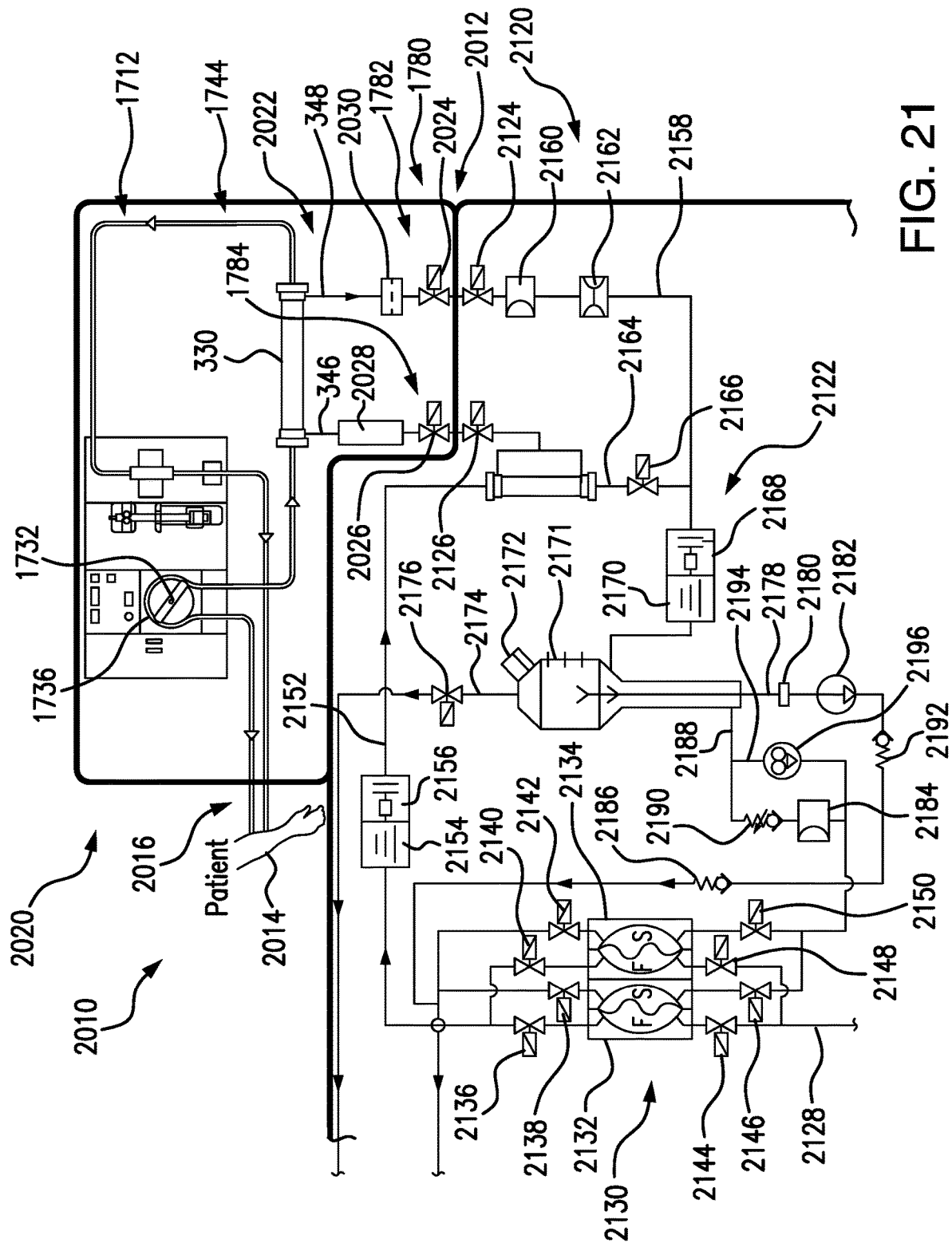
FIG. 21 is a schematic diagram of a modular system including a portable module docked with a BM.
Figure 22:
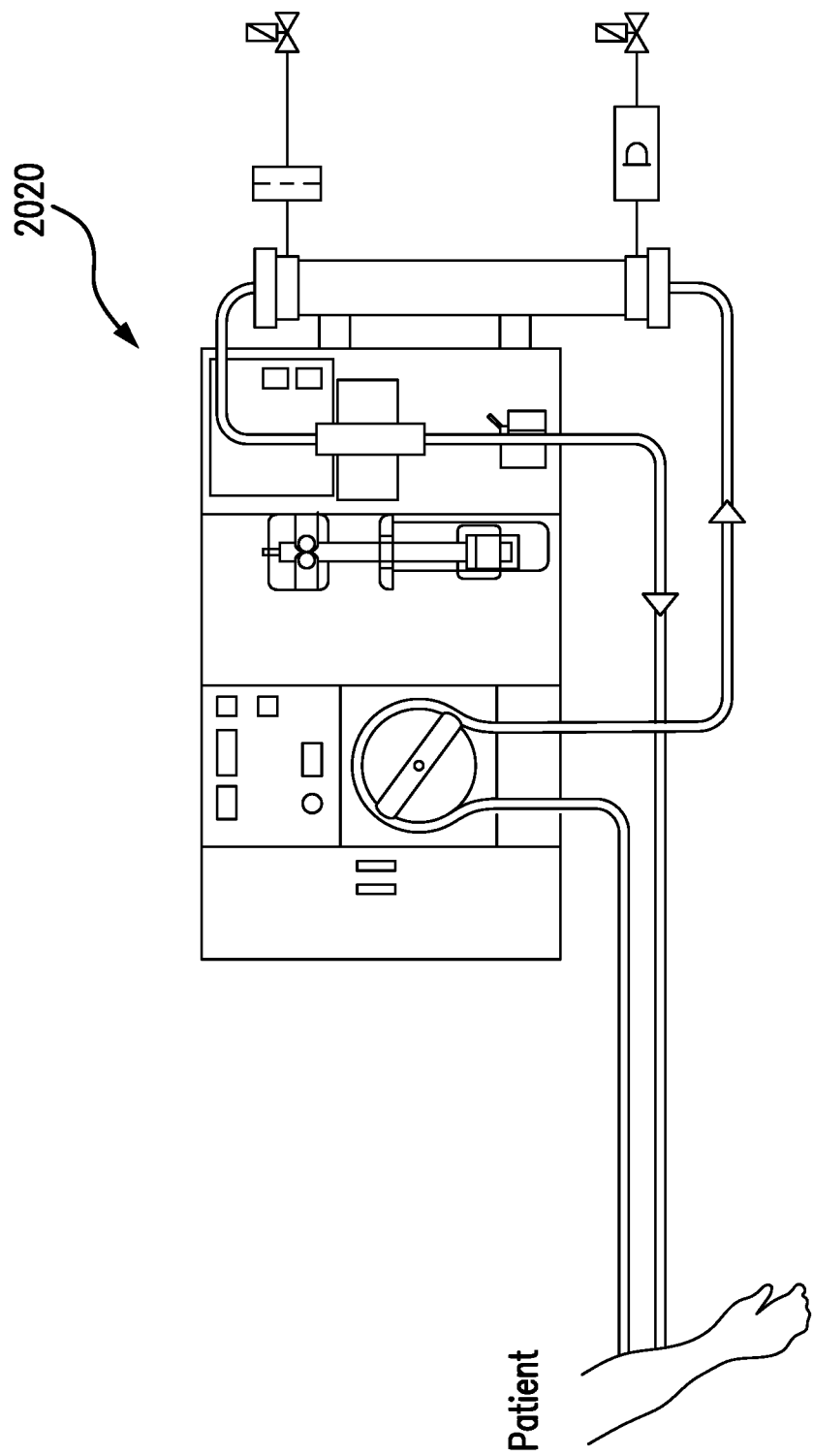
FIG. 22 is a front view of the portable module shown in FIG. 21.

FIG. 21 is a schematic diagram of a ninth modular system 2010 including a fifth portable module 2020 docked with a fifth BM 2120, demonstrating, for example, a closure system in accordance with the present invention. FIG. 22 is a front view of fifth portable module 2020 shown in FIG. 21. The fifth portable module 2020 connects to the fifth BM 2120 at a third inter-modular interface boundary 2012, and to a patient 2014 through a patient connection 2016, for example, a single needle or double needle connection. The fifth portable module 2020 is depicted connecting to the fifth BM 2120 through a dialysate circuit. The fifth portable module 2020 includes a fifth portable dialysate circuit 2022. The fifth portable dialysate circuit 2022 includes an inter-modular connector that includes, for example, a first inter-modular valve 2024 and a second inter-modular valve 2026. The fifth BM 2120 includes a fifth BM dialysate circuit 2122. The fifth BM dialysate circuit 2122 includes a complementary inter-modular connector that includes, for example, a first complementary inter-modular valve 2124 and a second inter-modular complementary valve 2126. These valves can collectively, for example, form a closure system of the present invention. The fifth portable dialysate circuit 2022 can also include, for example, a dialysate flow indicator 2028 between blood filter 330 and second inter-modular valve 2026, and a dialysate exit filter 2030 between blood filter 330 and the first inter-modular valve 2024. The fifth portable module 2020 can include a portable module blood circuit 1712, for example, as described herein with reference to FIGS. 16A and 16B and in which blood from patient 2014 can be moved through the blood line set 1744 by the portable module blood pump 1732.

Figure 23:
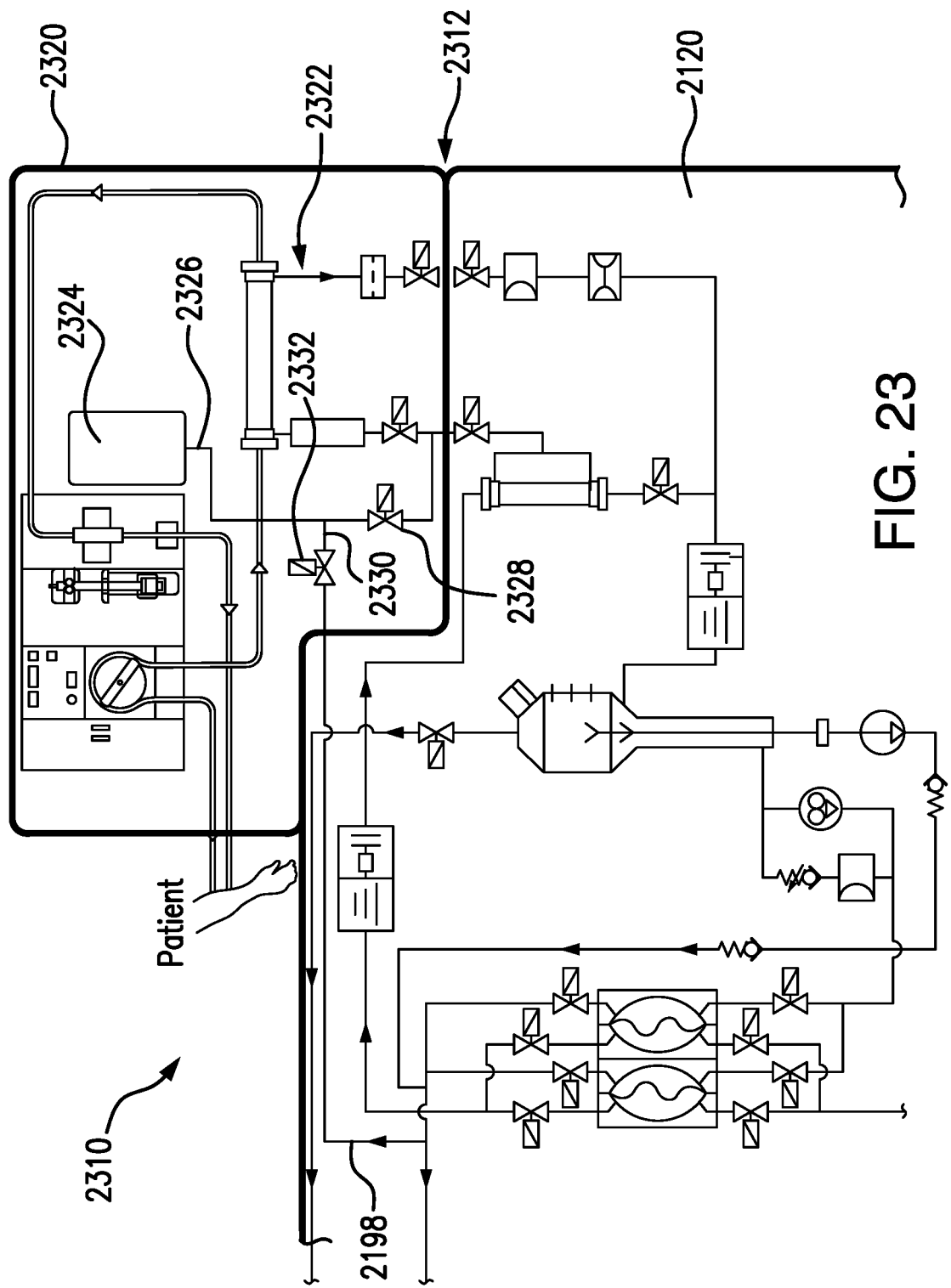
FIG. 23 is a schematic diagram of another modular system including another portable module docked with the BM shown in FIG. 21.
Figure 27:
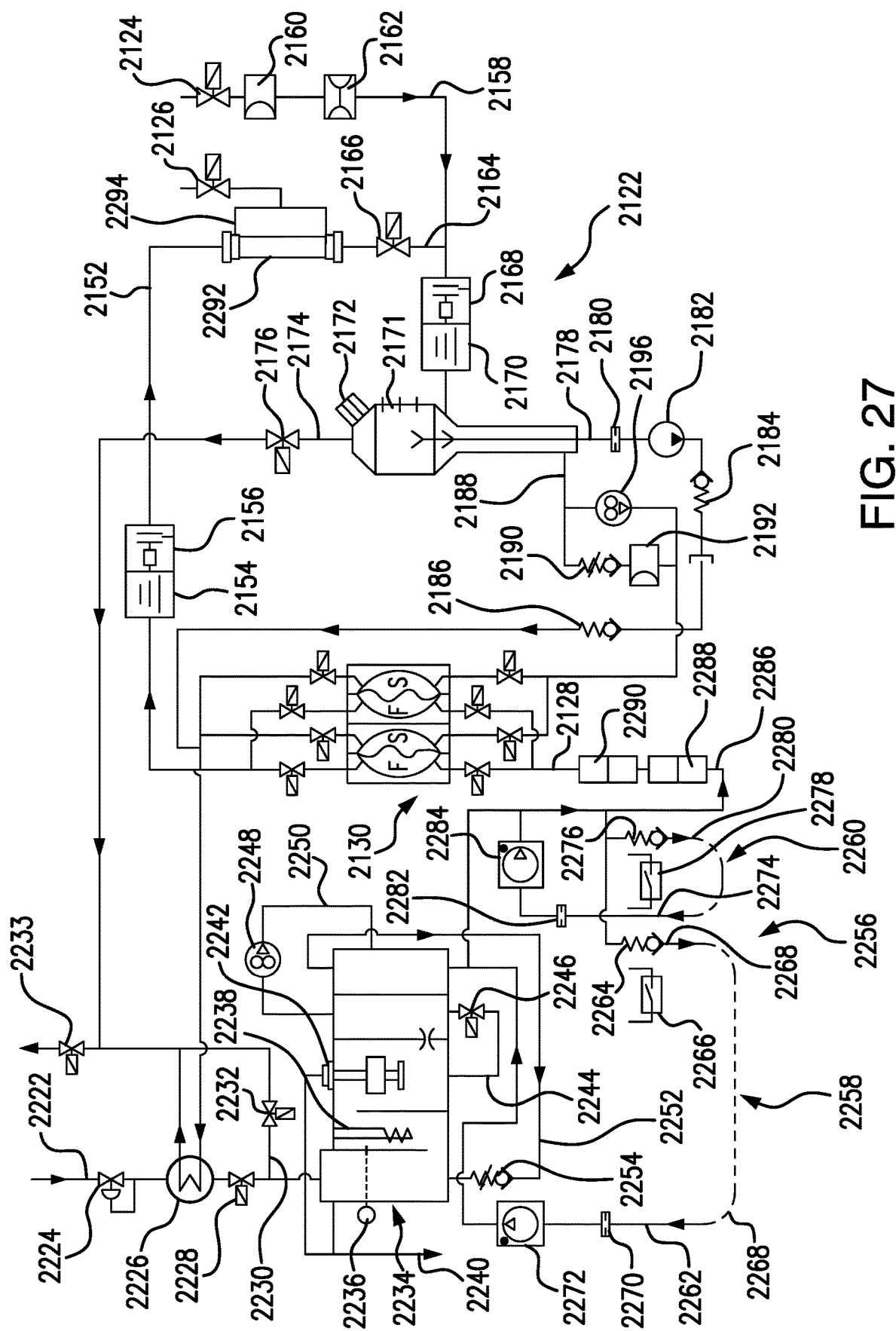
FIG. 27 is a schematic diagram of a dialysate circuit that can be used in the BMs shown in FIGS. 21 and 23.

The fifth BM dialysate circuit 2122 is shown, in part, in FIGS. 21 and 23, and in greater detail in FIG. 27. The fifth BM dialysate circuit 2122 is depicted, for example, as a single pass system similar to the dialysate flow system of the Fresenius 2008 series dialysis machines such as the Fresenius 2008H and the Fresenius 2008K machines. The fifth BM dialysate circuit 2122, however, can take alternative forms, whether single pass or regenerative in nature. In the fifth BM dialysate circuit 2122, dialysate can flow through a mixing chamber exit line 2128 to a balance chamber complex 2130. The balance chamber complex 2130 can include, for example, a first balance chamber 2132, a second balance chamber 2134, a first balance chamber valve 2136, a second balance chamber valve 2138, a third balance chamber valve 2140, a fourth balance chamber valve 2142, a fifth balance chamber valve 2144, a sixth balance chamber valve 2146, a seventh balance chamber valve 2148, and an eighth balance chamber valve 2150. Dialysate can flow from balance chamber complex 2130 through dialysate exit line 2152 that includes a dialysate conductivity cell 2154 and a dialysate temperature sensor 2156.

Spent dialysate leaving fifth portable dialysate circuit 2022 can enter the fifth BM dialysate circuit 2122 through a dialysate entry line 2158. Dialysate entry line 2158 can include a dialysate pressure transducer 2160 and a blood leak detector 2162. Dialysate can be diverted from dialysate exit line 2152 or dialysate entry line 2158 along with a bypass line 2164 using a bypass valve 2166. The dialysate entry line 2158 can also include a dialysate temperature sensor 2168 and a dialysate conductivity cell 2170. Dialysate cann flow: to an air separation chamber 2171 with an air sensor 2172, an air separation chamber vent line 2174, and an air separation chamber vent valve 2176; from an air separation chamber 2171 through a ultrafiltration line 2178 with a ultrafiltration filter 2180, a ultrafiltration pump 2182, and a first check valve 2192, and a second check valve 2186 to a balance chamber complex 213; to an air separation chamber 2171 through an air separation chamber dialysate exit line 2188 with a dialysate pump pressure release valve 2190 and a pressure transducer 2184; and from the air separation chamber dialysate exit line 2188 through a dialysate flow line 2194 with a dialysate flow pump 2196.

In ninth modular system 2010, an operator can initiate a disconnection event between the fifth portable module 2020 and the fifth BM 2120 by closing the first and second inter-modular valves 2024, 2026 and the first and second complementary inter-modular valves 2124, 2126 to stop the flow of dialysate to and from the fifth portable module 2020. This process can be performed through use, for example, of a BM user interface. Many of the dialysate circuit components in this embodiment can be located in the BM, for example, everything but a dialyzer. The fifth BM 2120 can include, for example, a user interface and machine hydraulics except for those portions of the dialysis circuit included in fifth portable module 2020. The fifth portable module 2020 can optionally be mounted on wheels and can include a battery to enable operation while disconnected from the machine hydraulics for a limited period. The portable module blood pump 1732 can continue to be controlled and used, while the dialysate flow is halted. Thus, flow in the fifth portable dialysate circuit 2022 can be temporarily halted while the blood circuit continues to circulate and/or recirculate blood in the circuit. Upon replacing fifth portable module 2020 on the fifth BM 2120, a reconnection event includes opening the closed valves thereby reinitiating fluid flow. The fifth portable module 2020 can instead be returned to a different BM if desired. For example, through the use of a wired or wireless connection, the progress of a treatment protocol programmed into the BM, on which blood processing is initiated, can be transferred to a different BM for the resumption of the protocol.

FIG. 23 is a schematic diagram of a tenth modular system 2310 including a sixth portable module 2320 docked with fifth BM 2120 shown in FIG. 21 in accordance with the present invention. The sixth portable module 2320 can include a sixth portable dialysate circuit 2322 that can connect to the fifth BM dialysate circuit 2122 (FIG. 21) in a manner analogous to that described for connecting with fifth portable dialysate circuit 2022 (FIG. 21), but at a fourth inter-module boundary 2312. The sixth portable dialysate circuit 2322 can include a portable dialysate reservoir 2324, which can hold fresh, regenerated, or spent dialysate. Dialysate can flow into or out of the portable dialysate reservoir 2324 through the portable reservoir line 2326, which can be controlled using a portable reservoir valve 2328. Dialysate can also be supplied to the sixth portable dialysate circuit 2322 through an alternative dialysate supply line 2198 and an alternative dialysate supply line 2330, flow through which can be controlled through an alternative dialysate supply valve 2332.

Dialysate can be introduced into the portable dialysate reservoir 2324. A filling program can be used to supply dialysate through the portable reservoir valve 2328 at a slow enough rate to prevent misbalancing to ensure therapy can continue without an adverse impact on clearance until the desired fluid volume is obtained. To fill the container faster, spent dialysate can be sent to the portable dialysate reservoir 2324 through the alternative dialysate supply valve 2332. That configuration can enable faster delivery to the reservoir with minimal or no impact on balance chamber complex 2130 (FIG. 21).

Figure 24:
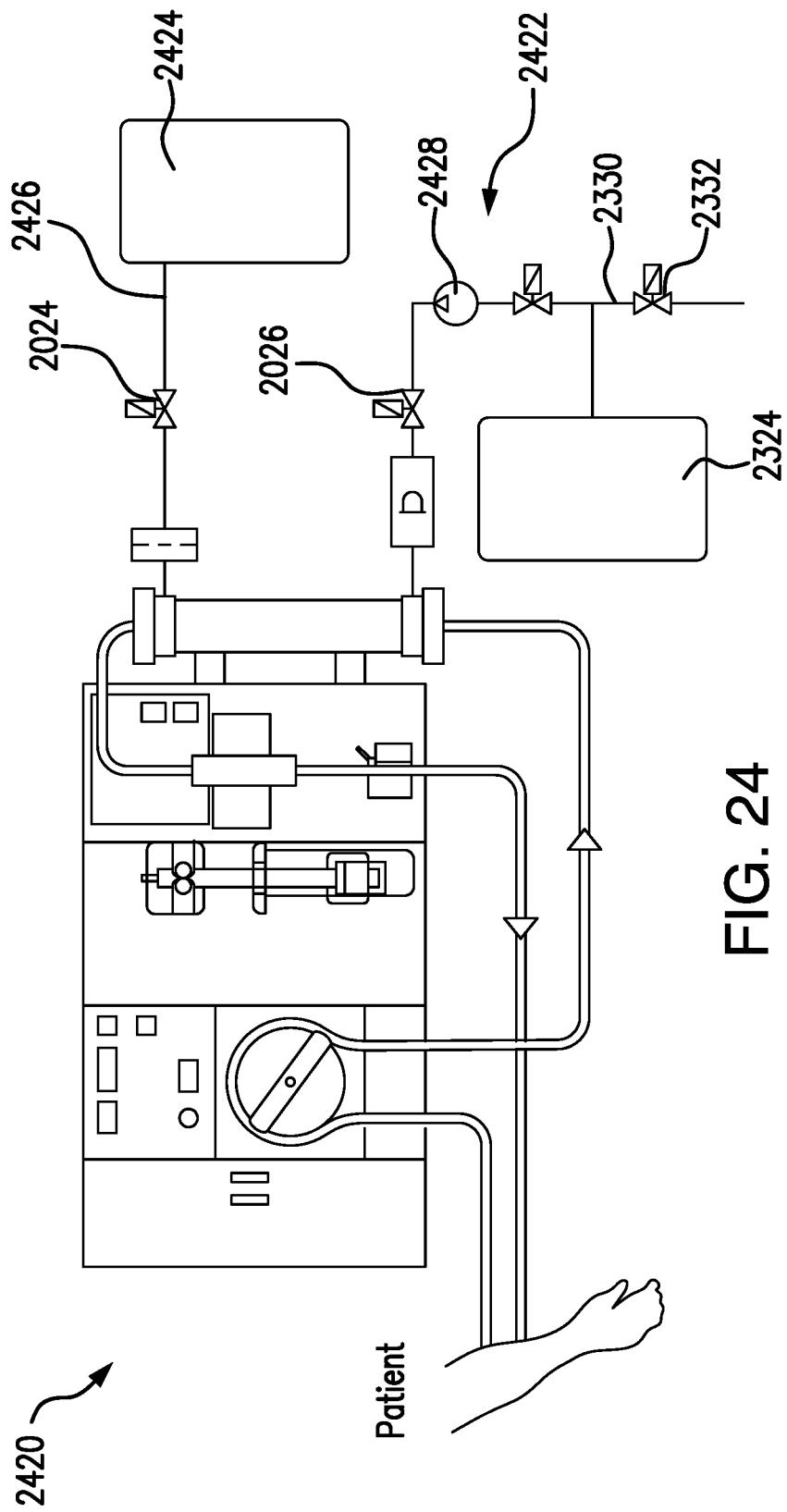
FIG. 24 is a combined front view and schematic diagram of yet another portable module.

FIG. 24 is a schematic diagram of a seventh portable module 2420 in accordance with the present invention. The seventh portable module 2420 can dock with the fifth BM 2120 (FIGS. 21 and 23) in a manner analogous to that described for connecting fifth portable dialysate circuit 2022. In FIG. 24, the seventh portable module 2420 is depicted in an undocked configuration. The seventh portable module 2420 can include a seventh portable dialysate circuit 2422. The seventh portable dialysate circuit 2422 can include components in common with other dialysate circuits described herein, for example, those of the sixth portable dialysate circuit 2322 (FIG. 23), as well as additional components. For example, the seventh portable dialysate circuit 2422 can include a portable dialysate reservoir 2424, which can be configured to accept spent dialysate through first inter-modular valve 2024 and a portable module spent dialysate the line 2426. Dialysate can be supplied to the seventh portable dialysate circuit 2422 using a portable module dialysate pump 2428 from the portable dialysate reservoir 2324 or from the fifth BM dialysate circuit 2122 (FIG. 21) through the alternative dialysate supply line 2330 and the alternative dialysate supply valve 2332.

Figure 25:
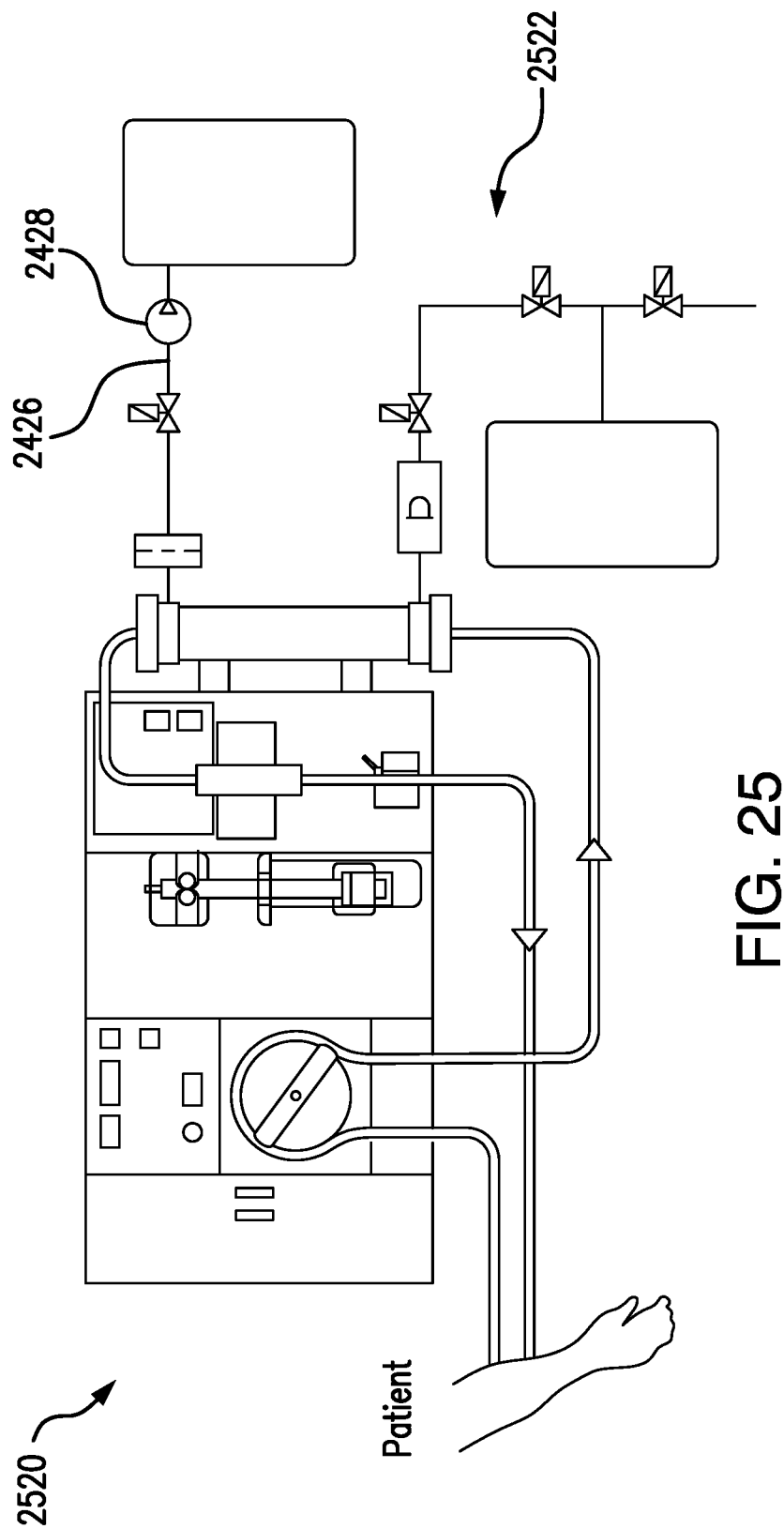
FIG. 25 is a combined front view and schematic diagram of still another portable.

FIG. 25 is a schematic diagram of an eighth portable module 2520 in accordance with the present invention. The eighth portable module 2520 can dock with the fifth BM 2120 (FIGS. 21 and 23) in a manner analogous to that described for connecting the fifth portable dialysate circuit 2022. In FIG. 25, the eighth portable module 2520 is depicted in an undocked configuration. The eighth portable module 2520 can include an eighth portable dialysate circuit 2522. The eighth portable dialysate circuit 2522 is configured similar to the seventh portable dialysate circuit 2422 (FIG. 24), but a portable module dialysate pump 2428 is instead located on portable module spent dialysate the line 2426. In this manner, the portable module dialysate pump 2428 can act as an ultrafiltration pump, whether or not docked to a BM.

Figure 26:
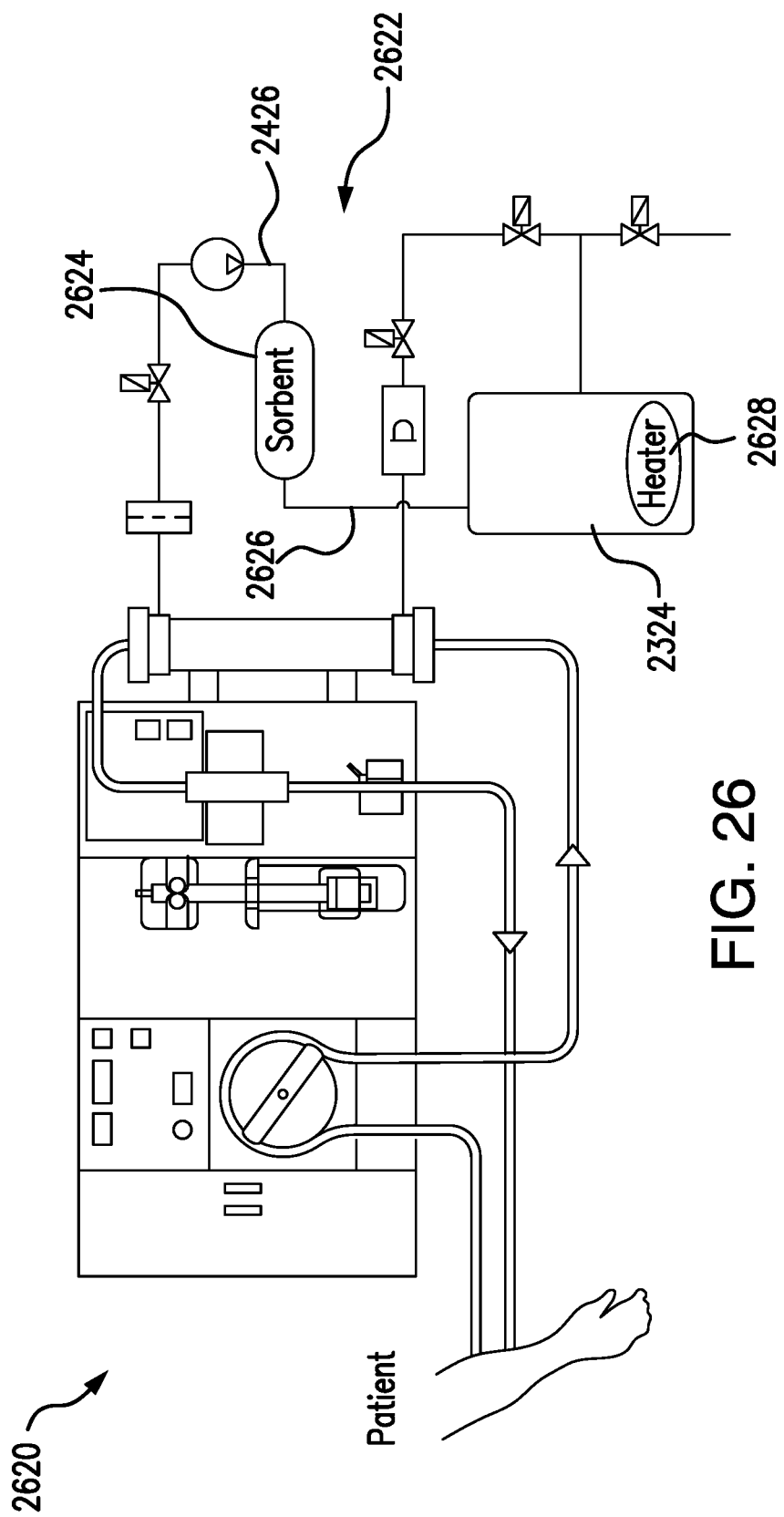
FIG. 26 is a combined front view and schematic diagram of yet another portable module.

FIG. 26 is a schematic diagram of a ninth portable module 2620 in accordance with the present invention that eliminates or minimizes uremic toxin accumulation. The ninth portable module 2620 can dock with the fifth BM 2120 (FIGS. 21 and 23) in a manner analogous to that described for connecting fifth portable dialysate circuit 2022. In FIG. 26, the ninth portable module 2620 is depicted in an undocked configuration.

The ninth portable module 2620 can include a ninth portable dialysate circuit 2622. The ninth portable dialysate circuit 2622 can include components in common with other dialysate circuits described herein, for example, those of the sixth portable dialysate circuit 2322 (FIG. 23), as well as additional components. In FIG. 26, the ninth portable dialysate circuit 2622 is depicted as a regenerative, dialysate circuit loop including a portable sorbent cartridge 2624 that can regenerate spent dialysate that can be returned for use through the portable sorbent exit line 2626 and back into the portable dialysate reservoir 2324. Dialysate in the reservoir can be heated by a portable dialysate heater 2628.

The ninth portable dialysate circuit 2622 and the other dialysate circuits described herein can be expanded to include some or all of the components of the fifth BM dialysate circuit 2122 (FIG. 21).

FIG. 27 is a schematic diagram of the fifth BM dialysate circuit 2122 shown in FIGS. 21 and 23, in accordance with the present disclosure. Dialysate can flow in the circuit as described herein with respect to FIG. 21 as well as in a manner described as follows and/or consistent with the Fresenius dialysis system 2008H or 2008K. The fifth BM dialysate circuit 2122 can be configured to prepare dialysate from water and concentrate. For example, water can flow into the fifth BM dialysate circuit 2122 through a water entry line 2222, a water inlet pressure regulator 2224, a BM heat exchanger 2226, and a water inlet valve 2228. Fluid can optionally be redirected through a recirculation line 2230 by controlling a recirculation valve 2232. Fluid can ultimately leave the fifth BM dialysate circuit 2122 through a system drain valve 2233. Water can flow into a deaeration chamber complex 2234. The deaeration chamber complex 2234 can include, for example, a deaeration chamber temperature control thermistor 2236, a deaeration chamber heater 2238, a deaeration chamber vent line 2240, a deaeration float switch 2242, a deaeration chamber bypass line 2244, a deaeration chamber bypass valve 2246, a deaeration chamber pump 2248, a deaeration chamber pump line 2250, and a deaeration chamber loading line 2252 that includes a loading pressure valve 2254.

The concentrate can be supplied from a dialysate concentrate system 2256 that can include an acetate concentrate subsystem 2258 and a bicarbonate subsystem 2260. The acetate concentrate subsystem 2258 can include an acetate (concentrate) line 2262, an acetate check valve 2264, an acetate feed switch wand 2266, an acetate port 2268, an acetate filter 2270, and an acetate pump 2272. The bicarbonate subsystem 2260 can include a bicarbonate line 2274, a bicarbonate check valve 2276, a bicarbonate feed switch wand 2278, a bicarbonate port 2280, a bicarbonate filter 2282, and a bicarbonate pump 2284. After the concentrate has been added, the resulting fluid can flow through a mixing chamber entry line 2286 to one or more mixing chambers (e.g., the mixing chambers 2288, 2290). The dialysate exit line 2152 can optionally include a dialysate filter 2292 and a dialysate filter exit line 2294 to further process the dialysate before use. In some examples, the dialysate filter 2292 is a dialyzer. In some examples, the dialysate filter 2229 is a fluid filter (e.g., a DIASAFE® plus filter available from Fresenius Medical Care).

The present invention includes the following aspects/embodiments/features in any order and/or in any combination:

1. A portable blood circuit adapter comprising:

an extracorporeal blood circuit tubing set comprising a to-patient venous line and a from-patient arterial line, each of the venous line and arterial line having an adapter end and a patient end configured to connect with a vascular access or vascular access implant;

an adapter housing comprising a module connector configured to engage a complementary inter-module connector of a blood treatment apparatus that comprises a blood pump configured to pump blood extracorporeally through the extracorporeal blood circuit tubing set, the adapter housing comprising tube connectors for fixing the adapter ends of the venous line and the arterial line to the adapter housing, the tube connectors being in fluid communication with the module connector and providing interruptible fluid flow paths between the venous line and the module connector and between the arterial line and the module connector; and a closure system mounted in or on the adapter housing and configured to (1) interrupt fluid communication between the venous line and the module connector and between the arterial line and the module connector, when the portable blood circuit adapter is disconnected from a blood treatment apparatus, and (2) provide fluid communication between the venous line and the module connector and between the arterial line and the module connector when the portable blood circuit adapter is connected to a complementary inter-module connector of a blood treatment apparatus.

2. The portable blood circuit adapter of any preceding or following embodiment/feature/aspect, further comprising an anticoagulant dispenser mounted in or on the adapter housing and in fluid communication with the extracorporeal blood circuit tubing set.

3. The portable blood circuit adapter of any preceding or following embodiment/feature/aspect, wherein the module connector is configured to engage a complementary inter-module connector of a blood treatment apparatus by a snap-fit connection, a hook and loop combination, a latch, a lock, a press-fit connection, a friction-fit connection, a magnetic coupling connection, or any combination thereof.

4. The portable blood circuit adapter of any preceding or following embodiment/feature/aspect, further comprising a user interface on, or connected to, the adapter housing.

5. The portable blood circuit adapter of any preceding or following embodiment/feature/aspect, wherein the arterial line and the venous line together form a single needle access line.

6. A modular system comprising:

the portable blood circuit adapter of any preceding or following embodiment/feature/aspect; and a portable blood processing module comprising an inter-module connector that is complementary to the module connector of the adapter housing, a station blood circuit including a to-patient line and a from-patient line, and a first blood pump, wherein each of the to-patient line and the from-patient line of the station blood circuit have a connector end in fluid communication with the inter-module connector, and the first blood pump is configured to circulate blood through the station blood circuit, through the extracorporeal blood circuit tubing set, and to and from a patient.

7. The modular system of any preceding or following embodiment/feature/aspect, wherein the portable blood processing module further comprises a dialysate circuit and a blood filter, wherein the blood filter is in fluid communication with the station blood circuit and the dialysate circuit.

8. The modular system of any preceding or following embodiment/feature/aspect, wherein the blood filter comprises a dialyzer.

9. The modular system of any preceding or following embodiment/feature/aspect, wherein the portable blood processing module further comprises a dialysate pump in operable communication with the dialysate circuit, a sorbent cartridge in fluid communication with the dialysate circuit, and a heater in operable communication with the dialysate circuit.

10. The modular system of any preceding or following embodiment/feature/aspect, wherein the portable blood processing module further comprises a battery-powered power source.

11. The modular system of any preceding or following embodiment/feature/aspect, further comprising an engagement verification subsystem configured to indicate that the portable blood circuit adapter is securely engaged with the portable blood processing module, wherein the engagement verification subsystem is configured to generate a first detectable signal when the portable blood circuit adapter is securely engaged with the portable blood processing module, and a second detectable signal when the portable blood circuit adapter is disengaged from the portable blood processing module, and each of the first detectable signal and the second detectable signal independently comprises a visual signal, an audible signal, a haptic signal, or any combination thereof.

12. A modular system comprising:

the portable blood circuit adapter of any preceding or following embodiment/feature/aspect; and a non-portable, first base module comprising an inter-module connector that is complementary to the module connector of the adapter housing, a base station blood circuit including a to-patient line and a from-patient line, a second blood pump, a dialysate pump, and a dialysate circuit, the second blood pump being configured to circulate blood through the base station blood circuit, through the extracorporeal blood circuit tubing set, and to and from a patient, wherein the dialysate circuit comprises a blood filter, and the blood filter is in fluid communication with the base station blood circuit and the dialysate circuit.

13. The modular system of any preceding or following embodiment/feature/aspect, wherein the blood filter comprises a dialyzer.

14. The modular system of any preceding or following embodiment/feature/aspect, wherein the dialysate circuit further comprises a sorbent cartridge, a heater in operable communication with the dialysate circuit, a temperature sensor, a conductivity sensor, and a weighing subsystem.

15. The modular system of any preceding or following embodiment/feature/aspect, further comprising an engagement verification subsystem configured to indicate that the portable blood circuit adapter is securely engaged with the first base module, wherein the engagement verification subsystem is configured to generate a first detectable signal when the portable blood circuit adapter is securely engaged with the first base module and a second detectable signal when the portable blood circuit adapter is disengaged from the first base module, and each of the first detectable signal and the second detectable signal independently comprises a visual signal, an audible signal, a haptic signal, or any combination thereof.

16. A method comprising:

providing the modular system of any preceding or following embodiment/feature/aspect;

connecting each of the patient ends of the venous line and the arterial line to vascular access points of a patient;

engaging the portable blood circuit adapter with the first base module; and performing at least one blood treatment on the patient, wherein the at least one blood treatment comprises blood circulation, hemodialysis, hemofiltration, hemodiafiltration, or any combination thereof.

17. The method of any preceding or following embodiment/feature/aspect, further comprising:

disengaging the portable blood circuit adapter from the first base module; and without disconnecting the extracorporeal blood circuit tubing set from the patient, engaging the portable blood circuit adapter with a portable blood processing module, the portable blood processing module comprising an inter-module connector that is complementary to the module connector of the adapter housing, a station blood circuit including a to-patient line and a from-patient line, and a first blood pump, wherein each of the to-patient line and the from-patient line of the station blood circuit have a connector end in fluid communication with the inter-module connector, and the blood pump is configured to circulate blood through the station blood circuit, through the extracorporeal blood circuit tubing set, and to and from the patient.

18. The method of any preceding or following embodiment/feature/aspect, further comprising:

disengaging the portable blood circuit adapter from the portable blood processing module; and reengaging the portable blood circuit adapter with the first base module without disconnecting the extracorporeal blood circuit tubing set from the patient.

19. The method of any preceding or following embodiment/feature/aspect, further comprising resuming the at least one blood treatment.

20. The method of any preceding or following embodiment/feature/aspect, further comprising performing a blood treatment on the patient, which differs from the at least one blood treatment.

21. The method of any preceding or following embodiment/feature/aspect, further comprising:

disengaging the portable blood circuit adapter from the first base module;

engaging the portable blood circuit adapter with a second base module; and performing at least one blood treatment on the patient, using the second base module.

22. A method comprising:

providing the modular system of any preceding or following embodiment/feature/aspect;

connecting each of the patient ends of the venous line and the arterial line to vascular access points of a patient;

engaging the portable blood circuit adapter with the portable blood processing module; and performing at least one blood treatment on the patient, wherein the at least one blood treatment comprises blood circulation, hemodialysis, hemofiltration, hemodiafiltration, or any combination thereof.

23. The method of any preceding or following embodiment/feature/aspect, further comprising disengaging the portable blood circuit adapter from the portable blood processing module and then withdrawing the patient ends from the vascular access points.

24. A modular system comprising:

the portable blood circuit adapter of any preceding or following embodiment/feature/aspect;

a base station comprising a dialysate circuit and a first dialysate pump in operative communication with the dialysate circuit;

a first remote station located at least ten feet away from the base station and comprising a first blood pump, an inter-module connector that is complementary to the module connector of the adapter housing, and a local blood circuit in fluid communication with the inter-module connector, the first blood pump being in operative communication with the local blood circuit, the dialysate circuit extending from the base station to the first remote station; and a first blood filter in fluid communication with both the local blood circuit and the dialysate circuit.

25. The modular system of any preceding or following embodiment/feature/aspect, wherein the first remote station further comprises a remote user interface and the base station further comprises a base station user interface.

26. The modular system of any preceding or following embodiment/feature/aspect, wherein the first blood filter comprises a dialyzer.

27. The modular system of any preceding or following embodiment/feature/aspect, wherein the first remote station comprises a fitting and the first blood filter is secured in the fitting.

28. The modular system of any preceding or following embodiment/feature/aspect, wherein the base station comprises a sorbent cartridge fitting, a heater in operative thermal communication with the dialysate circuit, and a reservoir, the dialysate circuit comprises a sorbent cartridge, and the sorbent cartridge is configured to be secured in the sorbent cartridge fitting.

29. The modular system of any preceding or following embodiment/feature/aspect, further comprising a second dialysate pump in operative communication with the dialysate circuit.

30. The modular system of any preceding or following embodiment/feature/aspect, wherein the base station further comprises a temperature sensor configured for sensing the temperature of dialysate in the dialysate circuit, a conductivity sensor configured for sensing the conductivity of dialysate in the dialysate circuit, and a weighing subsystem configured for weighting dialysate.

31. The modular system of any preceding or following embodiment/feature/aspect, wherein the base station and the first remote station are located in different rooms, on different levels, or both, of a building.

32. The modular system of any preceding or following embodiment/feature/aspect, further comprising a second remote station located remotely from the base station and comprising a second blood pump, a second inter-module connector that is complementary to the module connector of the adapter housing, and a second local blood circuit in fluid communication with the second inter-module connector, wherein the second blood pump is in operative communication with the second local blood circuit and the dialysate circuit extends from the base station to the second remote station.

33. The modular system of any preceding or following embodiment/feature/aspect, further comprising an engagement verification subsystem configured to indicate whether the portable blood circuit adapter is securely engaged with either the first remote station or the second remote station, the engagement verification subsystem being configured to generate a first detectable signal when the portable blood circuit adapter is securely engaged with the first remote station or the second remote station, and configured to generate a second detectable signal when the portable blood circuit adapter is disengaged from both the first remote station and the second remote station.

34. The modular system of any preceding or following embodiment/feature/aspect, further comprising a remote station lockout subsystem configured to lock-out use of the second remote station when the portable blood circuit adapter is engaged with the first remote station, and to lock-out use of the first remote station when the portable blood circuit adapter is engaged with the second remote station.

35. A method comprising:
providing the modular system of any preceding or following embodiment/feature/aspect;
connecting each of the patient ends of the venous line and the arterial line to vascular points of a patient;
engaging the portable blood circuit adapter with the first remote station; and
performing at least one blood treatment on the patient.

36. The method of any preceding or following embodiment/feature/aspect, wherein the at least one blood treatment comprises blood circulation, hemodialysis, hemofiltration, hemodiafiltration, or any combination thereof.

37. A method comprising:
providing the modular system of any preceding or following embodiment/feature/aspect;
connecting each of the patient ends of the venous line and the arterial line to vascular points of a patient;
engaging the portable blood circuit adapter with the first remote station;
performing at least one blood treatment on the patient;
disengaging the portable blood circuit adapter from the first remote station; and
without disconnecting the extracorporeal blood circuit tubing set from the patient, engaging the portable blood circuit adapter with the second remote station.

38. A modular system comprising:
a first base module comprising a dock and configured to dock a portable extracorporeal blood circuit module, the first base module comprising a base module housing, a primary dialysate circuit comprising a primary dialysate pump, a primary dialysate line, and a first inter-module connector; and
a first portable module configured to dock the first base module in a docked configuration and configured to operate independently of the first base module in an undocked configuration, the first portable module comprising a first portable module housing, a blood pump mounted in or on the first portable module housing, a first extracorporeal blood circuit tubing set, and a second inter-module connector complementary to the first inter-module connector and configured to connect to the first inter-module connector in the docked configuration, wherein the blood pump is configured to releasably engage the extracorporeal blood circuit tubing set.

39. The modular system of any preceding or following embodiment/feature/aspect, wherein the primary dialysate circuit further comprises a blood filter in fluid communication with the primary dialysate line, the first inter-module connector is in fluid communication with the blood filter, and the second inter-module connector is in fluid communication with the extracorporeal blood circuit tubing set.

40. The modular system of any preceding or following embodiment/feature/aspect, wherein the blood filter comprises a dialyzer.

41. The modular system of any preceding or following embodiment/feature/aspect, wherein the primary dialysate circuit further comprises a primary heater and a sorbent cartridge.

42. The modular system of any preceding or following embodiment/feature/aspect, wherein the primary dialysate circuit further comprises a temperature sensor configured for sensing a temperature of dialysate in the dialysate circuit, a conductivity sensor configured for sensing a conductivity of dialysate in the dialysate circuit, a weighing subsystem configured for weighing dialysate in the dialysate circuit, a secondary heater, or any combination thereof.

43. The modular system of any preceding or following embodiment/feature/aspect, wherein the extracorporeal blood circuit tubing set comprises a blood filter, the blood filter comprises a membrane that separates the blood filter into a blood side of the blood filter and a dialysate side of the blood filter, the dialysate side of the blood filter is in fluid communication with the second inter-module connector, and the primary dialysate line is in fluid communication with the first inter-module connector.

44. The modular system of any preceding or following embodiment/feature/aspect, wherein the extracorporeal blood circuit tubing set comprises an arterial line, the blood filter, and a venous line, and both the arterial line and the venous line are in fluid communication with the blood side of the blood filter.

45. The modular system of any preceding or following embodiment/feature/aspect, wherein the first base module further comprises a primary user interface, and the first portable module further comprises a secondary user interface.

46. The modular system of any preceding or following embodiment/feature/aspect, further comprising a central control subsystem comprising a central control user interface and being configured to control the first portable module.

47. The modular system of any preceding or following embodiment/feature/aspect, further comprising a mobile communications device comprising a mobile communications device user interface and being configured to control the first portable module.

48. The modular system of any preceding or following embodiment/feature/aspect, wherein the first base module housing comprises a receptacle at least partially defining the first inter-module connector and being configured to receive and secure at least a portion of the first portable module housing including the second inter-module connector.

49. The modular system of any preceding or following embodiment/feature/aspect, wherein the first portable module housing is configured to engage the base module housing at an interface between the first and second inter-module connectors by a hook and loop combination connector, a latch, a lock, a snap-fit connector, a frictional engagement, a magnetic coupling connector, or any combination thereof.

50. The modular system of any preceding or following embodiment/feature/aspect, wherein the first portable module comprises a cart, a set of wheels, a wheeled bag, a belt, a waist pack, a neck strap, a shoulder strap, a shoulder harness, a backpack, a chest pack, or any combination thereof.

51. The modular system of any preceding or following embodiment/feature/aspect, wherein the first inter-module connector comprises one or more valves that are configured to be in an open state in the docked configuration and to be in a closed state in the undocked configuration.

52. The modular system of any preceding or following embodiment/feature/aspect, wherein the extracorporeal blood circuit tubing set comprises a blood filter, the blood filter comprises a membrane that separates the blood filter into a blood side of the blood filter and a dialysate side of the blood filter, the first portable module further comprises a secondary dialysate circuit comprising a secondary dialysate pump, and the secondary dialysate circuit is in fluid communication with the dialysate side of the blood filter.

53. The modular system of any preceding or following embodiment/feature/aspect, wherein the second inter-module connector is in fluid communication with a fresh dialysate reservoir and a spent dialysate reservoir, and the secondary dialysate pump is located along the secondary dialysate circuit between the dialyzer and the fresh dialysate jug.

54. The modular system of any preceding or following embodiment/feature/aspect, wherein the first inter-module connector further comprises a first electrical connector, the second inter-module connector further comprises a second electrical connector that is complementary to the first electrical connector, and the first portable module further comprises a battery-operated auxiliary power source.

55. The modular system of any preceding or following embodiment/feature/aspect, further comprising an engagement verification subsystem configured to generate a detectable signal when the first portable module is securely engaged with the first base module, wherein the detectable signal comprises a visual signal, an audible signal, a haptic signal, or any combination thereof.

56. The modular system of any preceding or following embodiment/feature/aspect, wherein the engagement verification subsystem is configured to generate a second detectable signal when the first portable module is disengaged from the first base module, and the second detectable signal comprises a visual signal, an audible signal, a haptic signal, or any combination thereof.

57. The modular system of any preceding or following embodiment/feature/aspect, further comprising a second portable module configured to dock with the first base module in a docked configuration, and configured to operate independently of the first base module in an undocked configuration, the second portable module comprising a second portable module housing, a second blood pump mounted in or on the second portable module housing, a second extracorporeal blood circuit tubing set, and a third inter-module connector complementary to the first inter-module connector and configured to connect to the first inter-module connector, wherein the second blood pump is configured to releasably engage the second extracorporeal blood circuit tubing set.

58. The modular system of any preceding or following embodiment/feature/aspect, wherein the third portable module differs from the second portable module and is configured to perform a different blood treatment on a patient than is the second portable module.

59. The modular system of any preceding or following embodiment/feature/aspect, further comprising a second base module comprising a dock configured to dock the first portable module, wherein the first and second base modules are in different respective rooms of a building, are on different respective levels of a building, or are in different respective buildings.

60. The modular system of any preceding or following embodiment/feature/aspect, wherein the second base module differs from the first base module and the first and second base modules are configured to perform different blood treatments with respect to one another.

61. A method of comprising:
providing the modular system of any preceding or following embodiment/feature/aspect;
connecting a patient to the first extracorporeal blood circuit tubing set;
engaging the first portable module with the first base module; and
performing at least one blood treatment on the patient, comprising hemodialysis, hemofiltration, hemodiafiltration, or any combination thereof.

62. The method of any preceding or following embodiment/feature/aspect, further comprising:
disengaging the first portable module from the first base module; and
engaging a second portable module with the first base module.

63. The method of any preceding or following embodiment/feature/aspect, further comprising:
disengaging the first portable module from the first base module;
moving the patient and the first portable module while the patient is connected to the first extracorporeal blood circuit tubing set, to a location that is remote from the first base module; and
engaging the first portable module with a second base module.

64. The method of any preceding or following embodiment/feature/aspect, further comprising:
disengaging the first portable module from the first base module while the patient is connected to the first extracorporeal blood circuit tubing set;
engaging the first portable module with a second base module while the patient is connected to the first extracorporeal blood circuit tubing set; and
performing at least a second blood treatment comprising blood circulation, hemodialysis, hemofiltration, hemodiafiltration, or any combination thereof, while the first portable module is engaged with the second base module.

65. The method of any preceding or following embodiment/feature/aspect, further comprising:
disengaging the first portable module from the first base module; and
performing at least one blood treatment on the patient, using the first portable module independent of any base module, wherein the at least one blood treatment comprises blood circulation hemodialysis, hemofiltration, hemodiafiltration, or any combination thereof.

66. A method comprising:
providing the modular system of any preceding or following embodiment/feature/aspect;
connecting a patient to the first extracorporeal blood circuit tubing set;
performing at least one blood treatment on the patient, using the first portable module independent of the first base module;
then, without disconnecting the patient from the first extracorporeal blood circuit tubing set, engaging the first portable module with the first base module; and
performing at least one blood treatment on the patient while the first portable module is engaged with the first base module.

67. A portable blood circulation unit for an extracorporeal blood circuit, the portable blood circulation unit comprising:

a housing configured to engage a blood treatment apparatus comprising a blood pump configured to pump blood from and to a patient extracorporeally through an extracorporeal blood circuit;

a unit blood pump mounted in or on the housing and configured to releasably engage and circulate blood through an extracorporeal short circuit blood circuit;

a battery-powered power source configured to power the unit blood pump;

an extracorporeal short circuit blood circuit releasably engaged with the unit blood pump, the extracorporeal short circuit blood circuit and the housing being together configured to provide a bypass mode of operation wherein the portable blood circulation unit is not engaged with a blood treatment apparatus and blood is circulated to and from the patient, through the extracorporeal short circuit blood circuit, independent of a blood treatment apparatus; and a first inter-module connector configured to connect the portable blood circulation unit to a blood treatment apparatus and form a fluid communication between the extracorporeal short circuit blood circuit and a base module blood circuit of the blood treatment apparatus.

68. In combination, the portable blood circulation unit of any preceding or following embodiment/feature/aspect and a blood treatment apparatus, the blood treatment apparatus comprising a base module blood circuit and a second inter-module connector configured to connect the blood treatment apparatus to the portable blood circulation unit and to form a fluid communication between the extracorporeal short circuit blood circuit and the base module blood circuit.

69. The combination of any preceding or following embodiment/feature/aspect, wherein the first and second inter-module connectors are configured such that, when connected, a full blood circulation mode of operation is provided wherein blood is circulated to and from the patient, through the extracorporeal short circuit blood circuit, and through the base module blood circuit.

70. A method comprising:

providing the portable blood circulation unit of any preceding or following embodiment/feature/aspect;

connecting the extracorporeal short circuit blood circuit to a patient;

engaging the first inter-module connector to a blood treatment apparatus having a complementary second inter-module connector;

disengaging the portable blood circulation unit from the blood treatment apparatus; and engaging the first inter-module connector with a second blood treatment apparatus or reengaging the first inter-module connector with the blood treatment apparatus.

71. A portable blood circuit adapter comprising:

an adapter housing configured to alternatively engage respective apparatus housings of at least two different blood treatment apparatuses comprising respective blood pumps configured to pump blood extracorporeally; and an extracorporeal blood circuit attached to the adapter housing, the extracorporeal blood circuit configured to alternatively engage the respective blood pumps.

72. The portable blood circulation adapter of any preceding or following embodiment/feature/aspect, wherein the extracorporeal blood circuit comprises an arterial blood line, a blood venous line, and a blood filter in fluid communication, the blood filter configured for fluid communication alternatively with respective dialysate circuits in the at least two different blood treatment apparatuses.

73. The portable blood circulation adapter of any preceding or following embodiment/feature/aspect, wherein the blood filter is a dialyzer.

74. The portable blood circulation adapter of any preceding or following embodiment/feature/aspect, further comprising a closure system configured to (1) interrupt fluid communication between the blood filter and the respective dialysate circuits when the blood circulation adapter is disengaged from the respective blood treatment apparatuses, and (2) provide fluid communication between the blood filter and the respective dialysate circuits when the blood circulation adapter is alternatively engaged with the respective blood treatment apparatuses.

75. The portable blood circulation adapter of any preceding or following embodiment/feature/aspect, wherein the closure system comprises a first valve set comprising a first plurality of valves configured to alternatively provide fluid communication between the blood filter and the respective dialysate circuits when the blood circulation adapter is alternatively engaged with the respective blood treatment apparatuses.

76. A modular system comprising:

the portable blood circulation adapter of any preceding or following embodiment/feature/aspect, further comprising an adapter dialysate circuit and a blood filter in fluid communication with the extracorporeal blood circuit and the adapter dialysis circuit;

a blood treatment apparatus comprising a blood pump and an apparatus dialysate circuit, the apparatus configured to engage the blood circulation adapter and perform at least one blood treatment on a patient; and a closure system configured to provide fluid communication between the adapter dialysate circuit and the apparatus dialysate circuit.

77. A method comprising:

providing the modular system of any preceding or following embodiment/feature/aspect;

connecting the extracorporeal blood circuit to the patient;

engaging the portable blood circuit adapter with the blood treatment apparatus opening the closure system to provide fluid communication of dialysate between the blood circulation adapter and the apparatus; and performing at least one blood treatment on the patient.

78. A portable blood circuit adapter comprising:

a module connector including an outlet channel and an inlet channel;

a first fluid path between the inlet channel and a venous line having a patient end;

a second fluid bath between the outlet channel and an arterial line having a patient end; and a closure system having a first valve connected to the outlet channel and a second valve connected to the inlet channel, the closure system being configured to:

(1) interrupt fluid communication between the fluid paths and the module connector in response to a disconnection between the removable module adapter and a first blood treatment apparatus, and (2) provide fluid communication between the fluid paths and the module connector in response to a connection between the removable module adapter and a second blood treatment apparatus.

79. The portable blood circuit adapter of any preceding or following embodiment/feature/aspect, the module connector further comprising a fluid path connecting the venous line to the arterial line.

80. The portable blood circuit adapter of any preceding or following embodiment/feature/aspect, wherein the closure system is further configured to maintain fluid communication between the venous and arterial lines and the module connector while the portable blood circuit adapter is disconnected from the first blood treatment apparatus.

81. The portable blood circuit adapter of any preceding or following embodiment/feature/aspect, further comprising at least one alignment member configured to mate with a corresponding alignment member of each blood treatment apparatus.

82. The portable blood circuit adapter of any preceding or following embodiment/feature/aspect, wherein each blood treatment apparatus is a dialysis machine.

83. The portable blood circuit adapter of any preceding or following embodiment/feature/aspect, wherein at least one valve is configured to obstruct fluid flow to interrupt fluid communication.

84. The portable blood circuit adapter of any preceding or following embodiment/feature/aspect, wherein at least one valve is configured to permit fluid flow to provide fluid communication.

85. A modular system comprising:
 a removable module adapter comprising:
 a module connector including an outlet channel and an inlet channel;
 a first fluid path between the inlet channel and a venous line having a patient end;
 a second fluid bath between the outlet channel and an arterial line having a patient end;
 a closure system having a first valve connected to the outlet channel and a second valve connected to the inlet channel, the closure system being configured to:
  (1) interrupt fluid communication between the fluid paths and the module connector in response to a disconnection between the removable module adapter and a blood treatment apparatus, and
  (2) provide fluid communication between the fluid paths and the module connector in response to a connection between the removable module adapter and a blood treatment apparatus; and
 a portable blood treatment apparatus comprising:
 a connector comprising a portable blood circuit having blood lines that correspond to the inlet and outlet channels of the removable module adapter, and
 a blood pump configured to circulate blood through the fluid paths and the portable blood circuit in response to a connection between the portable removable module adapter and the portable blood treatment apparatus.

86. The modular system of any preceding or following embodiment/feature/aspect, the portable blood treatment apparatus further comprises a dialysate circuit and a blood filter, wherein the blood filter is in fluid communication with the portable blood circuit and the dialysate circuit.

87. The modular system of any preceding or following embodiment/feature/aspect, wherein the portable blood treatment apparatus further comprises:
 a dialysate pump in operable communication with the dialysate circuit,
 a sorbent cartridge in fluid communication with the dialysate circuit, and
 a heater in operable communication with the dialysate circuit.

88. The modular system of any preceding or following embodiment/feature/aspect, further comprising a stationary blood treatment apparatus comprising:
 a connector comprising a stationary blood circuit with blood lines that correspond to the inlet and outlet channels; and
 a second blood pump configured to circulate blood through the fluid paths and the stationary blood circuit in response to a connection between the removable module adapter and the stationary blood treatment apparatus.

89. The modular system of any preceding or following embodiment/feature/aspect, the stationary blood treatment apparatus further comprising a dialysate circuit and a blood filter, wherein the blood filter is in fluid communication with the stationary blood circuit and the dialysate circuit.

The present disclosure can include any combination of these various features or embodiments above and/or below as set forth in sentences and/or paragraphs. Any combination of disclosed features herein is considered part of the present disclosure and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A modular system comprising:
 a first base module comprising a dock and configured to dock a portable extracorporeal blood circuit module, the first base module comprising a base module housing, a primary dialysate circuit comprising a primary dialysate pump, a primary dialysate line, and a first inter-module connector; and
 a first portable module configured to dock to the first base module to form a docked configuration, and configured to be undocked from the first base module in an undocked configuration and to operate independently of the first base module in the undocked configuration, the first portable module comprising a first portable module housing, a blood pump mounted in or on the first portable module housing, a first extracorporeal blood circuit tubing set, and a second inter-module connector complementary to the first inter-module connector and configured to connect to the first inter-module connector in the docked configuration, the first portable module configured to circulate blood through the first extracorporeal blood circuit tubing set in the docked configuration and configured to circulate blood through the first extracorporeal blood circuit tubing set in the undocked configuration, independent of the first base module or any other base module, wherein the blood pump is configured to releasably engage the first extracorporeal blood circuit tubing set.

2. The modular system of claim 1, wherein the primary dialysate circuit further comprises a blood filter in fluid communication with the primary dialysate line, the first inter-module connector is in fluid communication with the blood filter, and the second inter-module connector is in fluid communication with the first extracorporeal blood circuit tubing set.

3. The modular system of claim 2, wherein the blood filter comprises a dialyzer, and the primary dialysate circuit further comprises a primary heater, a sorbent cartridge, a temperature sensor configured for sensing a temperature of dialysate in the dialysate circuit, a conductivity sensor configured for sensing a conductivity of dialysate in the dialysate circuit, a weighing subsystem configured for weighing dialysate in the dialysate circuit, and a secondary heater.

4. The modular system of claim 1, wherein the first extracorporeal blood circuit tubing set comprises a blood filter, the blood filter comprises a membrane that separates the blood filter into a blood side of the blood filter and a dialysate side of the blood filter, the dialysate side of the blood filter is in fluid communication with the second inter-module connector, and the primary dialysate line is in fluid communication with the first inter-module connector.

5. The modular system of claim 4, wherein the first extracorporeal blood circuit tubing set comprises an arterial line, the blood filter, and a venous line, and both the arterial line and the venous line are in fluid communication with the blood side of the blood filter.

6. The modular system of claim 1, further comprising a central control subsystem comprising a central control user interface and being configured to control the first portable module, wherein the first base module further comprises a primary user interface, and the first portable module further comprises a secondary user interface.

7. The modular system of claim 1, further comprising a mobile communications device comprising a mobile communications device user interface and being configured to control the first portable module.

8. The modular system of claim 1, wherein the first base module housing comprises a receptacle at least partially defining the first inter-module connector and being configured to receive and secure at least a portion of the first portable module housing including the second inter-module connector.

9. The modular system of claim 1, wherein the first portable module comprises a cart, a set of wheels, a wheeled bag, a belt, a waist pack, a neck strap, a shoulder strap, a shoulder harness, a backpack, a chest pack, or any combination thereof.

10. The modular system of claim 1, wherein the first inter-module connector comprises one or more valves that are configured to be in an open state in the docked configuration and to be in a closed state in the undocked configuration, and wherein the first portable module housing is configured to engage the base module housing at an interface between the first and second inter-module connectors by a hook and loop combination connector, a latch, a lock, a snap-fit connector, a frictional engagement, a magnetic coupling connector, or any combination thereof.

11. The modular system of claim 1, wherein the first extracorporeal blood circuit tubing set comprises a blood filter, the blood filter comprises a membrane that separates the blood filter into a blood side of the blood filter and a dialysate side of the blood filter, the first portable module further comprises a secondary dialysate circuit comprising a secondary dialysate pump, and the secondary dialysate circuit is in fluid communication with the dialysate side of the blood filter.

12. The modular system of claim 11, wherein the secondary dialysate circuit further comprises a dialysate reservoir, the second inter-module connector is in fluid communication with the dialysate reservoir, and the secondary dialysate pump is located along the secondary dialysate circuit between the blood filter and the dialysate reservoir.

13. The modular system of claim 1, wherein the first inter-module connector further comprises a first electrical connector, the second inter-module connector further comprises a second electrical connector that is complementary to the first electrical connector, and the first portable module further comprises a battery-operated auxiliary power source.

14. The modular system of claim 1, further comprising an engagement verification subsystem configured to generate a detectable signal when the first portable module is securely engaged with the first base module in the docked configuration, wherein the detectable signal comprises a visual signal, an audible signal, a haptic signal, or any combination thereof.

15. The modular system of claim 14, wherein the engagement verification subsystem is configured to generate a second detectable signal when the first portable module is disengaged from the first base module in the undocked configuration, and the second detectable signal comprises a visual signal, an audible signal, a haptic signal, or any combination thereof.

16. The modular system of claim 1, further comprising a second portable module configured to dock to the first base module to form a docked configuration, and configured to be undocked from the first base module in an undocked configuration and to operate independently of the first base module in the undocked configuration, the second portable module comprising a second portable module housing, a second blood pump mounted in or on the second portable module housing, a second extracorporeal blood circuit tubing set, and a third inter-module connector complementary to the first inter-module connector and configured to connect to the first inter-module connector, wherein the second blood pump is configured to releasably engage the second extracorporeal blood circuit tubing set.

17. The modular system of claim 16, wherein the second portable module differs from the first portable module and is configured to perform a different blood treatment on a patient than is the first portable module.

18. The modular system of claim 1, further comprising a second base module comprising a dock configured to dock the first portable module, wherein the first and second base modules are in different respective rooms of a building, are on different respective levels of a building, or are in different respective buildings.

19. The modular system of claim 18, wherein the second base module differs from the first base module and the first and second base modules are configured to perform different blood treatments with respect to one another.

20. A method comprising:
providing the modular system of claim 1;
connecting a patient to the first extracorporeal blood circuit tubing set;
performing at least one blood treatment on the patient, using the first portable module independent of the first base module or any other base module;
then, without disconnecting the patient from the first extracorporeal blood circuit tubing set, engaging the first portable module with the first base module to form the docked configuration; and performing at least one blood treatment on the patient while the first portable module is engaged with the first base module in the docked configuration.

21. A method comprising:

providing a modular system, the modular system comprising
- a first base module comprising a dock and configured to dock a portable extracorporeal blood circuit module, the first base module comprising a base module housing, a primary dialysate circuit comprising a primary dialysate pump, a primary dialysate line, and a first inter-module connector, and
- a first portable module configured to dock to the first base module to form a docked configuration and configured to be undocked from the first base module in an undocked configuration and to operate independently of the first base module in the undocked configuration, the first portable module comprising a first portable module housing, a blood pump mounted in or on the first portable module housing, a first extracorporeal blood circuit tubing set, and a second inter-module connector complementary to the first inter-module connector and configured to connect to the first inter-module connector in the docked configuration, the first portable module configured to circulate blood through the first extracorporeal blood circuit tubing set in the docked configuration and configured to circulate blood through the first extracorporeal blood circuit tubing set in the undocked configuration, independent of the first base module or any other base module, wherein the blood pump is configured to releasably engage the first extracorporeal blood circuit tubing set;

connecting a patient to the first extracorporeal blood circuit tubing set;

engaging the first portable module with the first base module to form the docked configuration; and performing at least one blood treatment on the patient, comprising hemodialysis, hemofiltration, hemodiafiltration, or any combination thereof, in the docked configuration.

22. The method of claim 21, further comprising:

disengaging the first portable module from the first base module to form the undocked configuration;

circulating blood through the first extracorporeal blood circuit tubing set while the first portable module is disengaged from the first base module in the undocked configuration; and engaging a second portable module with the first base module to form a docked configuration with the second portable module.

23. The method of claim 21, further comprising:

disengaging the first portable module from the first base module to form the undocked configuration;

circulating blood through the first extracorporeal blood circuit tubing set while the first portable module is disengaged from the first base module in the undocked configuration;

moving the patient and the first portable module while the patient is connected to the first extracorporeal blood circuit tubing set, to a location that is remote from the first base module; and engaging the first portable module with a second base module to form a docked configuration with the second base module, while the patient remains connected to the first extracorporeal blood circuit tubing set.

24. The method of claim 21, further comprising:

disengaging the first portable module from the first base module while the patient is connected to the first extracorporeal blood circuit tubing set to form the undocked configuration;

circulating blood through the first extracorporeal blood circuit tubing set while the first portable module is disengaged from the first base module in the undocked configuration;

engaging the first portable module with a second base module to form a docked configuration with the second base module, while the patient is connected to the first extracorporeal blood circuit tubing set; and performing at least a second blood treatment comprising blood circulation, hemodialysis, hemofiltration, hemodiafiltration, or any combination thereof, while the first portable module is engaged with the second base module.

25. The method of claim 21, further comprising:

disengaging the first portable module from the first base module to form the undocked configuration; and performing at least one blood treatment on the patient, using the first portable module independent of any base module, wherein the at least one blood treatment comprises blood circulation hemodialysis, hemofiltration, hemodiafiltration, or any combination thereof.

* * * * *